US011241415B2

(12) United States Patent
Duarte et al.

(10) Patent No.: US 11,241,415 B2
(45) Date of Patent: *Feb. 8, 2022

(54) N-METHYL-N-(1-PHENYL-2-(1-PYRROLIDINYL)ETHYL)-2-AMINOPHENYLACETAMIDE DERIVATIVES AGONISTS FOR THE κ OPIOID RECEPTOR

(71) Applicant: Nektar Therapeutics, San Francisco, CA (US)

(72) Inventors: Franco J. Duarte, Walnut Creek, CA (US); Neel K. Anand, San Mateo, CA (US); Wen Zhang, San Ramon, CA (US); Pankaj Sharma, New Delhi (IN); Devendrapratap Singh, Mumbai (IN)

(73) Assignee: Nektar Therapeutics, San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/412,096

(22) Filed: May 14, 2019

(65) Prior Publication Data
US 2019/0269652 A1 Sep. 5, 2019

Related U.S. Application Data

(63) Continuation of application No. 15/539,061, filed as application No. PCT/US2015/066725 on Dec. 18, 2015, now Pat. No. 10,322,107.

(30) Foreign Application Priority Data

Dec. 23, 2014 (IN) .......................... 3872/DEL/2014

(51) Int. Cl.
| | |
|---|---|
| *A61K 31/4025* | (2006.01) |
| *C07D 213/71* | (2006.01) |
| *C07D 231/18* | (2006.01) |
| *C07D 333/34* | (2006.01) |
| *C07D 239/60* | (2006.01) |
| *C07D 261/10* | (2006.01) |
| *C07D 207/12* | (2006.01) |
| *C07D 207/14* | (2006.01) |
| *C07D 295/13* | (2006.01) |
| *C07D 295/135* | (2006.01) |
| *C07D 207/04* | (2006.01) |

(52) U.S. Cl.
CPC ........ *A61K 31/4025* (2013.01); *C07D 207/04* (2013.01); *C07D 207/12* (2013.01); *C07D 207/14* (2013.01); *C07D 213/71* (2013.01); *C07D 231/18* (2013.01); *C07D 239/60* (2013.01); *C07D 261/10* (2013.01); *C07D 295/13* (2013.01); *C07D 295/135* (2013.01); *C07D 333/34* (2013.01)

(58) Field of Classification Search
None
See application file for complete search history.

(56) References Cited

U.S. PATENT DOCUMENTS

| | | |
|---|---|---|
| 5,232,978 A | 8/1993 | Gottschlich et al. |
| 10,322,107 B2 | 6/2019 | Duarte et al. |
| 2003/0144272 A1 | 7/2003 | Kumar et al. |
| 2005/0136031 A1 | 6/2005 | Bentley et al. |
| 2010/0048602 A1 | 2/2010 | Riggs-Sauthier et al. |
| 2017/0368029 A1 | 12/2017 | Duarte et al. |

FOREIGN PATENT DOCUMENTS

| | | |
|---|---|---|
| WO | WO 2014/146111 A2 | 9/2014 |
| WO | WO 2014/210436 A2 | 12/2014 |

OTHER PUBLICATIONS

Dehaven-Hudkins et al., "Peripherally Restricted Opioid Agonists as Novel Analgesic Agents", Current Pharmaceutical Design, vol. 10, pp. 743-757, (2004).
Ertl et al., "Fast Calculation of Molecular Polar Surface Area as a Sum of Fragment-Based Contributions and Its Application to the Prediction of Drug Transport Properties", J. Med. Chem., vol. 43, pp. 3714-3717, (2000).
Kelder et al., "Polar Molecular Surface as a Dominating Determinant for Oral Absorption and Brain Penetration of Drugs", Pharmaceutical Research, vol. 16, No. 10, pp. 1514-1519, (1999).
Kumar et al., "Synthesis and evaluation of novel peripherally restricted κ-opioid receptor agonists", Bioorganic & Medicinal Chemistry Letters, vol. 15, pp. 1091-1095, (2005).
Rubin et al., "The Cell Biology of the Blood-Brain Barrier", Annu. Rev. Neurosci, vol. 22, pp. 11-28, (1999).
Summerfield et al., "Central Nervous System Drug Disposition: The Relationship between in Situ Brain Permeability and Brain Free Fraction", The Journal of Pharmacology and Experimental Therapeutics, vol. 322, No. 1, pp. 205-213, (2007).
Tsuji, "Small Molecular Drug Transfer across the Blood-Brain Barrier via Carrier-Mediated Transport Systems", NeuroRx: The Journal of the American Society for Experimental NueroTherapeutics, vol. 2, pp. 54-62, (Jan. 2005).
PCT International Search Report corresponding to PCT Patent Application No. PCT/US2015/066725 dated Jun. 6, 2016.
PCT International Preliminary Report on Patentability corresponding to PCT Patent Application No. PCT/US2015/066725 dated Jul. 6, 2017.
Enzon Pharmaceuticals, Macromolecular Engineering Technologies, 16 pages, (2004).
Nektar™—Transforming Therapeutics, Nektar Molecule Engineering: Polyethylene Glycol and Derivatives for Advanced PEGylation, 24 pages, Catalog—2003, (Jul. 2003).

(Continued)

*Primary Examiner* — Samantha L Shterengarts
(74) *Attorney, Agent, or Firm* — Jacqueline F. Mahoney

(57) ABSTRACT

Compounds and pharmaceutically acceptable salts and solvates thereof are described. The compounds relate to and/or have application(s) in (among others) the fields of drug discovery, pharmacotherapy, physiology and organic chemistry.

5 Claims, No Drawings

(56) References Cited

OTHER PUBLICATIONS

Nektar™—Transforming Therapeutics, Nektar Advanced PEGylation: Polyethylene Glycol and Derivatives for Advanced PEGylation, 27 pages, Catalog—2004, (Jul. 2004).

Nektar™—Transforming Therapeutics, Nektar Advanced PEGylation: Polyethylene Glycol and Derivatives for Advanced PEGylation, 33 pages, (Catalog 2005-2006).

NOF Corporation, PEG Derivatives, Phospholipid and Drug Delivery Materials for Pharmaceuticals, 46 pages, Catalogue 2003-1$^{st}$, (Jan. 2003).

NOF Corporation, PEG Derivatives, Phospholipid and Drug Delivery Materials for Pharmaceuticals, 27 pages, Catalogue 2003-2$^{nd}$, (Mar. 2004).

NOF Corporation, PEG Derivatives, Phospholipids and Drug Delivery Materials for Pharmaceutical Products and Formulations, 60 pages, Catalogue Ver. 8, (Apr. 2006).

POLYPURE Products, PEG amines; PEG acids and amino acids; PEG thiols and disulfides; BIOTINS, 5 pages, (Apr. 2004).

POLYPURE Products, PEG amines; PEG acids and amino acids; PEG thiols and disulfides; BIOTINS, 5 pages, (Apr. 2005).

Quanta Biodesign, Labeling, Derivatization and Crosslinking Reagents for Biological and Related Materials with dPEG™, 38 pages, (Mar. 12, 2004).

Quanta Biodesign, Labeling, Modification and Crosslinking Reagents incorporating our unique monodispersed dPEG™ Technology, 31 pages, (Nov. 5, 2004).

Quanta Biodesign, Ltd., Leading innovator, producer and provider of monodisperse discrete PEG™ (dPEG™) derivatives, (Product Catalog), 26 pages, (Updated: Jul. 18, 2005).

Quanta Biodesign, Ltd., Leading innovator, producer and provider of monodisperse discrete PEG™ (dPEG™) derivatives, (Product Catalog), 26 pages, (Updated: Nov. 17, 2005).

Shearwater Polymers, Inc., Polyethylene Glycol Derivatives, 50 pages, Catalog—(Mar. 1995).

Shearwater Polymers, Inc., Polyethylene Glycol Derivatives, 55 pages, Catalog 1997-1998, (Jul. 1997).

Shearwater Polymers, Inc., Polyethylene Glycol and Derivatives: Functionalized Biocompatible Polymers for Research and Pharmaceuticals, 50 pages, Catalog—(Jan. 2000).

Shearwater Corporation, Polyethylene Glycol and Derivatives for Biomedical Applications, 20 pages, Catalog—(Jul. 2001).

European Communication corresponding to European Patent Application No. 15 828 717.7-1116 dated May 8, 2018.

English Translation of Notice of Reasons for Rejection corresponding to Japanese Patent Application No. 2017-533825 dated Sep. 30, 2019.

N-METHYL-N-(1-PHENYL-2-(1-PYRROLIDINYL)ETHYL)-2-AMINOPHENYLACETAMIDE DERIVATIVES AGONISTS FOR THE κ OPIOID RECEPTOR

CROSS-REFERENCE TO RELATED APPLICATION

This application is a continuation of U.S. patent application Ser. No. 15/539,061, filed Jun. 22, 2017, now U.S. Pat. No. 10,322,107, which is a 35 U.S.C. § 371 application of International Application NO. PCT/US2015/066725, filed Dec. 18, 2015, designating the United States, which claims the benefit of priority to Indian Patent Application No. 3872/DEL/2014, filed Dec. 23, 2014, the disclosures of which are incorporated herein by reference in their entireties.

BACKGROUND

The present disclosure relates to novel compounds and to their use as agonists of the kappa opioid receptor. The disclosure also relates to methods for preparation of the compounds and to pharmaceutical compositions containing such compounds. The compounds described herein relate to and/or have application(s) in (among others) the fields of drug discovery, pharmacotherapy, physiology, organic chemistry and polymer chemistry.

Kappa opioid agonists that exhibit full agonist properties at the kappa opioid receptor have been widely shown to be efficacious in preclinical models of pain, particularly visceral pain. Kappa opioid agonists are understood to lack several of the side effects of mu opioid agonists, including abuse liability, gastrointestinal transit inhibition and respiratory depression. Kappa opioid agonists, however, are understood to produce complicating side effects, such as dysphoria and sedation at analgesic doses. As a result, the presence of these side effects has hindered the development of kappa opioid agonists as clinically useful analgesics.

Beyond analgesia, kappa agonists have shown anti-inflammatory effects both in vitro and in vivo. Additionally, asimadoline, a kappa opioid agonist that is moderately restricted to the periphery, is currently undergoing studies for the treatment of irritable bowel syndrome. Due to its limited CNS entry, asimadoline may reduce the extent of side effects associated with less restricted kappa agonists, though studies are still ongoing. Additional known kappa opioid agonists, such as enadoline and spiradoline, enter the CNS (central nervous system) causing dysphoria, and thus have not been developed clinically or have been discontinued due to CNS side effects. Further, while mixed agonists (acting on kappa and mu receptors) have been marketed, to date, no full kappa agonist has been approved for use in humans.

The incorporation of a poly(ethylene glycol) moiety into a small molecule scaffold has been utilized to modify the rate of CNS entry of several classes of molecules. U.S. Patent Application Publication No. 2005/0136031 and U.S. Patent Application Publication No. 2010/0048602. The sites of incorporation and further modifications to the molecules, however, have differing effects on the overall activity and pharmacological properties of the resulting molecule.

In view of the above, there remains a need for peripherally acting kappa opioid agonists that retain sufficient efficacy to treat visceral pain and other symptoms or disease states associated with the kappa opioid receptor, while reducing the CNS side effects. The present invention seeks to address these and other needs.

SUMMARY

In the compounds of the invention are structurally encompassed or related to one or more of the following five formulae:

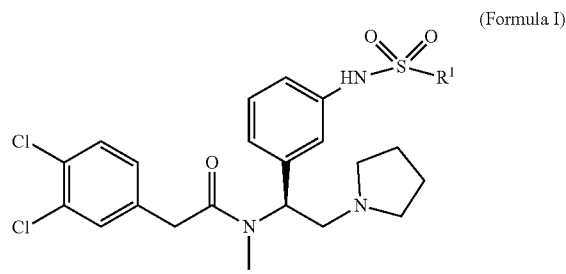
(Formula I)

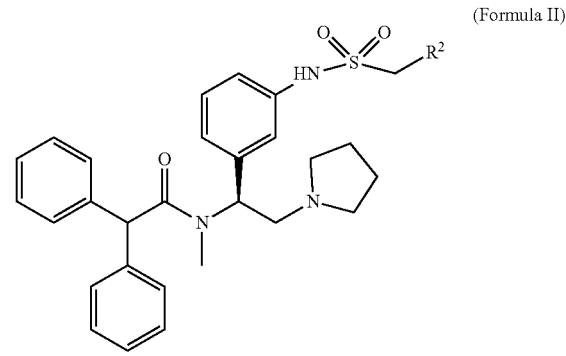
(Formula II)

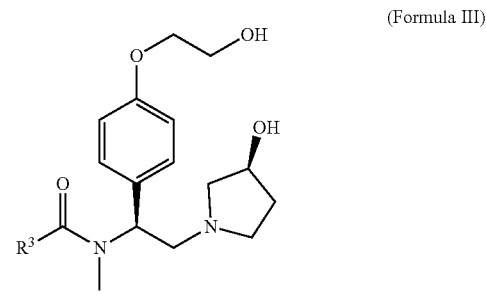
(Formula III)

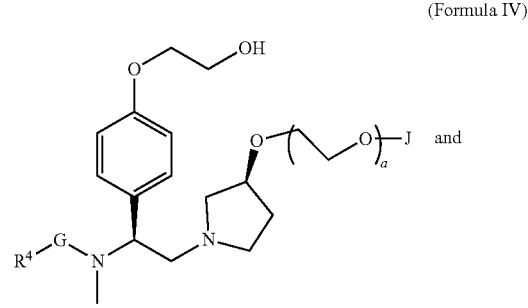
(Formula IV)

and

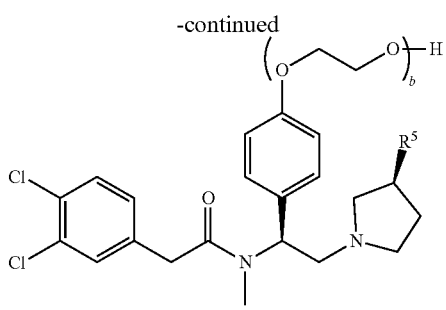

Compounds falling within or related to these structures will be described in further detail below.

In one or more embodiments of the invention, a composition is provided, the composition comprising (i) a compound as described herein, and, optionally, (ii) a pharmaceutically acceptable excipient.

In one or more embodiments of the invention, composition of matter is provided, the composition of matter comprising a compound as described herein, wherein the compound is present in a dosage form.

In one or more embodiments of the invention, a method is provided, the method comprising administering a compound as described herein to a patient in need thereof.

Additional embodiments of the present compounds, compositions, methods, and the like will be apparent from the following description, examples, and claims. As can be appreciated from the foregoing and following description, each and every feature described herein, and each and every combination of two or more of such features, is included within the scope of the present disclosure provided that the features included in such a combination are not mutually inconsistent. In addition, any feature or combination of features may be specifically excluded from any embodiment of the present invention. Additional aspects and advantages of the present invention are set forth in the following description and claims.

DETAILED DESCRIPTION

As used in this specification, the singular forms "a," "an," and "the" include plural referents unless the context clearly dictates otherwise.

In describing and claiming the present invention, the following terminology will be used in accordance with the definitions described below.

"Pharmacologically effective amount," "physiologically effective amount," and "therapeutically effective amount" are used interchangeably herein to mean the amount of a compound of the present invention alone or present in a composition that is needed to provide a threshold level of the compound in the bloodstream or in the target tissue. The precise amount will depend upon numerous factors, e.g., the particular active agent, the components and physical characteristics of the composition, intended patient population, patient considerations, and the like, and can readily be determined by one skilled in the art, based upon the information provided herein and available in the relevant literature.

The term "patient," refers to a living organism suffering from or prone to a condition that can be prevented or treated by administration of a compound as described herein, and includes both humans and animals.

The compounds of the invention, if chiral, may be in a racemic mixture, or an optically active form, for example, a single optically active enantiomer, or any combination or ratio of enantiomers (i.e., scalemic mixture). In addition, the compound may possess one or more geometric isomers. With respect to geometric isomers, a composition can comprise a single geometric isomer or a mixture of two or more geometric isomers. A compound for use in the present invention can be in its customary active form, or may possess some degree of modification.

The compounds of the invention can also exist as tautomeric isomers in certain cases. Although only one delocalized resonance structure may be depicted, all such forms are contemplated within the scope of the invention. For example, ene-amine tautomers can exist for purine, pyrimidine, imidazole, guanidine, amidine, and tetrazole systems and all their possible tautomeric forms are within the scope of the invention.

The term "pharmaceutically acceptable salt" refers to non-toxic salts of the compounds of this invention. Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like. Also included are salts with acidic amino acid such as aspartate and glutamate. Base addition salts include alkali metal salts such as sodium salt and potassium salt; alkaline earth metal salts such as magnesium salt and calcium salt; ammonium salt; organic basic salts such as trimethylamine salt, triethylamine salt, pyridine salt, picoline salt, dicyclohexylamine salt, and N,N'-dibenzylethylenediamine salt; and salts with basic amino acid such as lysine salt and arginine salt. The salts may be in some cases hydrates or solvates.

The term "solvate" refers to a complex formed by the combining of a compound of the present invention and a solvent.

The term "hydrate" refers to the complex formed by the combining of a compound of the present invention and water.

Selected substituents comprising the compounds of Formula I may be present to a recursive degree. In this context, "recursive substituent" means that a substituent may recite another instance of itself. The multiple recitations may be direct or indirect through a sequence of other substituents. Because of the recursive nature of such substituents, theoretically, a large number of compounds may be present in any given embodiment. One of ordinary skill in the art of medicinal chemistry understands that the total number of such substituents is reasonably limited by the desired properties of the compound intended. Such properties include, by way of example and not limitation, physical properties such as molecular weight, solubility or log P, application properties such as activity against the intended target, and practical properties such as ease of synthesis. Recursive substituents may be an intended aspect of the invention. One of ordinary skill in the art of medicinal chemistry understands the versatility of such substituents. To the degree that recursive substituents are present in an embodiment of the invention, they may recite another instance of themselves, 0, 1, 2, 3, or 4 times.

Names of compounds of the present disclosure are provided using ACD/Name software for naming chemical compounds (Advanced Chemistry Development, Inc., Toronto, Canada). Other compounds or radicals may be named with common names or systematic or non-systematic names. In some instances a substituent for a given variable (e.g., $R^3$) within of a generic formula is shown with a dash ("-") as in "—CH$_3$," or with a squiggly line (e.g., "~") as in "~$R^1$;" each are used interchangeably herein. The naming and numbering of the compounds of the disclosure is illustrated with a representative compound of the formula

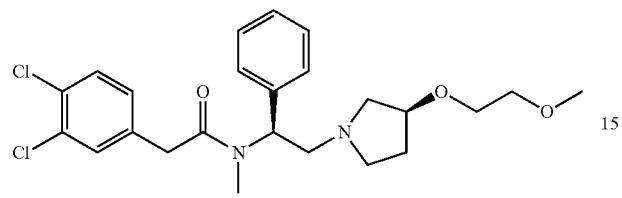

which is named 2-(3,4-dichlorophenyl)-N-{(1S)-2-[(3 S)-3-(2-methoxyethoxy)pyrrolidin-1-yl]-1-phenylethyl}-N-methylacetamide.

In certain embodiments, a compound is provided, the compound having a structure encompassed by the following formula:

(Formula I)

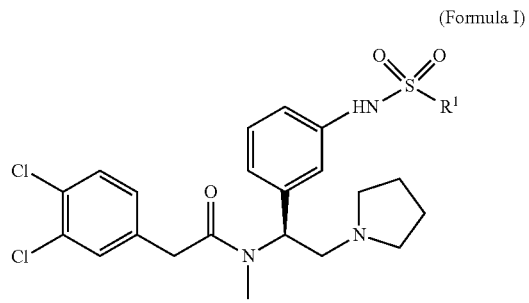

wherein $R^1$ is selected from the group consisting of:

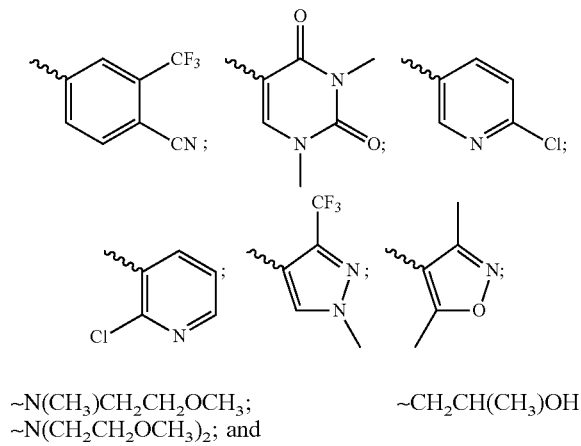

~N(CH$_3$)CH$_2$CH$_2$OCH$_3$;  ~CH$_2$CH(CH$_3$)OH;
~N(CH$_2$CH$_2$OCH$_3$)$_2$; and

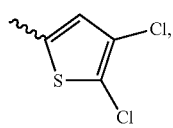

and pharmaceutically acceptable salts and solvates of each of the foregoing.

In certain embodiments, a compound is provided, the compound having a structure encompassed by the following formula:

(Formula II)

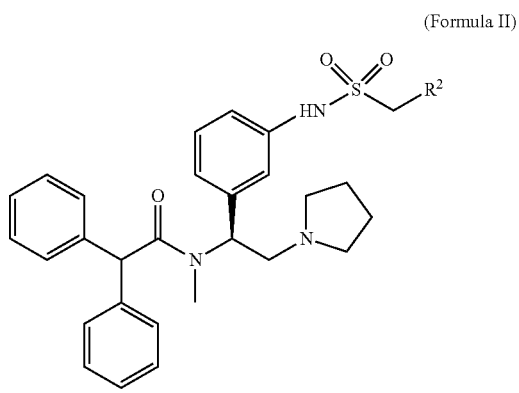

wherein $R^2$ is selected from the group consisting of: ~CH$_2$OCH$_2$CF$_3$; and ~CH(CH$_3$)OH, and pharmaceutically acceptable salts and solvates of each of the foregoing.

In certain embodiments, a compound is provided, the compound having a structure encompassed by the following formula:

(Formula III)

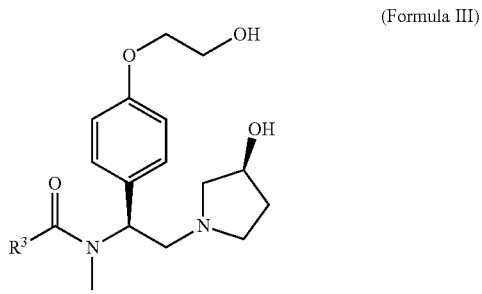

wherein $R^3$ is selected from the group consisting of:

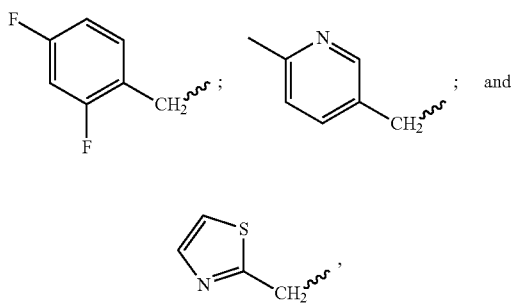

and pharmaceutically acceptable salts and solvates of each of the foregoing.

In certain embodiments, a compound is provided, the compound having a structure encompassed by the following formula:

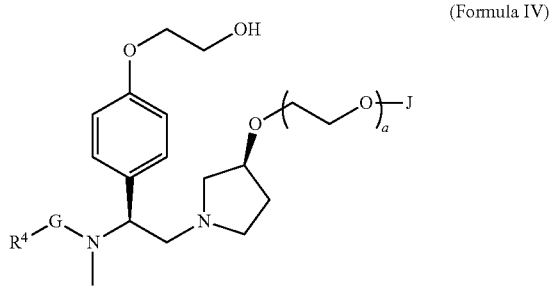

(Formula IV)

wherein:

G is selected from the group consisting of ~C(O)~ and ~S(O)₂~;

(a) is selected from 0, 1, 2, 3 and 4;

R⁴ is selected from the group consisting of:

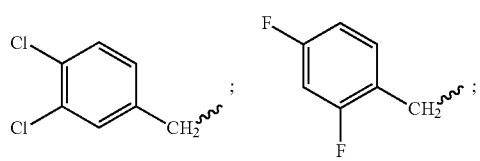

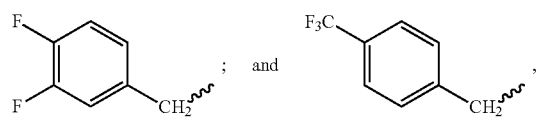

and

J is ~H or ~CF₃, and pharmaceutically acceptable salts and solvates of each of the foregoing, with the provisio that the compound is not

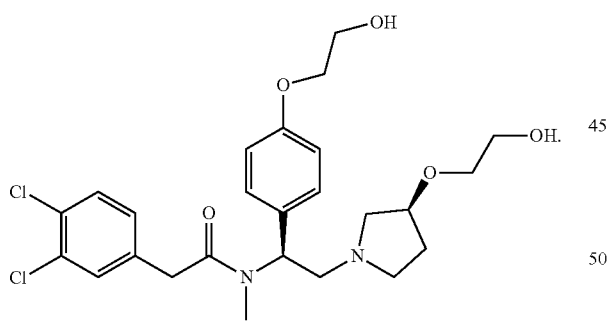

In certain embodiments, a compound is provided, the compound having a structure encompassed by the following formula:

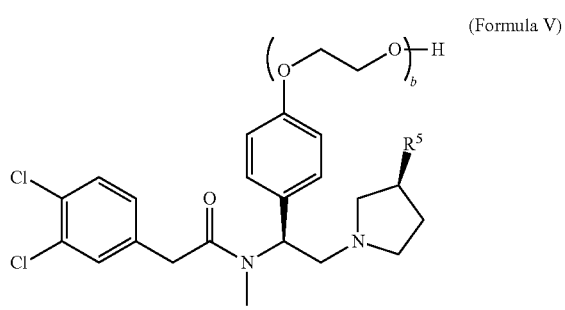

(Formula V)

wherein:

(b) is either 0 or 1; and

R⁵ is selected from the group consisting of:

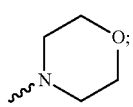

~NHCH₂CH₂OCH₂CH₂OCH₂CH₂OCF₃; ~NHC(CH₃)₃; ~NHCH₃; and ~N(CH₃)₂;

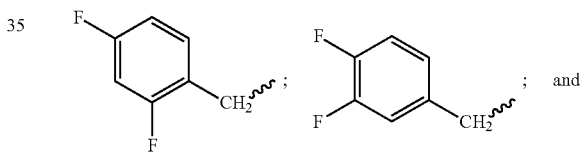

; and

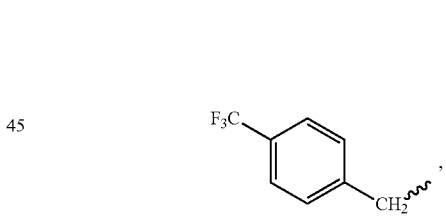

and pharmaceutically acceptable salts and solvates of each of the foregoing.

In certain embodiments, a compound is provided, the compound being selected from the group consisting of:

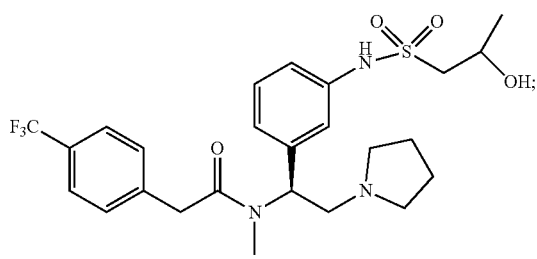

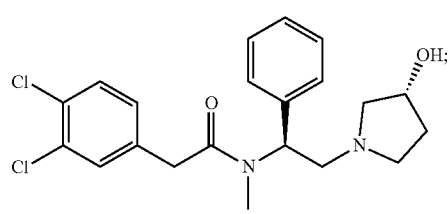

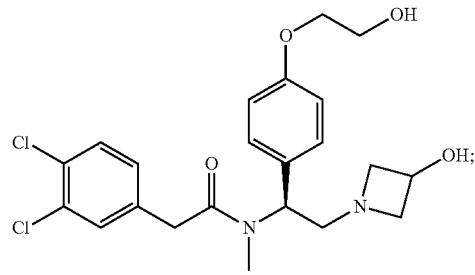
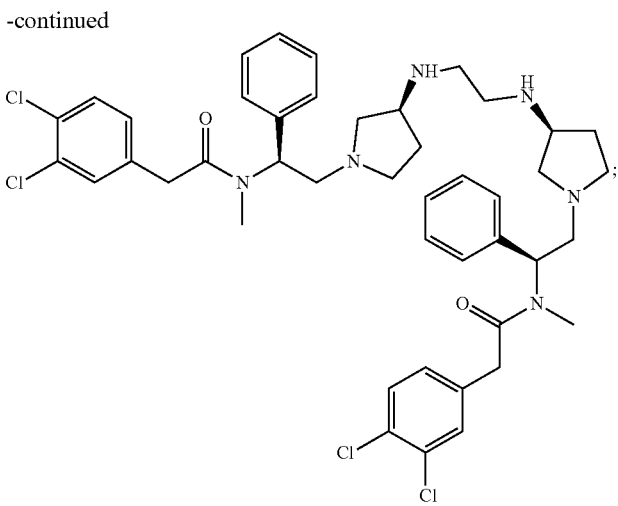
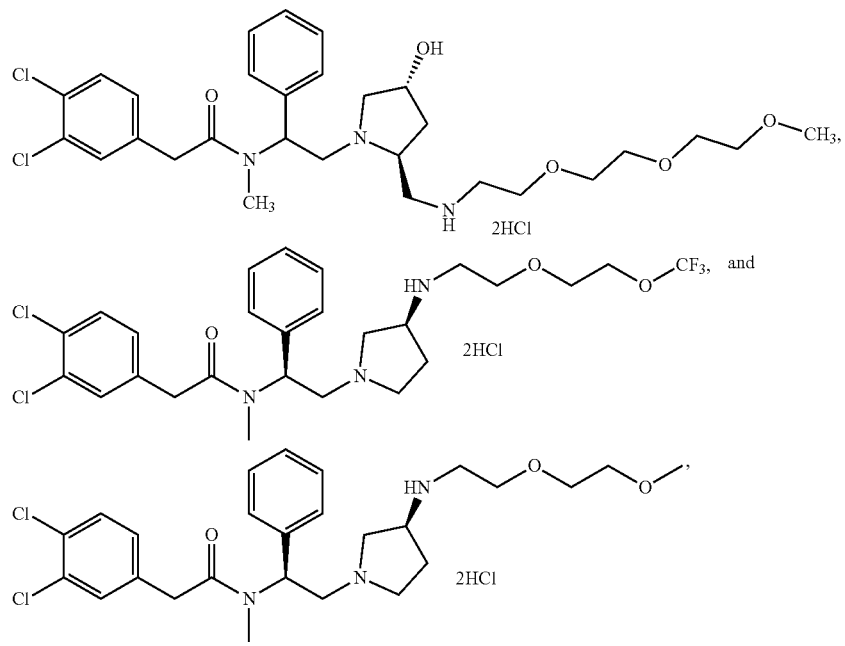

and pharmaceutically acceptable salts and solvates of each of the foregoing.

The compounds of the present invention may be prepared in accordance with the approaches described in the examples section.

The compounds of the present invention are understood to have activity as agonists of the kappa opioid receptor. The ability of each compound disclosed herein to act as kappa opioid agonists may be determined using methods known to those of skill in the art and as disclosed herein. The activity of compounds as kappa agonist can be assessed with in-vitro binding and functional assays in kappa opioid receptor expressing cell lines/membranes and compared to known kappa agonists.

Approaches for evaluating analgesic activity of a compound of the present invention in vivo include a "writhing test." Briefly, the compound to be tested is administered [by, for example, injection (e.g., subcutaneous injection)] to the mouse. Thereafter, a 0.5% acetic acid solution is administered (i.p.) to a mouse and the numbers of writhing responses are counted for twenty minutes. Antinociception is quantified as reduction in the number of writhes respective to vehicle.

Beyond acting as kappa opioid agonists, the present compounds are intended to act primarily on kappa opioid receptors in the peripheral nervous system rather than those receptors in the central nervous system. The propensity of a compound of the present invention to cross the blood-brain barrier may be measured by methods known to those of skill in the art and those described herein.

With respect to the blood-brain barrier ("BBB"), this barrier consists of a continuous layer of unique endothelial cells joined by tight junctions. The cerebral capillaries, which comprise more than 95% of the total surface area of the BBB, represent the principal route for the entry of most solutes and drugs into the central nervous system.

As will be understood by one of skill in the art, molecular size, lipophilicity, and P-glycoprotein ("PgP") interaction are among the primary parameters affecting the intrinsic BBB permeability properties of a given molecule. That is to say, these factors, when taken in combination, play a significant role in determining whether a given molecule passes through the BBB. Other factors (e.g., other active transport mechanisms) may also play a role in ultimately determining whether a given molecule will pass through the BBB.

With respect to molecular size, the molecular size plays a significant role in determining whether a given molecule will pass through the BBB. Relatively very large molecules, for example a molecule having a molecular weight of 5,000 Daltons, will not cross the BBB, whereas relatively small molecules are more likely to cross the BBB. Other factors, however, also play a role in BBB crossing. Antipyrine and atenolol are both small molecule drugs; antipyrine readily crosses the BBB, whereas passage of atenolol is very limited, or effectively non-existent. Antipyrine is an industry standard for a high BBB permeation; atenolol is an industry standard for low permeation of the BBB. See, e.g., Summerfield et al., *J Pharmacol Exp Ther* 322:205-213 (2007).

Lipophilicity is also a factor in BBB permeation. Lipophilicity may be expressed as logP (partition coefficient) or in some instances logD (distribution coefficient). The logP (or logD) for a given molecule can be readily assessed by one of skill in the art. The value for logP may be a negative number (more hydrophilic molecules) or a positive number (more hydrophobic molecules). As used herein when referring to logP, "more negative" means moving in the direction, on the logP scale, from positive to negative logP (e.g., a logP of 2.0 is "more negative" than a logP of 4.0, a logP of −2.0 is "more negative" than a logP of −1.0). Molecules having a negative logP (hydrophilic molecules) generally do not permeate the BBB.

Permeability across the BBB is also dependent on the influence of transporters, such as P-glycoprotein, or PgP, an ATP-dependent efflux transporter highly expressed at the BBB. One of skill in the art can readily determine whether a compound is a substrate for PgP using in vitro methods. Compounds which are substrates for PgP in vitro likely will not permeate the BBB in vivo. Conversely, poor substrates for PgP, as assessed in vitro, are generally likely to display in vivo permeability of the BBB, provided the compound meets other criteria as discussed herein and as known to one of skill in the art. See, e.g., Tsuji, *NeuroRx* 2:54-62 (2005) and Rubin and Staddon, *Annu. Rev. Neurosci.* 22:11-28 (1999).

Even in the context of multiple variables (e.g., molecular size, lipophilicity, transporter influences, linkage type), it is possible to anazlyze a particular compounds ability to cross the BBB using methods known to those of skill in the art.

For any given compound whose degree of BBB crossing ability is not readily known, such BBB crossing ability can be determined using a suitable animal model such as an in situ rat brain perfusion ("RBP") model. Briefly, the RBP technique involves cannulation of the carotid artery followed by perfusion with a compound solution under controlled conditions, followed by a wash out phase to remove compound remaining in the vascular space. More specifically, in the RBP model, a cannula is placed in the left carotid artery and the side branches are tied off. A physiologic buffer containing the analyte (typically but not necessarily at a 5 micromolar concentration level) is perfused at a flow rate of about 10 mL/minute in a single pass perfusion experiment. After 30 seconds, the perfusion is stopped and the brain vascular contents are washed out with compound-free buffer for an additional 30 seconds. The brain tissue is then removed and analyzed for compound concentrations via liquid chromatograph with tandem mass spectrometry detection (LC/MS/MS). Alternatively, blood-brain barrier permeability can be estimated based upon a calculation of the compound's molecular polar surface area ("PSA"), which is defined as the sum of surface contributions of polar atoms (usually oxygens, nitrogens and attached hydrogens) in a molecule. The PSA has been shown to correlate with compound transport properties such as blood-brain barrier transport. Methods for determining a compound's PSA can be found, e.g., in, Ertl et al. (2000) *J. Med. Chem.* 43:3714-3717 and Kelder et al. (1999) *Pharm. Res.* 16:1514-1519.

The compounds of the present invention are expected to have varying degrees of activity against the kappa agonist receptor as well as varying degrees to which they cross the BBB. While the compounds of the present invention have activity against the kappa opioid receptor, they are believed to also have some degree of exclusion from the central nervous system.

Brain PK studies may also be conducted to measure the extent of brain entry in-vivo drug concentrations at enter the CNS at various time post-dose. In brief, rodents are administered with the test article (oral, subcutaneous, or other). At various times post dose terminal blood is collected. Then the rodent is transcardially perfused with cold isotonic saline to remove as much blood from the tissues and brain are extracted. Both plasma and brain are measured for drug content with LC/MS/MS.

The locomotor activity (LMA) model may be conducted to measure changes in activity following test article administration, which may be used to assess the CNS effects of the drug. In brief, at a predetermined time post-dose, rats are placed into observation chambers which are equipped with infrared photocells that can sense motion in the x, y, and z planes. Activity is measured as the number of photobeam breaks in a given plane (horizontal or vertical) or total distance traveled.

In further embodiments, the invention provides for compositions comprising the compounds disclosed herein and a pharmaceutically acceptable excipient or carrier. Generally, the compound itself will be in a solid form (e.g., a precipitate), which can be combined with a suitable pharmaceutical excipient that can be in either solid or liquid form.

Exemplary excipients include, without limitation, those selected from the group consisting of carbohydrates, inorganic salts, antimicrobial agents, antioxidants, surfactants, buffers, acids, bases, and combinations thereof.

A carbohydrate such as a sugar, a derivatized sugar such as an alditol, aldonic acid, an esterified sugar, and/or a sugar polymer may be present as an excipient. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myo-inositol, and the like.

The excipient can also include an inorganic salt or buffer such as citric acid, sodium chloride, potassium chloride, sodium sulfate, potassium nitrate, sodium phosphate monobasic, sodium phosphate dibasic, and combinations thereof.

The preparation may also include an antimicrobial agent for preventing or deterring microbial growth. Nonlimiting examples of antimicrobial agents suitable for the present invention include benzalkonium chloride, benzethonium chloride, benzyl alcohol, cetylpyridinium chloride, chlorobutanol, phenol, phenylethyl alcohol, phenylmercuric nitrate, thimersol, and combinations thereof.

An antioxidant can be present in the preparation as well. Antioxidants are used to prevent oxidation, thereby preventing the deterioration of the compound or other components of the preparation. Suitable antioxidants for use in the present invention include, for example, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and combinations thereof.

A surfactant may be present as an excipient. Exemplary surfactants include: polysorbates, such as "Tween 20" and "Tween 80," and pluronics such as F68 and F88 (both of which are available from BASF, Mount Olive, N.J.); sorbitan esters; lipids, such as phospholipids such as lecithin and other phosphatidylcholines, phosphatidylethanolamines (although preferably not in liposomal form), fatty acids and fatty esters; steroids, such as cholesterol; and chelating agents, such as EDTA, zinc and other such suitable cations.

Pharmaceutically acceptable acids or bases may be present as an excipient in the preparation. Nonlimiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Examples of suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and combinations thereof.

The amount of the compound in the composition will vary depending on a number of factors, but will optimally be a therapeutically effective dose when the composition is stored in a unit dose container. A therapeutically effective dose can be determined experimentally by repeated administration of increasing amounts of the compound in order to determine which amount produces a clinically desired endpoint.

The amount of any individual excipient in the composition will vary depending on the activity of the excipient and particular needs of the composition. Typically, the optimal amount of any individual excipient is determined through routine experimentation, i.e., by preparing compositions containing varying amounts of the excipient (ranging from low to high), examining the stability and other parameters, and then determining the range at which optimal performance is attained with no significant adverse effects.

Generally, however, the excipient will be present in the composition in an amount of about 1% to about 99% by weight, in certain embodiments from about 5%-98% by weight, in certain embodiments from about 15-95% by weight of the excipient, and in certain embodiments concentrations less than 30% by weight.

These foregoing pharmaceutical excipients along with other excipients and general teachings regarding pharmaceutical compositions are described in "Remington: The Science & Practice of Pharmacy", 19$^{th}$ ed., Williams & Williams, (1995), the "Physician's Desk Reference", 52$^{nd}$ ed., Medical Economics, Montvale, N.J. (1998), and Kibbe, A. H., Handbook of Pharmaceutical Excipients, 3$^{rd}$ Edition, American Pharmaceutical Association, Washington, D.C., 2000.

The pharmaceutical compositions can take any number of forms and the invention is not limited in this regard. In certain embodiments, preparations are in a form suitable for oral administration such as a tablet, caplet, capsule, gel cap, troche, dispersion, suspension, solution, elixir, syrup, lozenge, transdermal patch, spray, suppository, and powder. Oral dosage forms are preferred for those compounds that are orally active, and include tablets, caplets, capsules, gel caps, suspensions, solutions, elixirs, and syrups, and can also comprise a plurality of granules, beads, powders or pellets that are optionally encapsulated. Such dosage forms are prepared using conventional methods known to those in the field of pharmaceutical formulation and described in the pertinent texts.

Tablets and caplets, for example, can be manufactured using standard tablet processing procedures and equipment. Direct compression and granulation techniques are preferred when preparing tablets or caplets containing the compounds described herein. In addition to the compound, the tablets and caplets will generally contain inactive, pharmaceutically acceptable carrier materials such as binders, lubricants, disintegrants, fillers, stabilizers, surfactants, coloring agents, and the like. Binders are used to impart cohesive qualities to a tablet, and thus ensure that the tablet remains intact. Suitable binder materials include, but are not limited to, starch (including corn starch and pregelatinized starch), gelatin, sugars (including sucrose, glucose, dextrose and lactose), polyethylene glycol, waxes, and natural and synthetic gums, e.g., acacia sodium alginate, polyvinylpyrrolidone, cellulosic polymers (including hydroxypropyl cellulose, hydroxypropyl methylcellulose, methyl cellulose, microcrystalline cellulose, ethyl cellulose, hydroxyethyl cellulose, and the like), and Veegum. Lubricants are used to facilitate tablet manufacture, promoting powder flow and preventing particle capping (i.e., particle breakage) when pressure is relieved. Useful lubricants are magnesium stearate, calcium stearate, and stearic acid. Disintegrants are used to facilitate disintegration of the tablet, and are generally starches, clays, celluloses, algins, gums, or crosslinked polymers. Fillers include, for example, materials such as silicon dioxide, titanium dioxide, alumina, talc, kaolin, powdered cellulose, and microcrystalline cellulose, as well as soluble materials such as mannitol, urea, sucrose, lactose, dextrose, sodium chloride, and sorbitol. Stabilizers, as well known in the art, are used to inhibit or retard drug decomposition reactions that include, by way of example, oxidative reactions.

Capsules are also preferred oral dosage forms, in which case the compound-containing composition can be encapsulated in the form of a liquid or gel (e.g., in the case of a gel cap) or solid (including particulates such as granules, beads, powders or pellets). Suitable capsules include hard and soft capsules, and are generally made of gelatin, starch, or a cellulosic material. Two-piece hard gelatin capsules are preferably sealed, such as with gelatin bands or the like.

Included are parenteral formulations in the substantially dry form (typically as a lyophilizate or precipitate, which can be in the form of a powder or cake), as well as formulations prepared for injection, which are typically liquid and requires the step of reconstituting the dry form of parenteral formulation. Examples of suitable diluents for reconstituting solid compositions prior to injection include bacteriostatic water for injection, dextrose 5% in water, phosphate-buffered saline, Ringer's solution, saline, sterile water, deionized water, and combinations thereof.

In some cases, compositions intended for parenteral administration can take the form of nonaqueous solutions, suspensions, or emulsions, each typically being sterile. Examples of nonaqueous solvents or vehicles are propylene glycol, polyethylene glycol, vegetable oils, such as olive oil and corn oil, gelatin, and injectable organic esters such as ethyl oleate.

The parenteral formulations described herein can also contain adjuvants such as preserving, wetting, emulsifying, and dispersing agents. The formulations are rendered sterile by incorporation of a sterilizing agent, filtration through a bacteria-retaining filter, irradiation, or heat.

The compound can also be administered through the skin using conventional transdermal patch or other transdermal delivery system, wherein the compound is contained within a laminated structure that serves as a drug delivery device to be affixed to the skin. In such a structure, the compound is contained in a layer, or "reservoir," underlying an upper backing layer. The laminated structure can contain a single reservoir, or it can contain multiple reservoirs.

The compound can also be formulated into a suppository for rectal administration. With respect to suppositories, the compound is mixed with a suppository base material which is (e.g., an excipient that remains solid at room temperature but softens, melts or dissolves at body temperature) such as coca butter (*theobroma* oil), polyethylene glycols, glycerinated gelatin, fatty acids, and combinations thereof. Suppositories can be prepared by, for example, performing the following steps (not necessarily in the order presented): melting the suppository base material to form a melt; incorporating the compound (either before or after melting of the suppository base material); pouring the melt into a mold; cooling the melt (e.g., placing the melt-containing mold in a room temperature environment) to thereby form suppositories; and removing the suppositories from the mold.

The invention also provides a method for administering a compound provided herein to a patient suffering from a condition that is responsive to treatment with the compound such as pain. The method comprises administering, generally orally, a therapeutically effective amount of the compound (in certain embodiments provided as part of a pharmaceutical preparation). Other modes of administration are also contemplated, such as pulmonary, nasal, buccal, rectal, sublingual, transdermal, and parenteral. As used herein, the term "parenteral" includes subcutaneous, intravenous, intra-arterial, intraperitoneal, intracardiac, intrathecal, and intramuscular injection, as well as infusion injections.

The method of administering may be used to treat any condition that can be remedied or prevented by administration of a kappa opioid agonist. Most commonly, the compounds provided herein are administered for the management of pain, including visceral pain, chronic pelvic pain and interstitial cystitis. Kappa agonists have also been used to treat irritable bowel syndrome. Those of ordinary skill in the art appreciate which conditions a specific compound can effectively treat. The actual dose to be administered will vary depend upon the age, weight, and general condition of the subject as well as the severity of the condition being treated, the judgment of the health care professional, and compound being administered. Therapeutically effective amounts are known to those skilled in the art and/or are described in the pertinent reference texts and literature. Generally, a therapeutically effective amount will range from about 0.001 mg to 1000 mg, in certain embodiments in doses from 0.01 mg/day to 750 mg/day, and in certain embodiments in doses from 0.10 mg/day to 500 mg/day.

The unit dosage of any given compound (in certain embodiments, provided as part of a pharmaceutical preparation) can be administered in a variety of dosing schedules depending on the judgment of the clinician, needs of the patient, and so forth. The specific dosing schedule will be known by those of ordinary skill in the art or can be determined experimentally using routine methods. Exemplary dosing schedules include, without limitation, administration five times a day, four times a day, three times a day, twice daily, once daily, three times weekly, twice weekly, once weekly, twice monthly, once monthly, and any combination thereof. Once the clinical endpoint has been achieved, dosing of the composition is halted.

All articles, books, patents, patent publications and other publications referenced herein are hereby incorporated by reference in their entireties.

It is to be understood that while the invention has been described in conjunction with certain and specific embodiments, the foregoing description as well as the examples that follow are intended to illustrate and not limit the scope of the invention. Other aspects, advantages and modifications within the scope of the invention will be apparent to those skilled in the art to which the invention pertains.

EXAMPLES

Unless otherwise indicated, all chemical reagents referred to in the appended examples are commercially available and/or can be synthesized in accordance with methods described in the literature unless otherwise indicated.

Example 1

Preparation of (S)—N-(1-(3-(4-cyano-3-(trifluoromethyl)phenylsulfonamido)phenyl)-2-(pyrrolidin-1-yl)ethyl)-2-(3,4-dichlorophenyl)-N-methylacetamide, hydrochloride salt

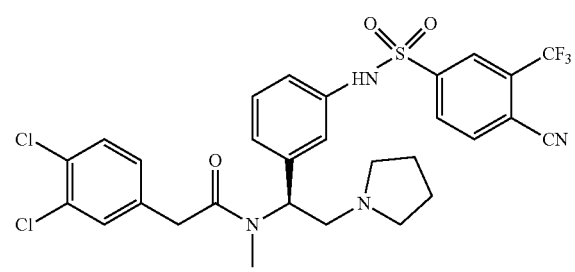 [SMILES: CN(C(=O)Cc1ccc(Cl)c(Cl)c1)[C@H](CN1CCCC1)c1cccc(NS(=O)(=O)c2ccc(C#N)c(C(F)(F)F)c2)c1]

(S)—N-(1-(3-(4-cyano-3-(trifluoromethyl)phenylsulfonamido)phenyl)-2-(pyrrolidin-1-yl)ethyl)-2-(3,4-dichlorophenyl)-N-methylacetamide may be prepared according to the following steps.

Step 1: Preparation of 2-(3,4-dichlorophenyl)-N-methyl-N-[(1S)-1-(3-nitrophenyl)-2-(pyrrolidin-1-yl)ethyl]acetamide

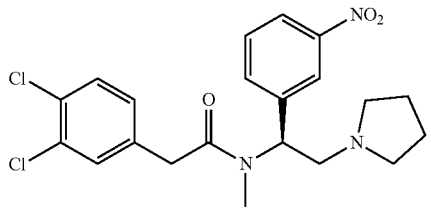 [SMILES: CN(C(=O)Cc1ccc(Cl)c(Cl)c1)[C@H](CN1CCCC1)c1cccc([N+](=O)[O-])c1]

(S)-1-[2-(Methylamino)-2-(3/4-nitrophenyl)ethyl]pyrrolidin (0.66 g, 2.65 mmol) [Portoghese (1994) *Journal of Medicinal Chemistry* 37:4490-4498] was dissolved in anhydrous acetonitrile (14 mL). To the dark solution was added diisopropylethylamine (1.03 mL, 5.82 mmol) at 0° C., followed by 3,4-dichlorophenylacetic acid (0.60 g, 2.91 mmol) and O-(benzotriazol-1-yl)-N,N,N',N'-tetramethyluronium tetrafluoroborate (0.96 g, 2.91 mmol). The reaction mixture was allowed to equilibrate to room temperature. After approximately 17 hours at room temperature the reaction mixture was concentrated under reduced pressure. The residue was taken up in ethyl acetate (15 mL) and washed with saturated sodium bicarbonate (2×25 mL) and saturated sodium chloride (25 mL). The combined organic portion was dried over anhydrous sodium sulfate and concentrated under reduced pressure. Purification by chromatography gave 2-(3,4-dichlorophenyl)-N-methyl-N-[(1S)-1-(3-nitrophenyl)-2-(pyrrolidin-1-yl)ethyl acetamide (0.99 g, 86% yield), as a light-yellow oil. The compound was converted into the hydrochloride salt by dissolving the oil in acetonitrle and adding 1N hydrochloric acid. The solution was lyopholized to give the hydrochloride salt as a white powder. $^1$H NMR (500 MHz, CDCl$_3$): δ 8.13 (m, 2H), 7.66 (m, 1H), 7.51 (m, 1H), 7.37 (m, 2H), 7.15 (m, 1H), 6.11 (m, 1H), 3.77 (m, 2H), 3.13 (m, 1H), 2.80 (m, 1H), 2.69 (s, 3H), 2.60 (m, 2H), 1.76 (m, 4H); MS (EI) for C$_{21}$H$_{23}$C$_{12}$N$_3$O$_3$: 437 (MH$^+$).

Step 2: Preparation of N-[(1S)-1-(3-aminophenyl)-2-(pyrrolidin-1-yl)ethyl]-2-(3,4-dichlorophenyl)-N-methylacetamide

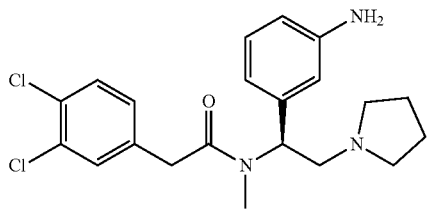

2-(3,4-Dichlorophenyl)-N-methyl-N-[(1S)-1-(3-nitrophenyl)-2-(pyrrolidin-1-yl)ethyl acetamide (0.80 g, 1.77 mmol), hydrazine hydrate (1.36 g, 21.34 mmol) and Raney nickel slurry (1.0 mL) in 95% ethanol (89 mL) was heated to 55° C. After approximately two hours the reaction was complete as indicated by TLC. The reaction mixture was filtered through Celite, and the Raney nickel was washed with hot methanol. The combined filtrates were concentrated under reduced pressure to give 0.60 g (83%) of N-[(1S)-1-(3-aminophenyl)-2-(pyrrolidin-1-yl)ethyl]-2-(3,4-dichlorophenyl)-N-methylacetamide. $^1$H NMR (500 MHz, CDCl$_3$): δ 7.38 (m, 2H), 7.17 (m, 1H), 7.10 (m, 1H), 6.63 (m, 3H), 6.01 (m, 1H), 3.66-3.79 (m, 4H), 3.14 (m, 1H), 2.46-2.72 (m, 5H), 2.47 (m, 3H), 1.74 (m, 4H); MS (EI) for C$_{21}$H$_{25}$C$_{12}$N$_3$O: 406 (MH$^+$).

Step 3: (S)—N-(1-(3-(4-cyano-3-(trifluoromethyl)phenylsulfonamido)phenyl)-2-(pyrrolidin-1-yl)ethyl)-2-(3,4-dichlorophenyl)-N-methylacetamide, hydrochloride salt

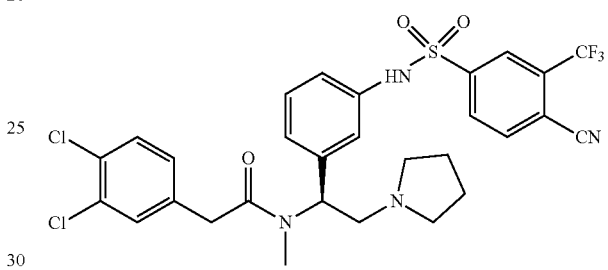

N-[(1S)-1-(3-Aminophenyl)-2-(pyrrolidin-1-yl)ethyl]-2-(3,4-dichlorophenyl)-N-methylacetamide (2) (0.12 g, 0.30 mmol) was dissolved in dichloromethane (6 mL) and anhydrous pyridine (0.18 mL, 2.27 mmol). To the cooled (0° C.) yellow solution there was added dropwise 4-cyano-3-(trifluoromethyl)benzene-1-sulfonyl chloride (0.21 g, 0.75 mmol) in dichloromethane (1 mL). The yellow reaction mixture was stirred at 0° C., and the color turned orange. The reaction mixture was allowed to equilibrate to room temperature. After approximately 17 hours at room temperature, the reaction mixture was diluted with dichloromethane (25 mL) and followed by the addition of water (30 mL). The aqueous portion was extracted with dichloromethane (2×15 mL). In five separate washing steps, the combined organic portions were washed in the following sequence: a 1N hydrochloric acid wash, a water wash, a saturated sodium bicarbonate wash, a second water wash and a brine wash (35 mL each). The organic portion was dried over anhydrous sodium sulfate, filtered, concentrated and purified by chromatography to give 0.08 g (41%) (S)—N-(1-(3-(4-cyano-3-(trifluoromethyl)phenylsulfonamido)phenyl)-2-(pyrrolidin-1-yl)ethyl)-2-(3,4-dichlorophenyl)-N-methylacetamide as a yellow oil. $^1$H NMR (500 MHz, CDCl$_3$): δ 6.89-8.09 (m, 10H), 5.89 (m, 1H), 3.59-3.75 (m, 2H), 3.12 (m, 1H), 2.68 (m, 4H), 2.50 (m, 2H), 1.14 (m, 3H); MS (EI) for C$_{29}$H$_{27}$C$_{12}$F$_3$N$_4$O$_3$S: 639 (MH$^+$).

The compound was converted into the hydrochloride salt by dissolving the oil in acetonitrile and adding 1N hydrochloric acid. The solution was lyopholized to give the hydrochloride salt as an off-white powder.

Example 2

Preparation of (S)-2-(3,4-dichlorophenyl)-N-(1-(3-(1,3-dimethyl-2,4-dioxo-1,2,3,4-tetrahydropyrimidine-5-sulfonamido)phenyl)-2-(pyrrolidin-1-yl)ethyl)-N-methylacetamide, hydrochloride salt

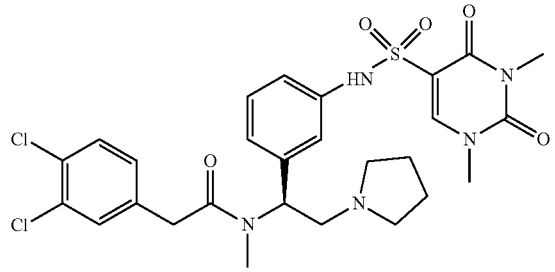 [SMILES: CN(C(=O)Cc1ccc(Cl)c(Cl)c1)[C@H](CN1CCCC1)c1cccc(NS(=O)(=O)c2cn(C)c(=O)n(C)c2=O)c1]

N-[(1S)-1-(3-Aminophenyl)-2-(pyrrolidin-1-yl)ethyl]-2-(3,4-dichlorophenyl)-N-methylacetamide (0.13 g, 0.27 mmol) (preparation described in Step 2 of Example 1) was dissolved in dichloromethane (4.5 mL) and anhydrous pyridine (0.16 mL, 2.06 mmol). To the cooled (0° C.) yellow solution there was added dropwise 1,3-dimethyl-2,4-dioxo-1,2,3,4-tetrahydropyrimidine-5-sulfonyl chloride (0.17 g, 0.68 mmol) in dichloromethane (1 mL). The yellow reaction mixture was allowed to stir at 0° C., and the color turning orange. The reaction mixture was allowed to equilibrate to room temperature. After approximately 17 hours at room temperature, the reaction mixture was diluted with dichloromethane (25 mL) followed by the addition of waster (30 mL). The aqueous portion was extracted with dichloromethane (2×15 mL). In five separate washing steps, the combined organic portions were washed in the following sequence: a 1N hydrochloric acid wash, a water wash, a saturated sodium bicarbonate wash, a second water wash and a brine wash (35 mL each). The organic portion was dried over anhydrous sodium sulfate, filtered, concentrated and purified by chromatography to give 0.085 g (51%) (S)-2-(3,4-dichlorophenyl)-N-(1-(3-(1,3-dimethyl-2,4-dioxo-1,2,3,4-tetrahydropyrimidine-5-sulfonamido)phenyl)-2-(pyrrolidin-1-yl)ethyl)-N-methylacetamide as a yellow oil. $^1$H NMR (500 MHz, CDCl$_3$): δ 6.90-7.29 (m, 7H), 5.86 (m, 1H), 3.69 (m, 3H), 3.39 (m, 4H), 3.28 (m, 4H), 3.05 (m, 1H), 2.68 (m, 4H), 2.44 (m, 3H), 1.71 (m, 4H); MS (EI) for C$_{27}$H$_{31}$Cl$_2$N$_5$O$_5$S: 608 (MH$^+$). The compound was converted into the hydrochloride salt by dissolving the oil in acetonitrile and adding 1N hydrochloric acid. The solution was lyopholized to give the hydrochloride salt as an off-white powder.

Example 3

Preparation of (S)—N-(1-(3-(6-chloropyridine-3-sulfonamido)phenyl)-2-(pyrrolidin-1-yl)ethyl)-2-(3,4-dichlorophenyl)-N-methylacetamide, hydrochloride salt

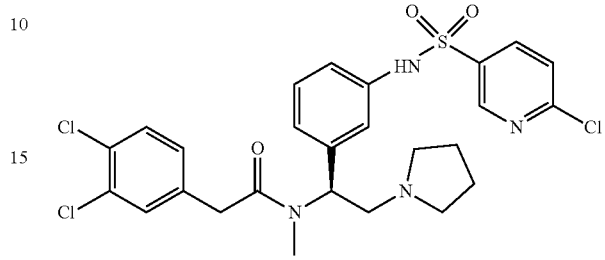

N-[(1S)-1-(3-Aminophenyl)-2-(pyrrolidin-1-yl)ethyl]-2-(3,4-dichlorophenyl)-N-methylacetamide (0.11 g, 0.24 mmol) (preparation described in Step 2 of Example 1) was dissolved in dichloromethane (4 mL) and anhydrous pyridine (0.14 mL, 1.80 mmol). To the cooled (0° C.) yellow solution there was added dropwise 6-chloropyridine-3-sulfonyl chloride (0.13 g, 0.60 mmol) in dichloromethane (1 mL). The yellow reaction mixture was allowed to stir at 0° C., and the color turned orange. The reaction mixture was allowed to equilibrate to room temperature. After approximately 17 hours at room temperature, the reaction mixture was diluted with dichloromethane (25 mL) followed by the addition of water (30 mL). The aqueous portion was extracted with dichloromethane (2×15 mL). In five separate washing steps, the combined organic portions were washed in the following sequence: a 1N hydrochloric acid wash, a water wash, a saturated sodium bicarbonate wash, a second water wash and a brine wash (35 mL each). The organic portion was dried over anhydrous sodium sulfate, filtered, concentrated and purified by chromatography to give 0.085 g (61%) (S)—N-(1-(3-(6-chloropyridine-3-sulfonamido)phenyl)-2-(pyrrolidin-1-yl)ethyl)-2-(3,4-dichlorophenyl)-N-methylacetamide as a yellow oil. MS (EI) for C$_{26}$H$_{27}$Cl$_3$N$_4$O$_3$S: 581 (MH$^+$).

The compound was converted into the hydrochloride salt by dissolving the oil in acetonitrile and adding 1N hydrochloric acid. The solution was lyopholized to give the hydrochloride salt as an off-white powder.

Example 4

Preparation of (S)—N-(1-(3-(2-chloropyridine-3-sulfonamido)phenyl)-2-(pyrrolidin-1-yl)ethyl)-2-(3,4-dichlorophenyl)-N-methylacetamide, hydrochloride salt

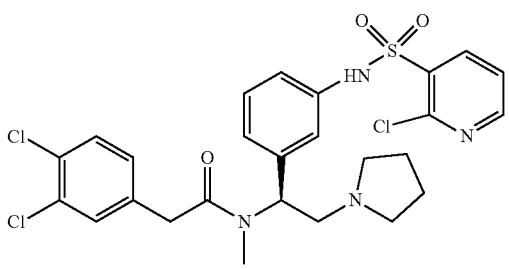 [SMILES: CN(C(=O)Cc1ccc(Cl)c(Cl)c1)[C@H](CN1CCCC1)c1cccc(NS(=O)(=O)c2cccnc2Cl)c1]

N-[(1S)-1-(3-Aminophenyl)-2-(pyrrolidin-1-yl)ethyl]-2-(3,4-dichlorophenyl)-N-methylacetamide (0.11 g, 0.23 mmol) (preparation described in Step 2 of Example 1) was dissolved in dichloromethane (4 mL) and anhydrous pyridine (0.13 mL, 1.72 mmol). To the cooled (0° C.) yellow solution there was added dropwise 2-chloropyridine-3-sulfonyl chloride (0.12 g, 0.57 mmol) in dichloromethane (1 mL). The yellow reaction mixture was allowed to stir at 0° C., and the color turned orange. The reaction mixture was allowed to equilibrate to room temperature. After approximately 17 hours at room temperature, the reaction mixture was diluted with dichloromethane (25 mL) followed by the addition of water (30 mL). The aqueous portion was extracted with dichloromethane (2×15 mL). In five separate washing steps, the combined organic portions were washed in the following sequence: a 1N hydrochloric acid wash, a water wash, a saturated sodium bicarbonate wash, a second water wash and a brine wash (35 mL each). The organic portion was dried over anhydrous sodium sulfate, filtered, concentrated and purified by chromatography to give 0.072 g (54%) (S)—N-(1-(3-(2-chloropyridine-3-sulfonamido)phenyl)-2-(pyrrolidin-1-yl)ethyl)-2-(3,4-dichlorophenyl)-N-methylacetamide as a yellow oil. $^1$H NMR (500 MHz, CDCl$_3$): δ 7.02-8.52 (m, 10H), 6.00 (m, 1H), 3.74 (m, 2H), 2.67 (m, 5H), 2.48 (m, 2H), 1.77 (m, 6H); MS (EI) for $C_{26}H_{27}Cl_3N_4O_3S$: 581 (MH$^+$).

The compound was converted into the hydrochloride salt by dissolving the oil in acetonitrile and adding 1N hydrochloric acid. The solution was lyopholized to give the hydrochloride salt as an off-white powder.

Example 5

Preparation of (S)-2-(3,4-dichlorophenyl)-N-methyl-N-(1-(3-(1-methyl-3-(trifluoromethyl)-1H-pyrazole-4-sulfonamido)phenyl)-2-(pyrrolidin-1-yl)ethyl)acetamide, hydrochloride salt

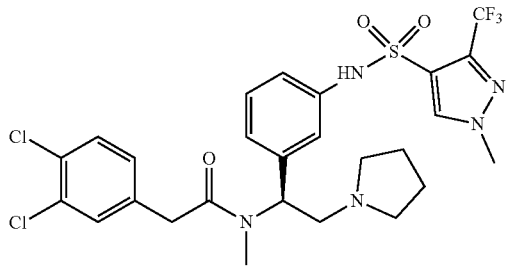 [SMILES: CN(C(=O)Cc1ccc(Cl)c(Cl)c1)[C@H](CN1CCCC1)c1cccc(NS(=O)(=O)c2cn(C)nc2C(F)(F)F)c1]

N-[(1S)-1-(3-Aminophenyl)-2-(pyrrolidin-1-yl)ethyl]-2-(3,4-dichlorophenyl)-N-methylacetamide (0.11 g, 0.23 mmol) (preparation described in Step 2 of Example 1) was dissolved in dichloromethane (4 mL) and anhydrous pyridine (0.13 mL, 1.72 mmol). To the cooled (0° C.) yellow solution there was added dropwise 1-methyl-3-(trifluoromethyl)-1H-pyrazole-4-sulfonyl chloride (0.15 g, 0.57 mmol) in dichloromethane (1 mL). The yellow reaction mixture was allowed to stir at 0° C., and the color turned orange. The reaction mixture was allowed to equilibrate to room temperature. After approximately 17 hours at room temperature, the reaction mixture was diluted with dichloromethane (25 mL) followed by the addition of water (30 mL). The aqueous portion was extracted with dichloromethane (2×15 mL). In five separate washing steps, the combined organic portions were washed in the following sequence: a 1N hydrochloric acid wash, a water wash, a saturated sodium bicarbonate wash, a second water wash and a brine wash (35 mL each). The organic portion was dried over anhydrous sodium sulfate, filtered, concentrated and purified by chromatography to give 0.10 g (70%) (S)-2-(3,4-dichlorophenyl)-N-methyl-N-(1-(3-(1-methyl-3-(trifluoromethyl)-1H-pyrazole-4-sulfonamido)phenyl)-2-(pyrrolidin-1-yl)ethyl) acetamide as a yellow oil. $^1$H NMR (500 MHz, CDCl$_3$): δ 7.05-7.92 (m, 8H), 5.97 (m, 1H), 3.87 (s, 3H), 3.65 (m, 2H), 3.22 (m, 2H), 2.75 (m, 5H), 2.50 (m, 2H), 1.78 (m, 3H); MS (EI) for $C_{26}H_{28}Cl_2F_3N_5O_3S$: 618 (MH$^+$).

The compound was converted into the hydrochloride salt by dissolving the oil in acetonitrile and adding 1N hydrochloric acid. The solution was lyopholized to give the hydrochloride salt as an off-white powder.

Example 6

Preparation of (S)-2-(3,4-dichlorophenyl)-N-(1-(3-(3,5-dimethylisoxazole-4-sulfonamido)phenyl)-2-(pyrrolidin-1-yl)ethyl)-N-methylacetamide, hydrochloride salt

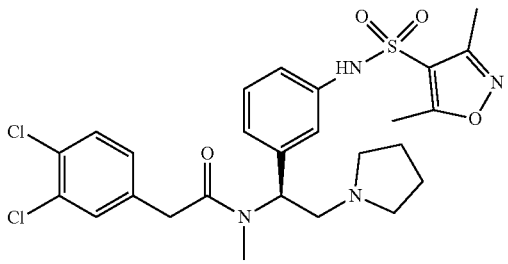 [SMILES: Cc1noc(C)c1S(=O)(=O)Nc1cccc([C@@H](CN2CCCC2)N(C)C(=O)Cc2ccc(Cl)c(Cl)c2)c1]

N-[(1S)-1-(3-Aminophenyl)-2-(pyrrolidin-1-yl)ethyl]-2-(3,4-dichlorophenyl)-N-methylacetamide (0.11 g, 0.23 mmol) (preparation described in Step 2 of Example 1) was dissolved in dichloromethane (4 mL) and anhydrous pyridine (0.14 mL, 1.72 mmol). To the cooled (0° C.) yellow solution there was added dropwise 3,5-dimethylisoxazole-4-sulfonyl chloride (0.11 g, 0.57 mmol) in dichloromethane (1 mL). The yellow reaction mixture was allowed to stir at 0° C., and the color turned orange. The reaction mixture was allowed to equilibrate to room temperature. After approximately 17 hours at room temperature, the reaction mixture was diluted with dichloromethane (25 mL) followed by the addition of water (30 mL). The aqueous portion was extracted with dichloromethane (2×15 mL). In five separate washing steps, the combined organic portions were washed in the following sequence: a 1N hydrochloric acid wash, a water wash, a saturated sodium bicarbonate wash, a second water wash and a brine wash (35 mL each). The organic portion was dried over anhydrous sodium sulfate, filtered, concentrated and purified by chromatography to give 0.077 g (59%) (S)-2-(3,4-dichlorophenyl)-N-(1-(3-(3,5-dimethylisoxazole-4-sulfonamido)phenyl)-2-(pyrrolidin-1-yl)ethyl)-N-methylacetamide as a yellow oil. ¹H NMR (500 MHz, CDCl₃): δ 6.93-7.30 (m, 7H), 5.92 (m, 1H), 3.75 (m, 1H), 3.59 (m, 1H), 3.10 (m, 1H), 2.67 (m, 4H), 2.50 (m, 1H), 2.39 (s, 3H), 2.17 (m, 3H), 1.73 (m, 4H); MS (EI) for $C_{26}H_{30}C_{12}N_4O_4S$: 565 (MH⁺).

The compound was converted into the hydrochloride salt by dissolving the oil in acetonitrile and adding 1N hydrochloric acid. The solution was lyopholized to give the hydrochloride salt as an off-white powder.

Example 7

Preparation of (S)-2-(3,4-dichlorophenyl)-N-(1-(3-((N-(2-methoxyethyl)-N-methylsulfamoyl)amino)phenyl)-2-(pyrrolidin-1-yl)ethyl)-N-methylacetamide, hydrochloride salt

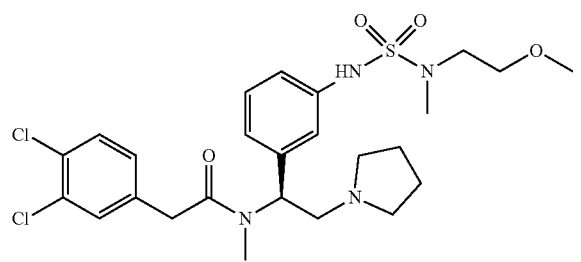 [SMILES: COCCN(C)S(=O)(=O)Nc1cccc([C@@H](CN2CCCC2)N(C)C(=O)Cc2ccc(Cl)c(Cl)c2)c1]

N-[(1S)-1-(3-Aminophenyl)-2-(pyrrolidin-1-yl)ethyl]-2-(3,4-dichlorophenyl)-N-methylacetamide (0.12 g, 0.25 mmol) (preparation described in Step 2 of Example 1) was dissolved in dioxane (5 mL) and 1N sodium hydroxide (0.77 mL, 1.92 mmol). To the cooled (0° C.) solution was added (2-methoxyethyl)(methyl)sulfamoyl chloride (0.12 g, 0.64 mmol), while maintaining the temperature less than 10° C. The yellow reaction mixture was allowed to stir at 0° C., and the color turned orange. The reaction mixture was allowed to equilibrate to room temperature. After approximately 17 hours at room temperature the reaction was diluted with dichloromethane followed by the addition of water. The aqueous portion was extracted with dichloromethane (3×). The organic portion was washed with water and saturated sodium chloride. The organic portion was dried over anhydrous sodium sulfate, filtered, concentrated and purified by chromatography to give 0.068 g (48%) of (S)-2-(3,4-dichlorophenyl)-N-(1-(3-((N-(2-methoxyethyl)-N-methylsulfamoyl)amino)phenyl)-2-(pyrrolidin-1-yl)ethyl)-N-methylacetamide as a yellow oil. ¹H NMR (500 MHz, CDCl₃): δ 6.95-7.30 (m, 7H), 6.01 (m, 1H), 3.71 (m, 1H), 3.61 (m, 1H), 3.47 (m, 3H), 3.41 (m, 3H), 3.31 (s, 3H), 2.80 (m, 4H), 2.74 (m, 4H), 2.45 (m, 2H), 1, 73 (m, 5H); MS (EI) for $C_{25}H_{34}C_{12}N_4O_4S$: 557 (MH⁺).

The compound was converted into the hydrochloride salt by dissolving the oil in acetonitrile and adding 1N hydrochloric acid. The solution was lyopholized to give the hydrochloride salt as an off-white powder.

Example 8

Preparation of 2-(3,4-dichlorophenyl)-N-((1S)-1-(3-(2-hydroxypropylsulfonamido)phenyl)-2-(pyrrolidin-1-yl)ethyl)-N-methylacetamide, hydrochloride salt

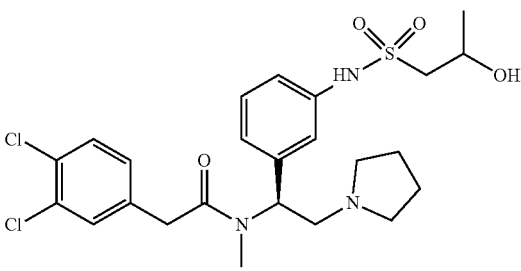 [SMILES: CC(O)CS(=O)(=O)Nc1cccc([C@@H](CN2CCCC2)N(C)C(=O)Cc2ccc(Cl)c(Cl)c2)c1]

Step 1: Preparation of N-((1S)-1-(3-(2-((tert-butyldimethylsilyl)oxy)propylsulfonamido)phenyl)-2-(pyrrolidin-1-yl)ethyl)-2-(3,4-dichlorophenyl)-N-methylacetamide

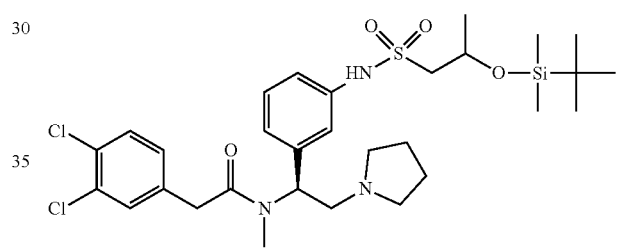

N-[(1S)-1-(3-Aminophenyl)-2-(pyrrolidin-1-yl)ethyl]-2-(3,4-dichlorophenyl)-N-methylacetamide (0.05 g, 0.10 mmol) (preparation described in Step 2 of Example 1) was dissolved in dichloromethane (1 mL) and anhydrous pyridine (63 μL, 0.78 mmol). To the cooled (0° C.) yellow solution there was added dropwise 2-((tert-butyldimethylsilyl)oxy)propane-1-sulfonyl chloride (0.07 g, 0.26 mmol) in dichloromethane (1 mL). The yellow reaction mixture was allowed to stir at 0° C., and the color turned orange. The reaction mixture was allowed to equilibrate to room temperature. After approximately 17 hours at room temperature, the reaction mixture was diluted with dichloromethane (25 mL) followed by the addition of water (30 mL). The aqueous portion was extracted with dichloromethane (2×15 mL). In five separate washing steps, the combined organic portions were washed in the following sequence: a 1N hydrochloric acid wash, a water wash, a saturated sodium bicarbonate wash, a second water wash and a brine wash (35 mL each). The organic portion was dried over anhydrous sodium sulfate, filtered, concentrated and purified by chromatography to give 0.04 g (60%) of N-((1S)-1-(3-(2-((tert-butyldimethylsilyl)oxy)propylsulfonamido)phenyl)-2-(pyrrolidin-1-yl)ethyl)-2-(3,4-dichlorophenyl)-N-methylacetamide as a yellow oil. MS (EI) for $C_{30}H_{45}C_{12}N_3O_4SSi$: 642 (MH⁺).

Step 2: Preparation of 2-(3,4-dichlorophenyl)-N-((1S)-1-(3-(2-hydroxypropylsulfonamido)phenyl)-2-(pyrrolidin-1-yl)ethyl)-N-methylacetamide, hydrochloride salt

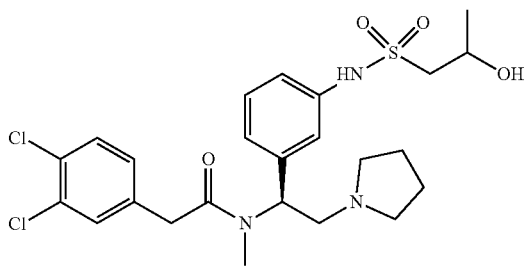 [SMILES: CC(O)CS(=O)(=O)Nc1cccc([C@@H](CN2CCCC2)N(C)C(=O)Cc2ccc(Cl)c(Cl)c2)c1]

To a solution of N-((1S)-1-(3-(2-((tert-butyldimethylsilyl)oxy)propylsulfonamido)phenyl)-2-(pyrrolidin-1-yl)ethyl)-2-(3,4-dichlorophenyl)-N-methylacetamide (0.040 g, 0.059 mmol) in THF (5 mL) at 0° C. was added tetra-N-butylammonium fluoride (0.17 mL, 0.17 mmol; 1 M in tetrahydrofuran). After approximately 17 hours at room temperature the tetrahydrofuran was removed under reduced pressure. The residue was purified by chromatography to give 0.024 g (77%) of 2-(3,4-dichlorophenyl)-N-((1S)-1-(3-(2-hydroxypropylsulfonamido)phenyl)-2-(pyrrolidin-1-yl)ethyl)-N-methylacetamide as a yellow oil. $^1$H NMR (500 MHz, CDCl$_3$): δ 6.94-7.30 (m, 7H), 5.96 (m, 1H), 4.32 (m, 1H), 3.75 (m, 1H), 3.62 (m, 1H), 2.98-3.25 (m, 3H), 2.80 (m, 2H), 2.72 (m, 4H), 2.58 (m, 2H), 2.45 (m, 1H), 1.75 (m, 3H), 1.60 (m, 1H), 1.34 (m, 1H), 1.15 (m, 3H); MS (EI) for C$_{24}$H$_{31}$C$_{12}$N$_3$O$_4$S: 528 (MH$^+$).

The compound was converted into the hydrochloride salt by dissolving the oil in acetonitrile and adding 1N hydrochloric acid. The solution was lyopholized to give the hydrochloride salt as an off-white powder.

Example 9

Preparation of (S)—N-(1-(3-((N,N-bis(2-methoxyethyl)sulfamoyl)amino)phenyl)-2-(pyrrolidin-1-yl)ethyl)-2-(3,4-dichlorophenyl)-N-methylacetamide, hydrochloride salt

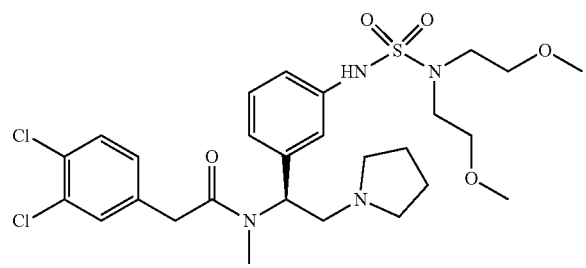 [SMILES: COCCN(CCOC)S(=O)(=O)Nc1cccc([C@@H](CN2CCCC2)N(C)C(=O)Cc2ccc(Cl)c(Cl)c2)c1]

N-[(1S)-1-(3-Aminophenyl)-2-(pyrrolidin-1-yl)ethyl]-2-(3,4-dichlorophenyl)-N-methylacetamide (0.12 g, 0.25 mmol) (preparation described in Step 2 of Example 1) was dissolved in dichloromethane (4 mL) and anhydrous pyridine (0.15 mL, 1.89 mmol). To the cooled (0° C.) yellow solution was added dropwise bis(2-methoxyethyl)sulfamoyl chloride (0.15 g, 0.63 mmol) in dichloromethane (1 mL). The yellow reaction mixture was allowed to stir at 0° C., and the color turned orange. The reaction mixture was allowed to equilibrate to room temperature. After approximately 17 hours at room temperature, the reaction mixture was diluted with dichloromethane (25 mL) followed by the addition of water (30 mL). The aqueous portion was extracted with dichloromethane (2×15 mL). In five separate washing steps, the combined organic portions were washed in the following sequence: a 1N hydrochloric acid wash, a water wash, a saturated sodium bicarbonate wash, a second water wash and a brine wash (35 mL each). The organic portion was dried over anhydrous sodium sulfate, filtered, concentrated and purified by chromatography to give 0.08 g (53%) of (S)—N-(1-(3-((N,N-bis(2-methoxyethyl)sulfamoyl)amino)phenyl)-2-(pyrrolidin-1-yl)ethyl)-2-(3,4-dichlorophenyl)-N-methylacetamide as a yellow oil. $^1$H NMR (500 MHz, CDCl$_3$): δ 7.05-7.38 (m, 7H), 6.10 (m, 1H), 3.80 (m, 1H), 3.72 (m, 1H), 3.58 (m, 6H), 3.41 (m, 5H), 2.75 (m, 2H), 2.52 (m, 1H), 1.77 (m, 2H), 1.61 (m, 12H); MS (EI) for C$_{27}$H$_{38}$C$_{12}$N$_4$O$_5$S: 601 (MH$^+$).

The compound was converted into the hydrochloride salt by dissolving the oil in acetonitrile and adding 1N hydrochloric acid. The solution was lyopholized to give the hydrochloride salt as an off-white powder.

Example 10

Preparation of (S)-2-(3,4-dichlorophenyl)-N-(1-(3-(4,5-dichlorothiophene-2-sulfonamido)phenyl)-2-(pyrrolidin-1-yl)ethyl)-N-methylacetamide, hydrochloride salt

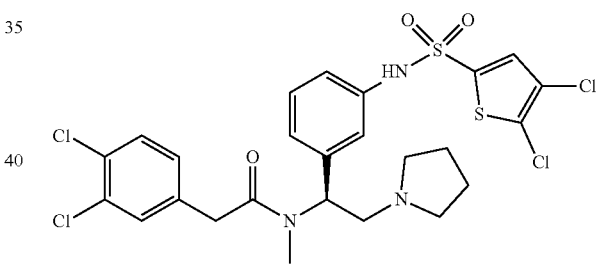

N-[(1S)-1-(3-Aminophenyl)-2-(pyrrolidin-1-yl)ethyl]-2-(3,4-dichlorophenyl)-N-methylacetamide (0.12 g, 0.25 mmol) (preparation described in Step 2 of Example 1) was dissolved in dichloromethane (4 mL) and anhydrous pyridine (0.16 mL, 1.98 mmol). To the cooled (0° C.) yellow solution there was added dropwise 4,5-dichlorothiophene-2-sulfonyl chloride (0.17 g, 0.66 mmol) in dichloromethane (1 mL). The yellow reaction mixture was allowed to stir at 0° C., and the color turned orange. The reaction mixture was allowed to equilibrate to room temperature. After approximately 17 hours at room temperature, the reaction mixture was diluted with dichloromethane (25 mL) followed by the addition of water (30 mL). The aqueous portion was extracted with dichloromethane (2×15 mL). In five separate washing steps, the combined organic portions were washed in the following sequence: a 1N hydrochloric acid wash, a water wash, a saturated sodium bicarbonate wash, a second water wash and a brine wash (35 mL each). The organic portion was dried over anhydrous sodium sulfate, filtered, concentrated and purified by chromatography to give 0.10 g (60%) of (S)-2-(3,4-dichlorophenyl)-N-(1-(3-(4,5-dichlorothiophene-2-sulfonamido)phenyl)-2-(pyrrolidin-1-yl)ethyl)-

N-methylacetamide s a yellow oil. $^1$H NMR (500 MHz, CDCl$_3$): δ 6.93-7.31 (m, 8H), 5.96 (m, 1H), 3.62-3.70 (m, 3H), 3.12 (m, 1H), 2.71 (m, 3H), 2.63 (m, 3H), 2.51 (m, 2H), 1.72 (m, 4H); MS (EI) for C$_{25}$H$_{25}$C$_{14}$N$_3$O$_3$S$_2$: 622 (MH$^+$).

The compound was converted into the hydrochloride salt by dissolving the oil in acetonitrile and adding 1N hydrochloric acid. The solution was lyopholized to give the hydrochloride salt as an off-white powder.

Example 11

Preparation of (S)—N-methyl-2,2-diphenyl-N-(2-(pyrrolidin-1-yl)-1-(3-(2-(2,2,2-trifluoroethoxy)ethylsulfonamido)phenyl)ethyl)acetamide, hydrochloride salt

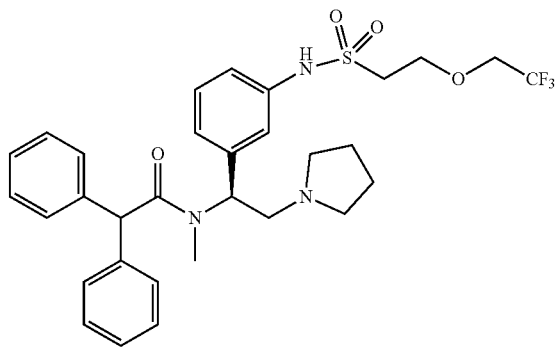 [SMILES: CN(C(=O)C(c1ccccc1)c1ccccc1)[C@H](CN1CCCC1)c1cccc(NS(=O)(=O)CCOCC(F)(F)F)c1]

N-[(1S)-1-(3-Aminophenyl)-2-(pyrrolidin-1-yl)ethyl]-2-(3,4-dichlorophenyl)-N-methylacetamide (0.14 g, 0.35 mmol) (preparation described in Step 2 of Example 1) was dissolved in dichloromethane (6 mL) and anhydrous pyridine (0.21 mL, 2.65 mmol). To the cooled (0° C.) yellow solution there was added dropwise 2-(2,2,2-trifluoroethoxy) ethanesulfonyl chloride (0.21 g, 0.88 mmol) in dichloromethane (1 mL). The yellow reaction mixture was allowed to stir at 0° C., and the color turned orange. The reaction mixture was allowed to equilibrate to room temperature. After approximately 17 hours at room temperature, the reaction mixture was diluted with dichloromethane (25 mL) followed by the addition of water (30 mL). The aqueous portion was extracted with dichloromethane (2×15 mL). In five separate washing steps, the combined organic portions were washed in the following sequence: a 1N hydrochloric acid wash, a water wash, a saturated sodium bicarbonate wash, a second water wash and a brine wash (35 mL each). The organic portion was dried over anhydrous sodium sulfate, filtered, concentrated and purified by chromatography to give 0.16 g (77%) of ((S)—N-methyl-2,2-diphenyl-N-(2-(pyrrolidin-1-yl)-1-(3-(2-(2,2,2-trifluoroethoxy)ethylsulfonamido)phenyl)ethyl)acetamide as a yellow oil. $^1$H NMR (500 MHz, CDCl$_3$): δ 7.12-7.30 (m, 14H), 6.21 (m, 1H), 3.85-3.97 (m, 4H), 3.20 (m, 2H), 2.78 (m, 4H), 2.25 (m, 1H), 2.15 (m, 1H), 1.95 (m, 2H), 1.54 (m, 7H); MS (EI) for C$_{31}$H$_{36}$F$_3$N$_3$O$_4$S: 604 (MH$^+$).

The compound was converted into the hydrochloride salt by dissolving the oil in acetonitrile and adding 1N hydrochloric acid. The solution was lyopholized to give the hydrochloride salt as an off-white powder.

Example 12

Preparation of N-((1S)-1-(3-(2-hydroxypropylsulfonamido)phenyl)-2-(pyrrolidin-1-yl)ethyl)-N-methyl-2,2-diphenylacetamide, hydrochloride salt

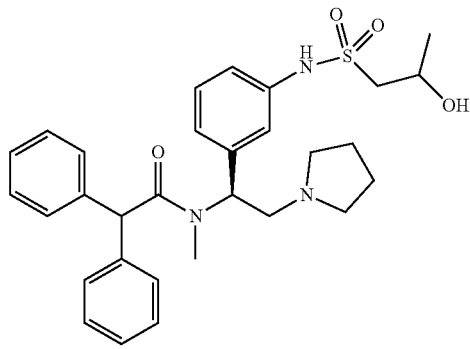 [SMILES: CC(O)CS(=O)(=O)Nc1cccc([C@@H](CN2CCCC2)N(C)C(=O)C(c2ccccc2)c2ccccc2)c1]

Step 1: Preparation of (S)—N-methyl-N-(1-(3-nitrophenyl)-2-(pyrrolidin-1-yl)ethyl)-2,2-diphenylacetamide

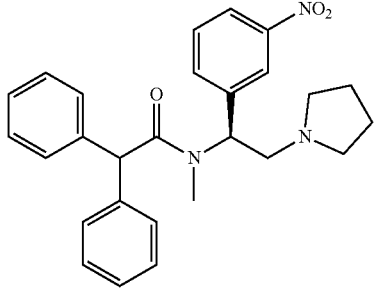

(S)-1-[2-(Methylamino)-2-(3/4-nitrophenyl)ethyl]pyrroldin (0.31 g, 1.25 mmol) [Portoghese (1994) *Journal of Medicinal Chemistry* 37:4490-4498] was dissolved in anhydrous dichloromethane (6 mL). The dark solution was stirred at 0° C., under nitrogen, followed by the addition of diisopropylethylamine (0.44 mL, 2.52 mmol), and 2,2-diphenylacetyl chloride (0.35 g, 1.38 mmol). The reaction mixture was allowed to equilibrate to room temperature. After approximately 17 hours at room temperature the mixture was concentrated under reduced pressure. The residue was dissolved in ethyl acetate (8 mL) and was washed with saturated sodium bicarbonate (2×15 mL) and saturated sodium chloride (15 mL). The combined organic portion was dried over anhydrous sodium sulfate, filtered and concentrated under reduced pressure. The residue was purified by chromatography to give 0.51 g (86%) of (S)—N-methyl-N-(1-(3-nitrophenyl)-2-(pyrrolidin-1-yl)ethyl)-2,2-diphenylacetamide as a yellow oil. MS (EI) for C$_{22}$H$_{24}$F$_3$N$_3$O$_3$: 436 (MH$^+$).

Step 2: Preparation of (S)—N-(1-(3-aminophenyl)-2-(pyrrolidin-1-yl)ethyl)-N-methyl-2,2-diphenylacetamide

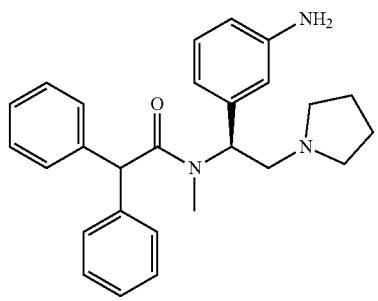 [SMILES: CN(C(=O)C(c1ccccc1)c1ccccc1)[C@H](CN1CCCC1)c1cccc([N+](=O)[O-])c1]

A mixture of (S)—N-methyl-N-(1-(3-nitrophenyl)-2-(pyrrolidin-1-yl)ethyl)-2,2-diphenylacetamide (0.40 g, 0.90 mmol), hydrazine hydrate (0.69 g, 10.8 mmol) and Raney nickel slurry (2.0 mL) in 95% ethanol (45 mL) was heated to 55° C. After approximately two hours at 55° C. the reaction was complete as indicated by LC-MS. The reaction mixture was filtered through Celite, and the Raney nickel was washed with hot methanol. The filtrate was concentrated under reduced pressure, and the residue was purified by chromatography to give 0.21 g (44%) of (S)—N-(1-(3-aminophenyl)-2-(pyrrolidin-1-yl)ethyl)-N-methyl-2,2-diphenylacetamide as a light-yellow oil. MS (EI) for $C_{27}H_{31}N_3O$: 414 (MH+).

Step 3: Preparation of N-((1S)-1-(3-(2-((tert-butyldimethylsilyl)oxy)propylsulfonamido)phenyl)-2-(pyrrolidin-1-yl)ethyl)-N-methyl-2,2-diphenylacetamide

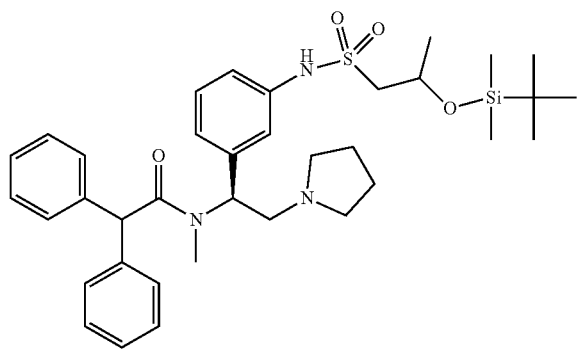 [SMILES: CC(CS(=O)(=O)Nc1cccc([C@@H](CN2CCCC2)N(C)C(=O)C(c2ccccc2)c2ccccc2)c1)O[Si](C)(C)C(C)(C)C]

N-[(1S)-1-(3-Aminophenyl)-2-(pyrrolidin-1-yl)ethyl]-2-(3,4-dichlorophenyl)-N-methylacetamide (0.16 g, 0.38 mmol) (preparation described in Step 2 of Example 1) was dissolved in dichloromethane (7 mL) and anhydrous pyridine (0.23 mL, 2.90 mmol). To the cooled (0° C.) yellow solution there was added dropwise 2-((tert-butyldimethylsilyl)oxy)propane-1-sulfonyl chloride (0.27 g, 0.96 mmol) in dichloromethane (1 mL). The yellow reaction mixture was allowed to stir at 0° C., and the color turned orange. The reaction mixture was allowed to equilibrate to room temperature. After approximately 17 hours at room temperature, the reaction mixture was diluted with dichloromethane (25 mL) followed by the addition of water (30 mL). The aqueous portion was extracted with dichloromethane (2×15 mL). In five separate washing steps, the combined organic portions were washed in the following sequence: a 1N hydrochloric acid wash, a water wash, a saturated sodium bicarbonate wash, a second water wash and a brine wash (35 mL each). The organic portion was dried over anhydrous sodium sulfate, filtered, concentrated and purified by chromatography to give 0.19 g (76%) of N-((1S)-1-(3-(2-((tert-butyldimethylsilyl)oxy)propylsulfonamido)phenyl)-2-(pyrrolidin-1-yl)ethyl)-N-methyl-2,2-diphenylacetamide as a yellow oil. MS (EI) for $C_{36}H_{51}N_3O_4SSi$: 650 (MH+).

Step 4: Preparation of N-((1S)-1-(3-(2-hydroxypropylsulfonamido)phenyl)-2-(pyrrolidin-1-yl)ethyl)-N-methyl-2,2-diphenylacetamide, hydrochloride salt

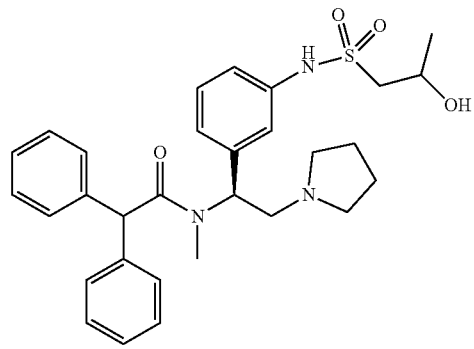 [SMILES: CC(O)CS(=O)(=O)Nc1cccc([C@@H](CN2CCCC2)N(C)C(=O)C(c2ccccc2)c2ccccc2)c1]

To a solution of N-((1S)-1-(3-(2-((tert-butyldimethylsilyl)oxy)propylsulfonamido)phenyl)-2-(pyrrolidin-1-yl)ethyl)-N-methyl-2,2-diphenylacetamide (0.19 g, 0.29 mmol) in THF (6 mL) at 0° C. was added tetra-N-butylammonium fluoride (0.87 mL, 0.87 mmol; 1 M in tetrahydrofuran). After approximately 17 hours at room temperature the tetrahydrofuran was removed under reduced pressure. The residue was purified by chromatography to give 0.13 g (85%) of N-((1S)-1-(3-(2-hydroxypropylsulfonamido)phenyl)-2-(pyrrolidin-1-yl)ethyl)-N-methyl-2,2-diphenylacetamide as a yellow oil. $^1$H NMR (500 MHz, CDCl$_3$): δ 7.09-7.37 (m, 14H), 6.09 (m, 1H), 4.37 (m, 1H), 3.07-3.23 (m, 5H), 2.63-2.90 (m, 6H), 2.45 (m, 2H), 1.80 (m, 4H), 1.25 (m, 4H); MS (EI) for $C_{30}H_{37}N_3O_4S$: 536 (MH+).

The compound was converted into the hydrochloride salt by dissolving the oil in acetonitrile and adding 1N hydrochloric acid. The solution was lyopholized to give the hydrochloride salt as an off-white powder.

Example 13

Preparation of N-((1S)-1-(3-(2-hydroxypropylsulfonamido)phenyl)-2-(pyrrolidin-1-yl)ethyl)-N-methyl-2-(4-(trifluoromethyl)phenyl)acetamide, hydrochloride salt

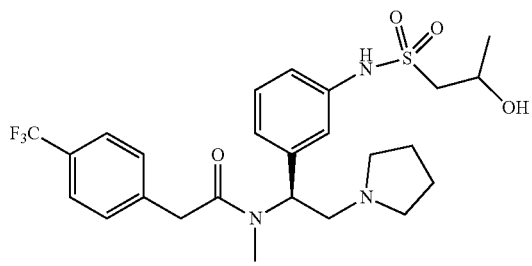 [SMILES: CC(O)CS(=O)(=O)Nc1cccc([C@@H](CN2CCCC2)N(C)C(=O)Cc2ccc(C(F)(F)F)cc2)c1]

Step 1: Preparation of (S)—N-methyl-N-(1-(3-nitrophenyl)-2-(pyrrolidin-1-yl)ethyl)-2-(4-(trifluoromethyl)phenyl)acetamide

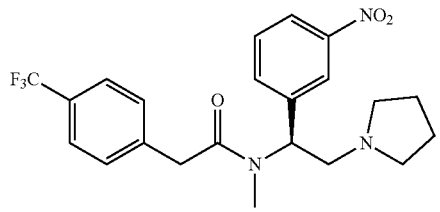

(S)-1-[2-(Methylamino)-2-(3/4-nitrophenyl)ethyl]pyrrolidin (0.34 g, 1.38 mmol) [Portoghese (1994) *Journal of Medicinal Chemistry* 37:4490-4498] was dissolved in anhydrous acetonitrile (7 mL). The dark solution was stirred at 0° C., under nitrogen, followed by the addition of diisopropylethylamine (0.54 mL, 3.04 mmol), 2-(4-(trifluoromethyl)phenyl)acetic acid (0.31 g, 1.52 mmol), and O-(benzotriazol-1-yl)-N,N,N',N'-tetramethyluronium tetrafluoroborate (0.50 g, 1.52 mmol). The reaction mixture was allowed to equilibrate to room temperature. After approximately 17 hours at room temperature the mixture was concentrated under reduced pressure. The residue was dissolved in ethyl acetate (8 mL) and was washed with saturated sodium bicarbonate (2×15 mL) and saturated sodium chloride (15 mL). The combined organic portion was dried over anhydrous sodium sulfate, filtered and concentrated under reduced pressure. The residue was purified by chromatography to give 0.51 g (86%) of (S)—N-methyl-N-(1-(3-nitrophenyl)-2-(pyrrolidin-1-yl)ethyl)-2-(4-(trifluoromethyl)phenyl)acetamide as a yellow oil. MS (EI) for $C_{22}H_{24}F_3N_3O_3$: 436 (MH$^+$).

Step 2: Preparation of (S)—N-(1-(3-aminophenyl)-2-(pyrrolidin-1-yl)ethyl)-N-methyl-2-(4-(trifluoromethyl)phenyl)acetamide

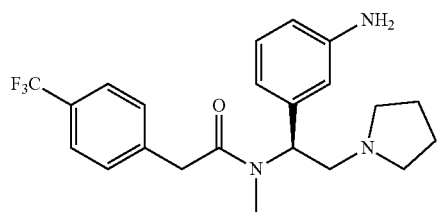 [SMILES: CN(C(=O)Cc1ccc(C(F)(F)F)cc1)[C@H](CN1CCCC1)c1cccc([N+](=O)[O-])c1]

A mixture of (S)—N-methyl-N-(1-(3-nitrophenyl)-2-(pyrrolidin-1-yl)ethyl)-2-(4-(trifluoromethyl)phenyl)acetamide (0.51 g, 1.18 mmol), hydrazine hydrate (0.70 g, 11 mmol) and Raney nickel slurry (2.5 mL) in 95% ethanol (45 mL) was heated to 55° C. After approximately two hours at 55° C. the reaction was complete as indicated by LC-MS. The reaction mixture was filtered through Celite, and the Raney nickel was washed with hot methanol. The filtrate was concentrated under reduced pressure, and the residue was purified by chromatography to give 0.21 g (44%) of (S)—N-(1-(3-aminophenyl)-2-(pyrrolidin-1-yl)ethyl)-N-methyl-2-(4-(trifluoromethyl)phenyl)acetamide as a light-yellow oil. MS (EI) for $C_{22}H_{26}F_3N_3O$: 406 (MH$^+$).

Step 3: Preparation of N-((1S)-1-(3-(2-((tert-butyldimethylsilyl)oxy)propylsulfonamido)phenyl)-2-(pyrrolidin-1-yl)ethyl)-N-methyl-2-(4-(trifluoromethyl)phenyl)acetamide

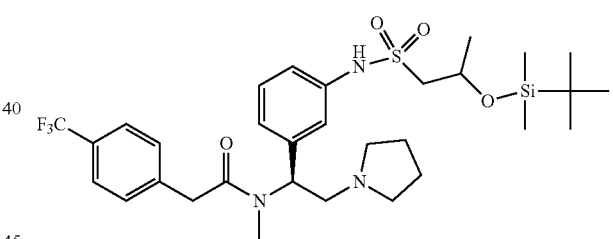

(S)—N-(1-(3-aminophenyl)-2-(pyrrolidin-1-yl)ethyl)-N-methyl-2-(4-(trifluoromethyl)phenyl)acetamide (0.12 g, 0.30 mmol) was dissolved in dichloromethane (5 mL) and anhydrous pyridine (0.18 mL, 2.31 mmol). To the cooled (0° C.) yellow solution there was added dropwise 2-((tert-butyldimethylsilyl)oxy)propane-1-sulfonyl chloride (0.22 g, 0.77 mmol) in dichloromethane (1 mL). The yellow reaction mixture was allowed to stir at 0° C., and the color turned orange. The reaction mixture was allowed to equilibrate to room temperature. After approximately 17 hours at room temperature, the reaction mixture was diluted with dichloromethane (25 mL) followed by the addition of water (30 mL). The aqueous portion was extracted with dichloromethane (2×15 mL). In five separate washing steps, the combined organic portions were washed in the following sequence: a 1N hydrochloric acid wash, a water wash, a saturated sodium bicarbonate wash, a second water wash and a brine wash (35 mL each). The organic portion was dried over anhydrous sodium sulfate, filtered, concentrated and purified by chromatography to give 0.14 g (72%) of N-((1S)-1-(3-(2-((tert-butyldimethylsilyl)oxy)propylsulfonamido)phenyl)-2-(pyrrolidin-1-yl)ethyl)-N-methyl-2-(4-(trifluoromethyl)phenyl)acetamide as a yellow oil. MS (EI) for $C_{31}H_{46}F_3N_3O_4SSi$: 642 (MH+).

Step 4: Preparation of N-((1S)-1-(3-(2-hydroxypropylsulfonamido)phenyl)-2-(pyrrolidin-1-yl)ethyl)-N-methyl-2-(4-(trifluoromethyl)phenyl)acetamide, hydrochloride salt

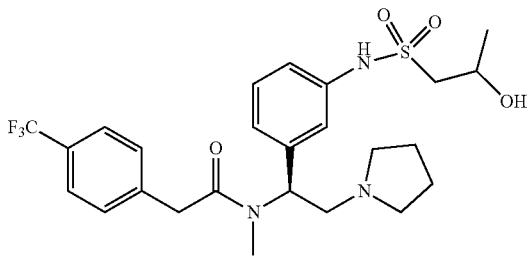 [SMILES: CC(O)CS(=O)(=O)Nc1cccc([C@@H](CN2CCCC2)N(C)C(=O)Cc2ccc(C(F)(F)F)cc2)c1]

To a solution of N-((1S)-1-(3-(2-((tert-butyldimethylsilyl)oxy)propylsulfonamido)phenyl)-2-(pyrrolidin-1-yl)ethyl)-N-methyl-2-(4-(trifluoromethyl)phenyl)acetamide (0.10 g, 0.15 mmol) in tetrahydrofuran (8 mL) at 0° C. was added tetra-N-butylammonium fluoride (0.46 mL, 0.46 mmol; 1 M in tetrahydrofuran). After approximately 17 hours at room temperature the tetrahydrofuran was removed under reduced pressure. The residue was purified by chromatography to give 0.056 g (68%) of N-((1S)-1-(3-(2-hydroxypropylsulfonamido)phenyl)-2-(pyrrolidin-1-yl)ethyl)-N-methyl-2-(4-(trifluoromethyl)phenyl)acetamide as a yellow oil. $^1$H NMR (500 MHz, CDCl$_3$): δ 7.07-7.55 (m, 8H), 6.05 (m, 1H), 4.40 (m, 1H), 3.79-3.93 (m, 2H), 3.22 (m, 2H), 3.03-3.15 (m, 2H), 2.90 (m, 1H), 2.76 (s, 3H), 2.61 (m, 2H), 1.79 (m, 3H), 1.65 (m, 2H), 1.40 m, 2H), 1.22 (m, 3H); MS (EI) for $C_{25}H_{32}F_3N_3O_4S$: 528 (MH+).

The compound was converted into the hydrochloride salt by dissolving the oil in acetonitrile and adding 1N hydrochloric acid. The solution was lyopholized to give the hydrochloride salt as an off-white powder.

Example 14

Preparation of 2-(3,4-dichlorophenyl)-N—((S)-2-((R)-3-hydroxypyrrolidin-1-yl)-1-phenylethyl)-N-methylacetamide

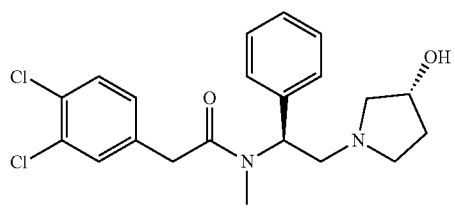 [SMILES: CN(C(=O)Cc1ccc(Cl)c(Cl)c1)[C@H](CN1CC[C@@H](O)C1)c1ccccc1]

Step 1: Preparation of benzyl ((S)-2-((R)-3-hydroxypyrrolidin-1-yl)-2-oxo-1-phenylethyl)carbamate A solution of (S)-2-(((benzyloxy)carbonyl)amino)-2-phenylacetic acid (2.78 g, 9.75 mmol), (R)-pyrrolidin-3-ol hydrochloride (1.23 g, 9.75 mmol) and diisopropylethylamine (5.56 mL, 31.2 mmol) was stirred at room temperature for fifteen minutes and then cooled to 0° C. O-(Benzotriazol-1-yl)-N,N,N',N'-tetramethyluronium tetrafluoroborate (3.87 g, 11.70 mmol) was added and the light-brown reaction mixture was stirred at 0° C. for one hour, and then equilibrated to room temperature. After approximately 17 hours at room temperature the orange mixture was concentrated under reduced pressure. The residue was purified by chromatography to give 1.80 g (52%) of benzyl ((S)-2-((R)-3-hydroxypyrrolidin-1-yl)-2-oxo-1-phenylethyl)carbamate as a clear oil. MS (EI) for $C_{20}H_{22}N_2O_4$: 355 (MH+).

Step 2: Preparation of (R)-1-((S)-2-(methylamino)-2-phenylethyl)pyrrolidin-3-ol

Benzyl ((S)-2-((R)-3-hydroxypyrrolidin-1-yl)-2-oxo-1-phenylethyl)carbamate (1.80 g, 5.08 mmol) was dissolved in anhydrous tetrahydrofuran (75 mL) and cooled to 0° C. To the clear solution was added lithium aluminum hydride (2 M in THF, 5.0 mL, 10.16 mmol) carefully. The cloudy reaction mixture was heated to reflux (oil bath at 70° C.) for two hours, and then allowed to equilibrate to room temperature. After approximately 18 hours at room temperature the mixture was cooled with an ice bath. The excess lithium aluminum hydride was quenched with ethyl acetate (25 μL), followed by the addition of water (250 μL), and then followed by the addition of 4N sodium hydroxide (250 μL). After five minutes water (755 μL) was added and followed by stirring for fifteen minutes. A white precipitate was filtered and the filtrate dried over anhydrous sodium sulfate. After filtration the filtrate was concentrated under reduced pressure. The residue was purified by chromatography to give 0.95 g (85%) of (R)-1-((S)-2-(methylamino)-2-phenylethyl)pyrrolidin-3-ol as a light-yellow oil. $^1$H NMR (500 MHz, CDCl$_3$): δ 7.30-7.33 (m, 5H), 4.34 (m, 1H), 3.58 (m, 1H), 3.42 (m, 2H), 2.79-2.86 (m, 3H), 2.49 (m, 1H), 2.33-2.40 (m, 2H), 2.27 (s, 3H), 2.17 (m, 1H), 1.75 (m, 1H)); MS (EI) for $C_{13}H_{20}N_2O$: 221 (MH+).

Step 3: Preparation of 2-(3,4-dichlorophenyl)-N—((S)-2-((R)-3-hydroxypyrrolidin-1-yl)-1-phenyl-ethyl)-N-methylacetamide

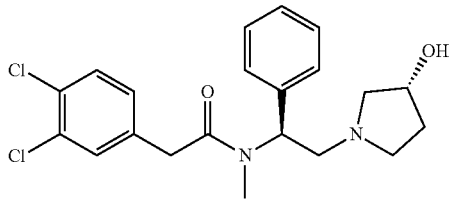 [SMILES: CN(C(=O)Cc1ccc(Cl)c(Cl)c1)[C@H](CN1CC[C@@H](O)C1)c1ccccc1]

To a stirring solution of (R)-1-((S)-2-(methylamino)-2-phenylethyl)pyrrolidin-3-ol (0.21 g, 0.97 mmol) in dry acetonitrile (5 mL; 0.20M), under nitrogen, was added diisopropylethylamine (0.52 mL, 2.93 mmol) and 3,4-dichlorophenylacetic acid (0.20 g, 0.97 mmol). The light-yellow solution was cooled to 0° C. and O-(benzotriazol-1-yl)-N,N,N',N'-tetramethyluronium tetrafluoroborate (0.38 g, 1.17 mmol) was added. The light-yellow reaction mixture was allowed to equilibrate to room temperature, and stirred under nitrogen. After approximately 17 hours at room temperature, the yellow mixture was concentrated under reduced pressure. The yellow oil was taken up in ethyl acetate and washed with 10% ammonium chloride, saturated sodium bicarbonate and saturated sodium chloride. The organic portion was dried over anhydrous sodium sulfate, filtered and concentrated under reduced pressure. The residue was purified by chromatography to give 0.26 g (65%) of 2-(3,4-dichlorophenyl)-N—((S)-2-((R)-3-hydroxypyrrolidin-1-yl)-1-phenylethyl)-N-methylacetamide as a light-yellow oil. $^1$H NMR (500 MHz, CDCl$_3$): δ 7.17-7.43 (m, 8H), 6.12 (m, 1H), 4.36 (m, 1H), 3.71-3.82 (m, 2H), 3.19 (m, 1H), 2.87-2.98 (m, 2H), 2.71 (s, 3H), 2.57 (m, 2H), 2.17 (m, 1H), 1.77 (m, 1H)); MS (EI) for C$_{21}$H$_{24}$C$_{12}$N$_2$O$_2$: 407 (MH$^+$).

Example 15

Preparation of 2-(2,4-Difluorophenyl)-N-{(1S)-1-[4-(2-hydroxyethoxy)phenyl]-2-[(3S)-3-hydroxypyrrolidin-1-yl]ethyl}-N-methylacetamide, hydrochloride salt Using the synthetic approach schematically outlined below, 2-(2,4-difluorophenyl)-N-{(1)-1-[4-(2-hydroxyethoxy)phenyl]-2-[(3S)-3-hydroxypyrrolidin-1-yl]ethyl}-N-methylacetamide, hydrochloride salt was prepared.

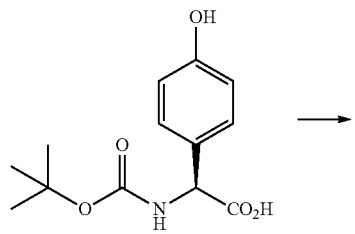

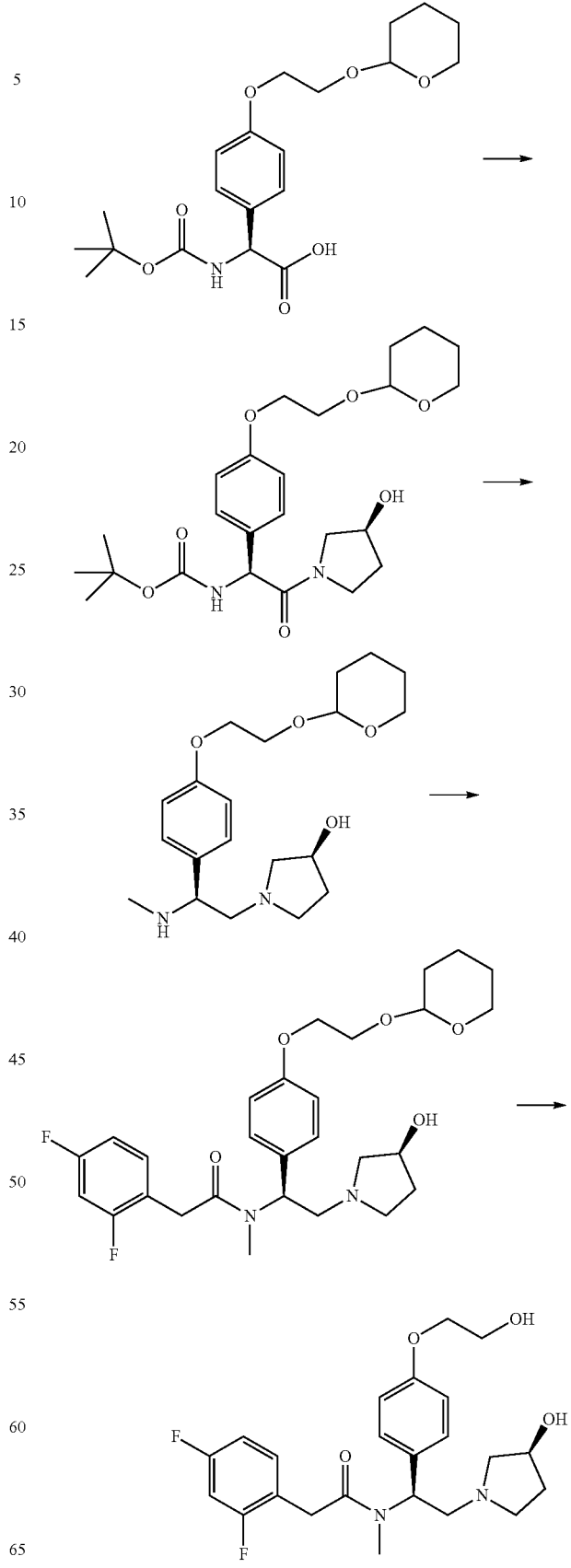

Step 1: Preparation of (2S)-2-((tert-butoxycarbonyl)amino)-2-(4-(2-((tetrahydro-2H-pyran-2-yl)oxy)ethoxy)phenyl)acetic acid

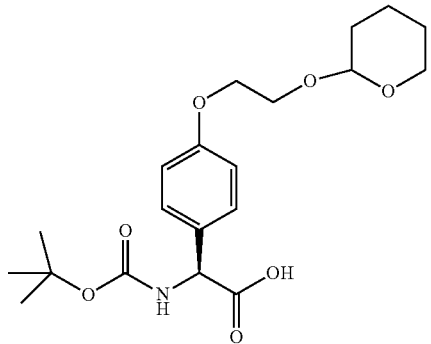 [SMILES: CC(C)(C)OC(=O)N[C@H](C(=O)O)c1ccc(OCCOC2CCCCO2)cc1]

(S)-2-((tert-butoxycarbonyl)amino)-2-(4-hydroxyphenyl) acetic acid (2.67 g, 10.0 mmol) was dissolved in 70 mL of dimethylformamide and the solution was cooled in an ice bath. Sodium hydride (0.88 g, 60% in mineral oil, 22.0 mmol) was added in portions. The mixture was stirred for thirty minutes before 2-(2-bromoethoxy)tetrahydro-2H-pyran (2.30 g, 11.0 mmol) in 30 mL of dimethylformamide was added portionally. The reaction mixture was stirred at room temperature for 17 hours and then diluted with ice/water. The mixture was extracted with ethyl acetate (50 mL×2). The aqueous layer was cooled in an ice bath and acidified using 1.5 M aqueous potassium hydrogen sulfate to pH 2-3. The resulting mixture was extracted with ethyl acetate (100 mL×2). The organic phase was washed with water, brine, and then dried over sodium sulfate. The product (3.3 g) was obtained after removing the solvent and drying under high vacuum (yield: 84%). $^1$H NMR (500 MHz, CDCl$_3$): δ 7.32 (m, 2H), 6.92 (m, 2H), 5.55 (m, 0.5H), 5.28 (m, 0.5H), 4.74 (m, 1H), 4.15 (m, 2H), 4.05 (m, 1H), 3.90 (m, 1H), 3.85 (m, 1H), 3.55 (m, 1H), 1.85 (m, 1H), 1.75 (m, 1H), 1.60 (m, 5H), 1.45 (s, 5H), 1.28 (s, 4H); MS (EI) for C$_{20}$H$_{29}$NO$_7$; 394 (MH$^-$).

Step 2: Preparation of tert-butyl ((1S)-2-((S)-3-hydroxypyrrolidin-1-yl)-2-oxo-1-(4-(2-((tetrahydro-2H-pyran-2-yl)oxy)ethoxy)phenyl)ethyl)carbamate

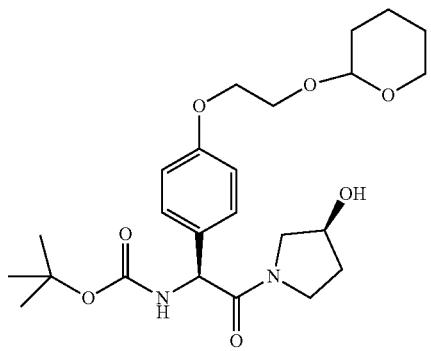 [SMILES: CC(C)(C)OC(=O)N[C@H](C(=O)N1CC[C@H](O)C1)c1ccc(OCCOC2CCCCO2)cc1]

(2S)-2-((Tert-butoxycarbonyl)amino)-2-(4-(2-((tetrahydro-2H-pyran-2-yl)oxy)ethoxy)phenyl)acetic acid (3.20 g, 8.09 mmol), (s)-pyrrolidin-3-ol (0.78 g, 8.90 mmol), and N,N-diisopropylethylamine (2.07 g, 16.18 mmol) were dissolved in 18 mL of acetonitrile. The mixture was stirred for ten minutes at room temperature and then cooled to 0° C. O-(Benzotriazol-1-yl)-N,N,N',N'-tetramethyluronium tetrafluoroborate (3.12 g, 9.71 mmol) was added into the solution. The reaction mixture was stirred for two hours under an ice bath and then warmed to room temperature for four hours. Dichloromethane (200 mL) was added into the reaction mixture, and the resulting solution was washed with water (200 mL×3). The solution was dried over sodium sulfate and concentrated. The product was obtained after drying under vacuum (3.40 g, yield: 90%). $^1$H NMR (500 MHz, CDCl$_3$): δ 7.30 (m, 2H), 6.90 (m, 2H), 5.96 (dd, 1H), 5.30 (dd, 1H), 4.70 (m, 1H), 4.45 (m, 1H), 4.15 (m, 1H), 4.05 (m, 1H), 3.90 (m, 1H), 3.80 (m, 1H), 3.70 (m, 2H), 3.55 (m, 2H), 3.35 (m, 0.5H), 3.10 (m, 0.5H), 1.96 (m, 1H), 1.85 (m, 2H), 1.75 (m, 1H), 1.60 (m, 2H), 1.55 (m, 3H), 1.40 (s, 9H); MS (EI) for C$_{24}$H$_{36}$N$_2$O$_7$; 465 (MH$^+$).

Step 3: Preparation of (3S)-1-((2S)-2-(methylamino)-2-(4-(2-((tetrahydro-2H-pyran-2-yl)oxy)ethoxy)phenyl)ethyl)pyrrolidin-3-ol

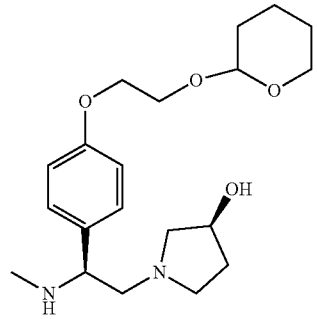 [SMILES: CN[C@H](CN1CC[C@H](O)C1)c1ccc(OCCOC2CCCCO2)cc1]

Tert-butyl ((1S)-2-((S)-3-hydroxypyrrolidin-1-yl)-2-oxo-1-(4-(2-((tetrahydro-2H-pyran-2-yl)oxy)ethoxy)phenyl)ethyl)carbamate (1.33 g, 2.85 mmol) was dissolved in tetrahydrofuran (20 mL). A 2.0 M lithium aluminum hydride solution (8.0 mL, 16 mmol) was added into the solution at room temperature. The mixture was stirred at 65° C. for four hours. Sodium carbonate (3N solution) was cautiously added until effervescence ceased. Ethyl acetate (100 mL) was added into the mixture. The solid was filtered out and washed with ethyl acetate (100 mL). The filtrate was washed with saturated sodium chloride solution and dried over sodium sulfate. The product was obtained after removing solvent (0.84 g, yield: 71%). $^1$H NMR (500 MHz, CDCl$_3$): δ 7.28 (m, 2H), 6.92 (m, 2H), 4.74 (m, 1H), 4.34 (m, 1H), 4.16 (m, 2H), 4.06 (m, 1H), 3.92 (m, 1H), 3.84 (m, 1H), 3.55 (m, 2H), 3.02 (m, 1H), 2.85 (m, 1H), 2.65 (m, 2H), 2.30 (m, 3H), 2.20 (m, 2H), 1.80 (m, 4H), 1.60 (m, 5H); MS (EI) for C$_{20}$H$_{32}$N$_2$O$_4$; 365 (MH$^+$).

Step 4: Preparation of 2-(2,4-difluorophenyl)-N-{(1S)-1-[4-(2-hydroxyethoxy)phenyl]-2-[(3S)-3-hydroxypyrrolidin-1-yl]ethyl}-N-methylacetamide, hydrochloride salt

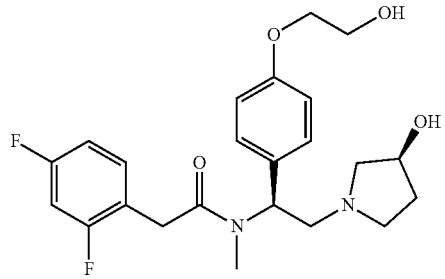 [SMILES: CN(C(=O)Cc1ccc(F)cc1F)[C@H](CN1CC[C@H](O)C1)c1ccc(OCCO)cc1]

(3S)-1-((2S)-2-(methylamino)-2-(4-(2-((tetrahydro-2H-pyran-2-yl)oxy)ethoxy)phenyl)ethyl)pyrrolidin-3-ol (0.073 g, 0.20 mmol), 2-(2,4-difluorophenyl)acetic acid (0.034 g, 0.20 mmol), and N,N-diisopropylethylamine (0.051 g, 0.40 mmol) were dissolved in 3 mL of acetonitrile. The mixture was stirred for ten minutes at room temperature and then cooled to 0° C. O-(Benzotriazol-1-yl)-N,N,N',N'-tetramethyluronium tetrafluoroborate (0.077 g, 0.24 mmol) was added into the solution. The reaction mixture was stirred for three hours under an ice-bath. Dichloromethane (150 mL) was added into the reaction mixture and the resultant solution was washed with water and dried over sodium sulfate. Evaporation of the solvent and purification of the residue by flash chromatography yielded product (0.091 g, 0.18 mmol). The product was dissolved in 10 mL of methanol and then 4-methylbenzenesulfonic acid (0.060 g, 0.35 mmol) was added. The mixture was stirred for sixty minutes at room temperature. Dichloromethane (100 mL) was added into the solution. The resulting solution was washed with 10% of sodium carbonate and water. The organic phase was dried over sodium sulfate. Evaporation of the solvent and purification of the residue by flash chromatography yielded product as a free base (0.035 g, yield: 46%). $^1$H NMR (500 MHz, CDCl$_3$): δ 7.32 (m, 1H), 7.22, 7.09 (dd, 2H), 6.85 (m, 4H), 6.05 (m, 0.87H), 5.05 (m, 0.13H), 4.31 (m, 1H), 4.10 (m, 2H), 3.96 (m, 2H), 3.78 (d, 1H), 3.65 (d, 1H), 3.20 (m, 2H), 2.95 (m, 1H), 2.75 (m, 5H), 2.40 (m, 2H), 2.20 (m, 1H), 1.75 (m, 1H); MS (EI) for C$_{23}$H$_{28}$F$_2$N$_2$O$_4$: 435 (MH$^+$). The free base was converted to hydrochloride salt and dried by lyophilization.

Example 16

Preparation of N-{(1S)-1-[4-(2-Hydroxyethoxy)phenyl]-2-[(3S)-3-hydroxypyrrolidin-1-yl]ethyl}-N-methyl-2-(6-methylpyridin-3-yl)acetamide, dihydrochloride salt

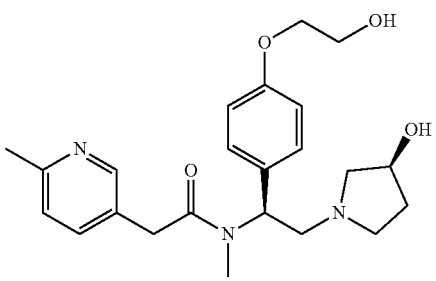 [SMILES: Cc1ccc(CC(=O)N(C)[C@H](CN2CC[C@H](O)C2)c2ccc(OCCO)cc2)cn1]

Using a synthetic approach similar to the one employed in Example 15, N-{(1S)-1-[4-(2-hydroxy ethoxy)phenyl]-2-[(3S)-3-hydroxypyrrolidin-1-yl]ethyl}-N-methyl-2-(6-methylpyridin-3-yl)acetamide dihydrochloride salt was prepared. $^1$H NMR (500 MHz, CDCl$_3$): δ 8.84 (s, 1H), 7.50 (d, 1H), 7.22 (dd, 2H), 7.12 (d, 1H), 6.90 (d, 2H), 6.20 (m, 0.85H), 5.05 (m, 0.15H), 4.35 (m, 1H), 4.10 (m, 2H), 3.96 (m, 2H), 3.85 (d, 1H), 3.70 (d, 1H), 3.35 (m, 1H), 3.28 (t, 1H), 2.95 (d, 1H), 2.65 (s, 3H), 2.60 (m, 2H), 2.55 (s, 3H), 2.32 (m, 1H), 2.10 (br. 1H), 1.85 (m, 1H); MS (EI) for C$_{23}$H$_{31}$N$_3$O$_4$: 414 (MH$^+$).

Example 17

Preparation of 2-(3,4-Dichlorophenyl)-N—((S)-2-((S)-3-((2-(2-(2-hydroxyethoxy)ethoxy)ethyl)amino)pyrrolidin-1-yl)-1-phenylethyl)-N-methylacetamide, hydrochloride salt

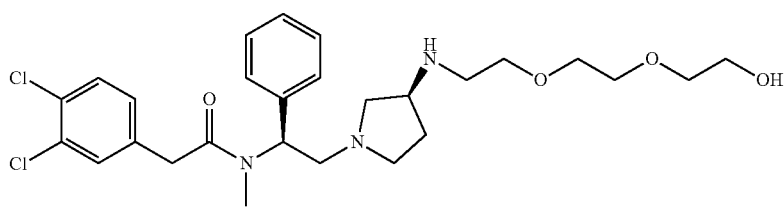 [SMILES: CN(C(=O)Cc1ccc(Cl)c(Cl)c1)[C@H](CN1CC[C@H](NCCOCCOCCO)C1)c1ccccc1]

2-(3,4-Dichlorophenyl)-N—((S)-2-((S)-3-((2-(2-(2-hydroxy ethoxy)ethoxy)ethyl)amino)pyrrolidin-1-yl)-1-phenylethyl)-N-methylacetamide, hydrochloride salt may be prepared according to the following steps.

Step 1: Synthesis of tert-butyl ((S)-2-((R)-3-hydroxypyrrolidin-1-yl)-2-oxo-1-phenylethyl)carbamate

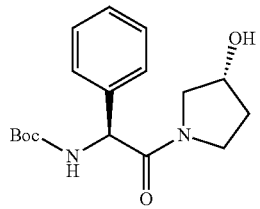

tert-Butoxycarbonylamino-phenyl-acetic acid (1.9 g, 7.56 mmol) and 4-methylmorpholine (0.99 mL, 8.99 mmol) were dissolved in tetrahydrofuran (25 mL). The resultant solution was cooled in an ice-bath under stirring for ten minutes. Ethyl chloroformate (0.742 mL, 7.56 mmol) in tetrahydrofuran (5 mL) was added. The reaction mixture was stirred for thirty minutes, and then (R)-3-pyrrolidino hydrochloric acid salt (1.02 g, 8.31 mmol) was added. The mixture was stirred at room temperature for 16 hours, and then 50 mL of ethyl acetate was added. The solution was washed with water (30 mL×3), dried over sodium sulfate and concentrated to give tert-butyl {(1S)-2-((3R)-3-hydroxypyrrolidin-1-yl)-2-oxo-1-phenylethyl}carbamate (2.0 g, crude).

Step 2: Synthesis of (R)-1-((S)-2-(methylamino)-2-phenylethyl)pyrrolidin-3-ol

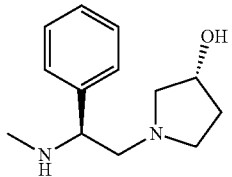 [SMILES: CN[C@H](CN1CC[C@@H](O)C1)c1ccccc1]

A solution of tert-butyl {(1S)-2-((3R)-3-hydroxypyrrolidin-1-yl)-2-oxo-1-phenylethyl}carbamate (920 mg) in tetrahydrofuran (20 mL) was added drop wise to a stirred 2.0 M solution of lithium aluminum hydride (436 mg) in tetrahydrofuran. The mixture was stirred for 0.5 hours at room temperature and then heated at 65° C. for four hours. A 3N solution of sodium carbonate was added cautiously until effervescence ceased. The solid was filtered out and washed with dichloromethane (40 mL). The filtrate was concentrated and the residue was dissolved in 50 mL of dichloromethane. The resulting solution was washed with saturated sodium chloride solution (50 mL) and dried over sodium sulfate. (3R)-1-[(2S)-2-(Methylamino)-2-phenylethyl]pyrrolidin-3-ol was obtained after removing solvent (550 mg).

Step 3: Synthesis of 2-(3,4-dichlorophenyl)-N—((S)-2-((R)-3-hydroxypyrrolidin-1-yl)-1-phenylethyl)-N-methylacetamide

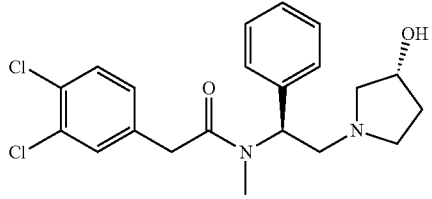 [SMILES: CN(C(=O)Cc1ccc(Cl)c(Cl)c1)[C@H](CN1CC[C@@H](O)C1)c1ccccc1]

(3R)-1-[(2S)-2-(Methylamino)-2-phenylethyl]pyrrolidin-3-ol (0.70 g, 2.39 mmol), 2-(3,4-dichlorophenyl) acetic acid (460 mg, 2.17 mmol) was dissolved in acetonitrile (20 mL). Diisopropylethylamine (0.5 mL, 4.34 mmol) was added. The mixture was stirred for ten minutes at room temperate and then cooled to 0° C. HATU (900 mg, 2.6 mmol) was added into the solution. The reaction mixture was stirred overnight. Ethyl acetate (50 mL) was added and washed with saturated sodium bicarbonate (2×30 mL), brine (30 mL) and dried over sodium sulfate. Evaporation of the solvent afforded the crude (880 mg). Half of the material was purified by prep HPLC to give the TFA salt (300 mg). After free basing with sodium bicarbonate, the free base was dissolved in 3 mL of acetonitrile. To the solution was added 1 mL 1N hydrochloride. The mixture was lyophilized to afford product 2-(3,4-Dichlorophenyl)-N-{(1S)-2-((3R)-3-hydroxypyrrolidin-1-yl)-1-phenylethyl}-N-methylacetamide as hydrochloride salt (220 mg). LC-MS (ESI, MH+): 407.5.

Step 4: Synthesis of (R)-1-((S)-2-(2-(3,4-dichlorophenyl)-N-methylacetamido)-2-phenylethyl)pyrrolidin-3-yl methanesulfonate

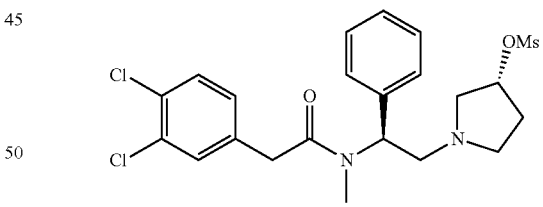

2-(3,4-Dichlorophenyl)-N-{(1S)-2-((3R)-3-hydroxypyrrolidin-1-yl)-1-phenylethyl}-N-methylacetamide (1.07 g, 2.62 mmol) was dissolved in dichloromethane (10 ml) and cooled to 0° C. Triethylamine (0.73 mL, 5.24 mmol) was added dropwise. The mixture was stirred for ten minutes before methanesulfonic chloride (0.42 mL, 5.24 mmol) was added. The reaction mixture was stirred overnight. Dichloromethane (50 mL) was added and washed with water (2×30 mL) and brine (30 mL) and dried over sodium sulfate. Evaporation of the solvent afforded the crude material methanesulfonic acid (R)-1-((S)-2-{[2-(3,4-dichloro-phenyl)-acetyl]-methyl-amino}-2-phenyl-ethyl)-pyrrolidin-3-yl ester (0.78 g) LC-MS (ESI, MH+): 485.42.

Step 5: Synthesis of 2-(3,4-dichlorophenyl)-N—((S)-2-((S)-3-((2-(2-(2-hydroxyethoxy)ethoxy)ethyl)amino)pyrrolidin-1-yl)-1-phenylethyl)-N-methylacetamide, hydrochloride salt

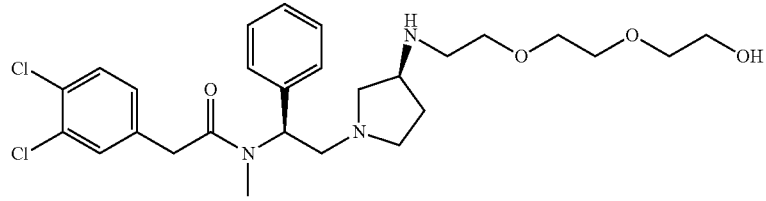 [SMILES: CN(C(=O)Cc1ccc(Cl)c(Cl)c1)[C@H](CN1CC[C@H](NCCOCCOCCO)C1)c1ccccc1]

Methanesulfonic acid (R)-1-((S)-2-{[2-(3,4-dichloro-phenyl)-acetyl]-methyl-amino}-2-phenyl-ethyl)-pyrrolidin-3-yl ester (1.0 equivalent) and 2-(2-(2-aminoethoxy)ethoxy)ethanol (1.2 equivalent) was dissolved in dimethylformamide (1 mL) and heated at 80 C for ten hours. The reaction mixture was purified by prep HPLC with hydrochloric acid buffer to give 2-(3,4-dichlorophenyl)-N—((S)-2-((S)-3-((2-(2-(2-hydroxyethoxy)ethoxy)ethyl)amino)pyrrolidin-1-yl)-1-phenylethyl)-N-methylacetamide, hydrochloride salt. LC-MS (ESI, MH+): 539.

Example 18

Preparation of 1N-{(1S)-1-[4-(2-Hydroxyethoxy)phenyl]-2-[(3S)-3-hydroxypyrrolidin-1-yl]ethyl}-N-methyl-2-(1,3-thiazol-2-yl)acetamide, hydrochloride salt

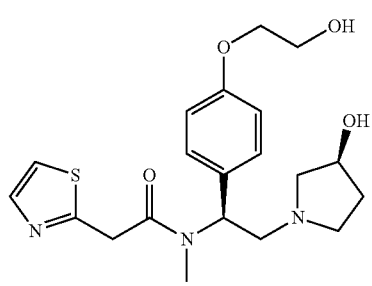 [SMILES: CN(C(=O)Cc1nccs1)[C@H](CN1CC[C@H](O)C1)c1ccc(OCCO)cc1]

Using a synthetic approach similar to the one employed in Example 15, N-{(1S)-1-[4-(2-Hydroxy ethoxy)phenyl]-2-[(3S)-3-hydroxypyrrolidin-1-yl]ethyl}-N-methyl-2-(1,3-thiazol-2-yl)acetamide hydrochloride salt was prepared. $^1$H NMR (500 MHz, CDCl$_3$): 7.74 (d, 1H), 7.31 (d, 1H), 7.22, 7.12 (d, 2H), 6.87 (d, 2H), 6.05 (m, 0.82H), 5.25 (m, 0.18H), 4.30 (m, 2H), 4.10 (m, 3H), 3.96 (m, 2H), 3.20 (m, 2H), 3.00 (m, 1H), 2.80 (s, 3H), 2.70 (m, 2H), 2.20 (m, 2H), 1.75 (m, 1H); MS (EI) for C$_{20}$H$_{27}$N$_3$O$_4$S: 406 (MH+).

Example 19

Synthesis of 2-(3,4-Dichlorophenyl)-N—((S)-2-((S)-3-((2-(2-hydroxyethoxy)ethyl)amino)pyrrolidin-1-yl)-1-phenylethyl)-N-methylacetamide, hydrochloride salt

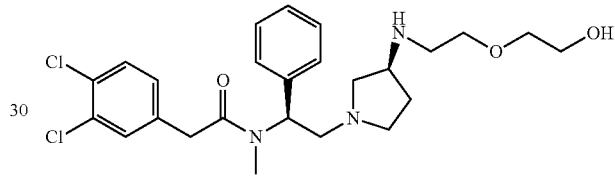

Methanesulfonic acid (R)-1-((S)-2-{[2-(3,4-dichloro-phenyl)-acetyl]-methyl-amino}-2-phenyl-ethyl)-pyrrolidin-3-yl ester (preparation described in Step 4 of Example 17) (1.0 equivalent) and 2-(2-aminoethoxy)ethanol (1.2 equivalents) were dissolved in dimethylformamide (1 mL) and heated at 80 C for ten hours. The reaction mixture was purified by prep HPLC with hydrochloric acid buffer to give 2-(3,4-dichlorophenyl)-N—((S)-2-((S)-3-((2-(2-hydroxyethoxy)ethyl)amino)pyrrolidin-1-yl)-1-phenylethyl)-N-methylacetamide, hydrochloride salt. LC-MS (ESI, MH+): 495.

Example 20

Preparation of 2-(2,4-difluorophenyl)-N—((S)-1-(4-(2-hydroxyethoxy)phenyl)-2-((S)-3-(2-hydroxyethoxy)pyrrolidin-1-yl)ethyl)-N-methylacetamide, hydrochloride salt

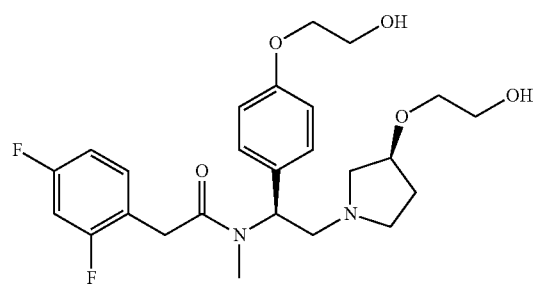 [SMILES: CN(C(=O)Cc1ccc(F)cc1F)[C@H](CN1CC[C@H](OCCO)C1)c1ccc(OCCO)cc1]

Using a synthetic approach similar to the one employed in Example 19, 2-(2,4-difluorophenyl)-N—((S)-1-(4-(2-hydroxyethoxy)phenyl)-2-((S)-3-(2-hydroxyethoxy)pyrrolidin-1-yl)ethyl)-N-methylacetamide, hydrochloride salt was prepared. δ 7.35 (m, 1H), 7.20, 7.09 (m, 2H), 6.85 (m, 4H), 6.05 (m, 0.86H), 5.05 (m, 0.14H), 4.05 (m, 3H), 3.95 (m, 2H), 3.60 (m, 4H), 3.50 (m, 2H), 3.15 (m, 1H), 3.02 (m, 1H), 2.60 (m, 6H), 2.50 (m, 2H), 2.10 (m, 1H), 1.85 (m, 1H); MS (EI) for $C_{25}H_{32}F_2N_2O_5$: 479 (MH$^+$).

Example 21

Preparation of 2-(3,4-Difluorophenyl)-N-{(1S)-1-[4-(2-hydroxyethoxy)phenyl]-2-[(3S)-3-(2-hydroxyethoxy)pyrrolidin-1-yl]ethyl}-N-methylacetamide, hydrochloride salt

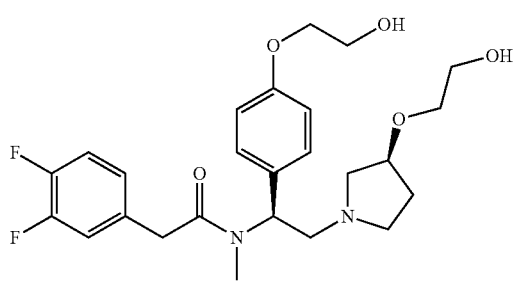 [SMILES: CN(C(=O)Cc1ccc(F)c(F)c1)[C@H](CN1CC[C@H](OCCO)C1)c1ccc(OCCO)cc1]

Using a synthetic approach similar to the one employed in Example 19, 2-(3,4-difluorophenyl)-N-{(1S)-1-[4-(2-hydroxyethoxy)phenyl]-2-[(3 S)-3-(2-hydroxyethoxy)pyrrolidin-1-yl]ethyl}-N-methylacetamide, hydrochloride salt was prepared. δ 7.20 (d, 2H), 7.15 (m, 2H), 7.02 (m, 1H), 6.88 (d, 2H), 6.06 (m, 0.83H), 5.05 (m, 0.17H), 4.06 (m, 3H), 3.96 (m, 2H), 3.75 (m, 4H), 3.50 (m, 2H), 3.18 (t, 1H), 2.95 (m, 2H), 2.55 (m, 5H), 2.40 (m, 2H), 2.10 (m, 1H), 1.80 (m, 1H); MS (EI) for $C_{25}H_{32}F_2N_2O_5$: 479 (MH$^+$).

Example 22

Preparation of 1-(3,4-Dichlorophenyl)-N-{(1S)-1-[4-(2-hydroxyethoxy)phenyl]-2-[(3S)-3-hydroxypyrrolidin-1-yl]ethyl}-N-methylmethanesulfonamide, hydrochloride salt

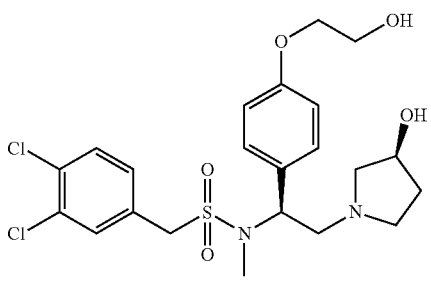 [SMILES: CN([C@H](CN1CC[C@H](O)C1)c1ccc(OCCO)cc1)S(=O)(=O)Cc1ccc(Cl)c(Cl)c1]

(3S)-1-((2S)-2-(Methylamino)-2-(4-(2-((tetrahydro-2H-pyran-2-yl)oxy)ethoxy)phenyl)ethyl)pyrrolidin-3-ol (0.072 g, 0.20 mmol) (preparation described in Step 3 of Example 15), (3,4-dichlorophenyl)methanesulfonyl chloride (0.051 g, 0.20 mmol), and N,N-diisopropylethylamine (0.07 mL) were dissolved in 10 mL of dichloromethane. The mixture was stirred for three hours at 0° C. and then warmed to room temperature overnight. Dichloromethane (50 mL) was added into the mixture. The resultant solution was washed with water and dried over sodium sulfate. The solvent was removed and the residue was purified by flash chromatography. From this residue, 0.040 g (0.068 mmol, yield: 35%) of the target intermediate was obtained, which was dissolved in 10 mL of methanol. 4-Methylbenzenesulfonic acid (0.026 g, 0.14 mmol) was added into the solution and the mixture was stirred for one hour at room temperature. Dichloromethane (50 mL) was added into the solution and washed with sodium carbonate solution (10%), water, and dried over sodium sulfate. Evaporation of the solvent and purification of the residue by flash chromatography yielded the named product as a free base (0.020 g, yield: 58%). $^1$H NMR (500 MHz, CDCl$_3$): δ 7.42 (d, 1H), 7.38 (s, 1H), 7.22 (d, 1H), 7.08 (d, 2H), 6.88 (d, 2H), 5.15 (m, 1H), 4.35 (m, 1H), 4.30 (m, 2H), 4.10 (m, 2H), 4.00 (m, 2H), 3.30 (m, 2H), 2.82 (m, 1H), 2.74 (m, 1H), 2.63 (m, 1H), 2.43 (s, 3H), 2.20 (m, 3H), 1.80 (m, 1H); MS (EI) for $C_{22}H_{28}Cl_2N_2O_5S$: 503 (MH$^+$). The free base was converted to hydrochloride salt and dried by lyophilization.

Example 23

Preparation of N-{(1S)-1-[4-(2-Hydroxyethoxy)phenyl]-2-[(3S)-3-hydroxypyrrolidin-1-yl]ethyl}-N-methyl-1-[4-(trifluoromethyl)phenyl]methanesulfonamide, hydrochloride salt

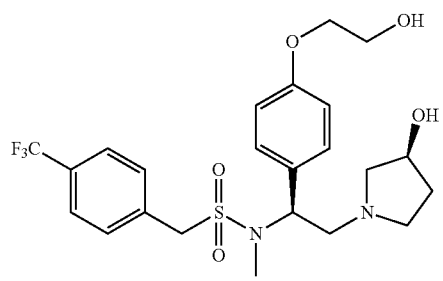 [SMILES: CN([C@H](CN1CC[C@H](O)C1)c1ccc(OCCO)cc1)S(=O)(=O)Cc1ccc(C(F)(F)F)cc1]

Using a synthetic approach similar to the one employed in Example 22, N-{(1S)-1-[4-(2-hydroxyethoxy)phenyl]-2-[(3 S)-3-hydroxypyrrolidin-1-yl]ethyl}-N-methyl-1-[4-(trifluoromethyl)phenyl]methanesulfonamide, hydrochloride salt was prepared. $^1$H NMR (500 MHz, CDCl$_3$): δ 7.60 (d, 2H), 7.45 (d, 2H), 7.00 (d, 2H), 6.85 (d, 2H), 5.12 (m, 1H), 4.40 (m, 3H), 4.10 (m, 2H), 3.98 (m, 2H), 3.30 (m, 2H), 2.80 (d, 1H), 2.74 (m, 1H), 2.65 (m, 1H), 2.50 (s, 3H), 2.20 (m, 3H), 1.80 (m, 1H); MS (EI) for $C_{23}H_{29}F_3N_2O_5S$: 503 (MH$^+$).

Example 24

Preparation of (S)-2-(3,4-dichlorophenyl)-N-(2-(3-hydroxyazetidin-1-yl)-1-(4-(2-hydroxyethoxy)phenyl)ethyl)-N-methylacetamide, hydrochloride salt Using the synthetic approach schematically outlined below, (S)-2-(3,4-dichlorophenyl)-N-(2-(3-hydroxyazetidin-1-yl)-1-(4-(2-hydroxyethoxy)phenyl)ethyl)-N-methylacetamide, hydrochloride salt was prepared.

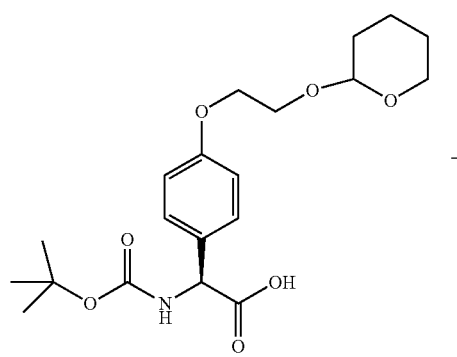

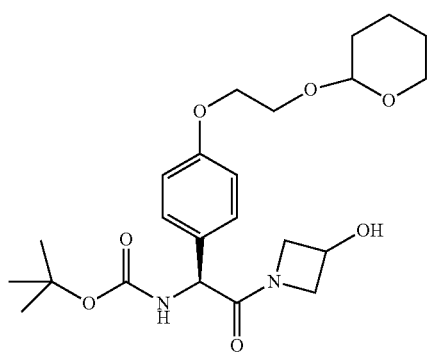 [SMILES: CC(C)(C)OC(=O)N[C@H](C(=O)N1CC(O)C1)c1ccc(OCCOC2CCCCO2)cc1]

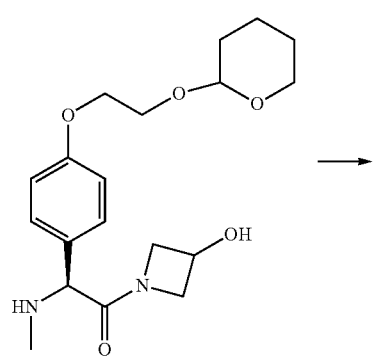

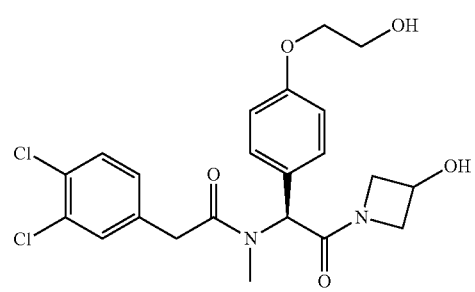

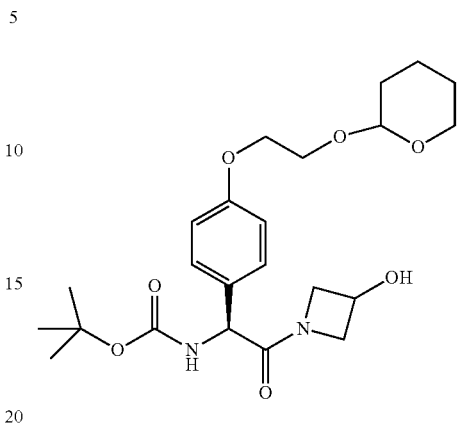

Step 1: Preparation of tert-butyl ((1S)-2-(3-hydroxyazetidin-1-yl)-2-oxo-1-(4-(2-((tetrahydro-2H-pyran-2-yl)oxy)ethoxy)phenyl)ethyl)carbamate (2S)-2-((Tert-butoxycarbonyl)amino)-2-(4-(2-((tetrahydro-2H-pyran-2-yl)oxy)ethoxy)phenyl)acetic acid (0.80 g, 2.02 mmol) and O-(benzotriazol-1-yl)-N,N,N',N'-tetramethyluronium tetrafluoroborate (0.78 g, 2.43 mmol) were dissolved in 10 mL of dimethylformamide. N,N-Diisopropylethylamine (0.78 g, 6.07 mmol) and 3-hydroxyazetidine hydrochloride (0.33 g, 3.0 mmol) were added. The mixture was stirred at room temperature for one hour. Dichloromethane (100 mL) was added, and the resulting solution was washed with water (100 mL×3). The solution was dried over sodium sulfate and concentrated. The residue was purified by flash chromatography (0.60 g, yield: 66%). $^1$H NMR (500 MHz, CDCl$_3$): δ 7.18 (m, 2H), 6.80 (m, 2H), 5.34 (m, 1H), 5.00 (m, 2H), 4.62 (m, 1H), 4.55 (m, 0.5H), 4.35 (m, 1H), 4.15 (m, 0.5H), 4.00 (m, 4H), 3.90 (m, 0.5H), 3.80 (m, 1H), 3.72 (m, 1H), 3.58 (m, 0.5H), 3.45 (m, 1H), 2.65 (m, 1H), 1.75 (m, 1H), 1.65 (m, 1H), 1.50 (m, 4H), 1.30 (s, 9H); MS (EI) for C$_{23}$H$_{34}$N$_2$O$_7$: 451 (MH$^+$).

Step 2: Preparation of 1-((2S)-2-(methylamino)-2-(4-(2-((tetrahydro-2H-pyran-2-yl)oxy)ethoxy)phenyl)ethyl)azetidin-3-ol

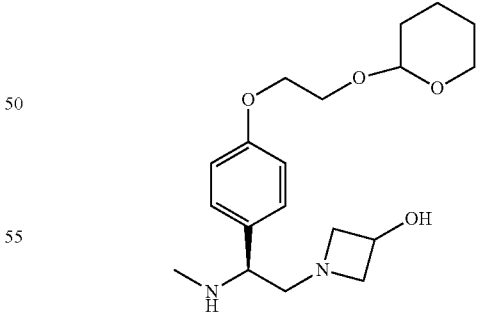

Tert-butyl ((1S)-2-(3-hydroxyazetidin-1-yl)-2-oxo-1-(4-(2-((tetrahydro-2H-pyran-2-yl)oxy)ethoxy)phenyl)ethyl)carbamate (0.335 g, 0.744 mmol) was dissolved in tetrahydrofuran (10 mL). A 2.0 lithium aluminum hydride solution (2.0 mL, 4 mmol) was added into the solution at room temperature. The mixture was stirred at 65° C. for four hours. A 3N solution of sodium carbonate was added cautiously until effervescence ceased. Ethyl acetate (100 mL)

was added into the mixture. The solid was filtered out and washed with ethyl acetate (50 mL). The filtrate was washed with saturated sodium chloride solution and dried over sodium sulfate. The product was obtained after removing solvent (0.2 g, yield: 77%). MS (EI) for $C_{19}H_{30}N_2O_4$: 351 (MH+).

Step 3: Preparation of (S)-2-(3,4-dichlorophenyl)-N-(2-(3-hydroxyazetidin-1-yl)-1-(4-(2-hydroxyethoxy)phenyl)ethyl)-N-methylacetamide, hydrochloride salt

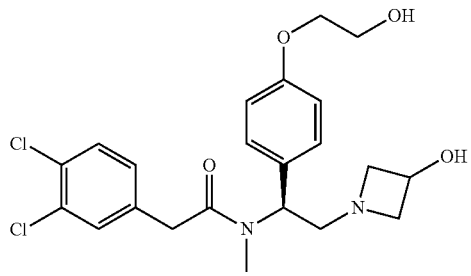 [SMILES: CN(C(=O)Cc1ccc(Cl)c(Cl)c1)[C@H](CN1CC(O)C1)c1ccc(OCCO)cc1]

1-((2S)-2-(Methylamino)-2-(4-(2-((tetrahydro-2H-pyran-2-yl)oxy)ethoxy)phenyl)ethyl)azetidin-3-ol (0.140 g, 0.40 mmol), 3,4-dichlorophenylacetic acid (0.081 g, 0.40 mmol), and N,N-diisopropylethylamine (0.104 g, 0.80 mmol) were dissolved in 3 mL of acetonitrile. The mixture was stirred for ten minutes at room temperature and then cooled to 0° C. O-(Benzotriazol-1-yl)-N,N,N',N'-tetramethyluronium tetrafluoroborate (0.153 g, 0.477 mmol) was added into the solution. The reaction mixture was stirred for one hour under an ice-bath. Dichloromethane (100 mL) was added into the mixture. The resulting solution was washed with water and dried over sodium sulfate. Evaporation of the solvent and purification of the residue by flash chromatography yielded a product (0.091 g, yield 43%). This product (0.056 g, 0.10 mmol) and 4-methylbenzenesulfonic acid (0.035 g, 0.21 mmol) were dissolved in 10 mL of methanol. The mixture was stirred for sixty minutes at room temperature. Evaporation of the solvent and purification of the residue by flash chromatography yielded the named product as free base (0.028 g, yield 42.3%). $^1$H NMR (500 MHz, MeOD): δ 7.50 (m, 2H), 7.25 (m, 1H), 7.20 (m, 2H), 7.00 (d, 2H), 6.05 (m, 1H), 4.68 (m, 1H), 4.50 (m, 2H), 4.10 (m, 4H), 4.00 (m, 1H), 3.90 (m, 4H), 3.80 (m, 1H), 2.75 (s, 3H); MS (EI) for $C_{22}H_{26}Cl_2N_2O_4$: 453 (MH+). The free base was converted to hydrochloride salt and dried by lyophilization.

Example 25

Preparation of 2-(3,4-dichlorophenyl)-N-methyl-N—((S)-2-((S)-3-morpholinopyrrolidin-1-yl)-1-phenylethyl)acetamide, hydrochloride salt

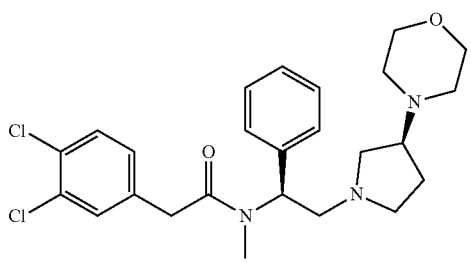 [SMILES: CN(C(=O)Cc1ccc(Cl)c(Cl)c1)[C@H](CN1CC[C@H](N2CCOCC2)C1)c1ccccc1]

2-(3,4-Dichlorophenyl)-N-methyl-N—((S)-2-((S)-3-morpholinopyrrolidin-1-yl)-1-phenylethyl)acetamide was synthesized according to the following steps Step 1: Preparation of (S)-2-(((benzyloxy)carbonyl)amino)-2-phenylacetic acid

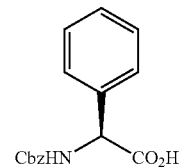

To a solution (S)-2-amino-2-phenylacetic acid (20 g, 0.132 mol) in water (500 mL) was added $Na_2CO_3$ (27.97 g, 0.264 mol) and $NaHCO_3$ (11.1 g, 0.132 mol) at ambient temperature. The mixture was stirred to give a clear solution. Acetone (40 mL) was added and the slightly turbid solution was cooled in an ice water bath to 15-20° C. Cbz-Cl (28.15 g, 0.165 mol) was added slowly, with stirring, and the reaction mixture allowed to warm to ambient temperature. After stirring for an additional three hours, the mixture was extracted with MTBE (100 mL). The pH of an aqueous layer was adjusted to 2 using aqueous HCl. The resulting oil was extracted into EtOAc (100 mL×2). The combined organic layer was washed with $H_2O$ and then concentrated in vacuo to give (S)-2-(((benzyloxy)carbonyl)amino)-2-phenylacetic acid (30.2 g, 80% yield) as a white color solid.

Step 2: Preparation of benzyl ((S)-2-((R)-3-hydroxypyrrolidin-1-yl)-2-oxo-1-phenylethyl) carbamate

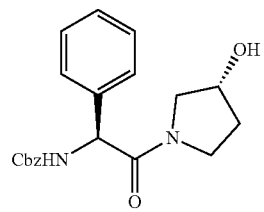 [SMILES: O=C(N[C@H](C(=O)N1CC[C@@H](O)C1)c1ccccc1)OCc1ccccc1]

(S)-2-(((Benzyloxy)carbonyl)amino)-2-phenylacetic acid (10.36 g, 36.3 mmol), (R)-pyrrolidin-3-ol (3.48 g, 39.93 mmol) and DIPEA (14.0 g, 108.9 mmol) were dissolved in acetonitrile (80 mL). The mixture was stirred for 15 minutes at 22-25° C. and then cooled to 0° C. O-(Benzotriazol-1-yl)-N,N,N',N'-tetramethyluronium tetrafluoroborate (TBTU) (14.0 g, 43.56 mmol) was added into the solution. The reaction mixture was stirred for one hour at 0° C. and then for four hours at ambient temperature. The reaction mixture was concentrated under reduced pressure. The resulting residue was dissolved in DCM (50 mL) and washed with brine (25 mL×2). The solution was dried over anhydrous sodium sulfate and concentrated. The obtained residue was purified by column chromatography yielded ((S)-2-((R)-3-hydroxypyrrolidin-1-yl)-2-oxo-1-phenylethyl) carbamate (7.5 g, 58% yield).

Step 3: Preparation of (R)-1-((S)-2-(methylamino)-2-phenylethyl)pyrrolidin-3-ol

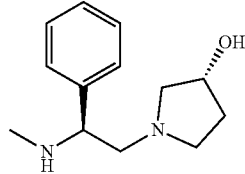 [SMILES: CN[C@H](CN1CC[C@@H](O)C1)c1ccccc1]

((S)-2-((R)-3-hydroxypyrrolidin-1-yl)-2-oxo-1-phenylethyl) carbamate (7.0 g, 19.75 mmol) was dissolved in THF (55 mL). The mixture was then cooled to 0° C. and LAH (3.74 g, 98.75 mmol) was added. The mixture was stirred for 15 minutes at 0° C., followed by stirring for 16 hours at 65° C. The reaction mass was cooled to 0° C. and 3N aq. sodium carbonate solution (150 mL) was added (cautiously) until effervescence ceased. A precipitated solid was filtered and washed with EtOAc (100 mL). The filtrate was concentrated and the residue was dissolved in EtOAc (150 mL). The product was extracted into 1N aq. HCl (2×25 mL) and washed with MTBE (3×15 mL). The pH of the aqueous layer was adjusted to 9, and the product was extracted into EtOAc. The organic layer was washed with brine, dried over anhydrous sodium sulfate and concentrated under vacuum to obtain a crude compound. The crude compound, upon purification using column chromatography yielded (R)-1-((S)-2-(methylamino)-2-phenylethyl)pyrrolidin-3-ol (2.5 g, 58% yield).

Step 4: Preparation of 2-(3,4-dichlorophenyl)-N—((S)-2-((R)-3-hydroxypyrrolidin-1-yl)-1-phenylethyl)-N-methylacetamide

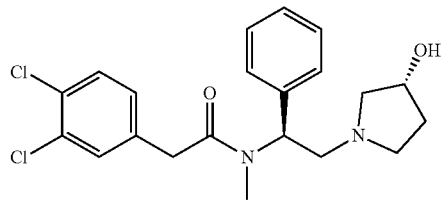 [SMILES: CN(C(=O)Cc1ccc(Cl)c(Cl)c1)[C@H](CN1CC[C@@H](O)C1)c1ccccc1]

To a solution of (R)-1-((S)-2-(methylamino)-2-phenylethyl)pyrrolidin-3-ol (2.5 g, 11.35 mmol) in ACN (40 mL) were added 3,4-dichlorophenyl acetic acid (2.56 g, 12.48 mmol), HOBt.H₂O (1.84 g, 13.62 mmol), DIPEA (2.2 g, 17.02 mmol) and EDC.HCl (3.26 g, 17.02 mmol) at ambient temperature. The mixture was stirred for two hours and ACN was distilled off. The crude compound, dissolved in DCM (25 mL), was washed with 10% Na₂CO₃ (4×25 mL), 10% NH₄Cl (4×25 mL), and brine (25 mL). The organic layer was dried over anhydrous sodium sulfate and concentrated under vacuum. The resultant gummy mass upon purification by column chromatography yielded 2-(3,4-dichlorophenyl)-N—((S)-2-((R)-3-hydroxypyrrolidin-1-yl)-1-phenylethyl)-N-methylacetamide (2.9 g, 63% yield).

Step 5: Preparation of (R)-1-((S)-2-(2-(3,4-dichlorophenyl)-N-methylacetamido)-2-phenylethyl)pyrrolidin-3-yl methanesulfonate

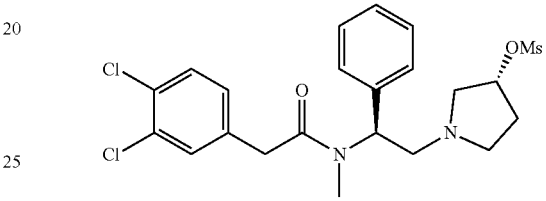

To a solution of 2-(3,4-dichlorophenyl)-N—((S)-2-((R)-3-hydroxypyrrolidin-1-yl)-1-phenylethyl)-N-methylacetamide (0.5 g, 1.23 mmol) in DCM (5 mL) were added TEA (1.48 mmol) and MsCl (1.35 mmol) at ambient temperature. The mixture was stirred for two hours and quenched with H₂O (10 mL). The organic layer was separated and washed with 5% aq. NH₄C₁ (5 mL×2) followed by brine (5 mL). The organic layer was dried over anhydrous sodium sulfate and concentrated under vacuum to give (R)-1-((S)-2-(2-(3,4-dichlorophenyl)-N-methylacetamido)-2-phenylethyl)pyrrolidin-3-yl methanesulfonate (0.53 g, 90% yield) as a light yellow color gum.

Step 6: Preparation of N—((S)-2-((S)-3-azidopyrrolidin-1-yl)-1-phenylethyl)-2-(3,4-dichlorophenyl)-N-methylacetamide

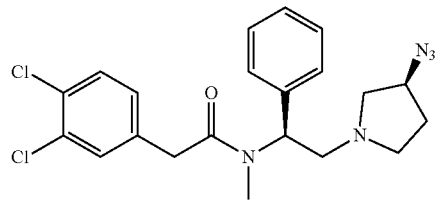 [SMILES: CN(C(=O)Cc1ccc(Cl)c(Cl)c1)[C@H](CN1CC[C@H](N=[N+]=[N-])C1)c1ccccc1]

To a solution of (R)-1-((S)-2-(2-(3,4-dichlorophenyl)-N-methylacetamido)-2-phenylethyl)pyrrolidin-3-yl methanesulfonate (0.5 g, 1.03 mmol) in DMF (5 mL) was added NaN₃ (0.1 g, 1.54 mmol). The mixture was heated to 60° C. for three hours. After cooling down to ambient temperature, the mixture was concentrated under reduced pressure, treated with H₂O (10 mL) and extracted with DCM (10 mL×2). The combined organic layer was washed with brine (20 mL) and concentrated under vacuum to afford N—((S)-2-((S)-3-azidopyrrolidin-1-yl)-1-phenylethyl)-2-(3,4-dichlorophenyl)-N-methylacetamide (0.39 g, 88% yield) as brown color gum.

Step 7: Preparation of N—((S)-2-((S)-3-aminopyrrolidin-1-yl)-1-phenylethyl)-2-(3,4-dichlorophenyl)-N-methylacetamide

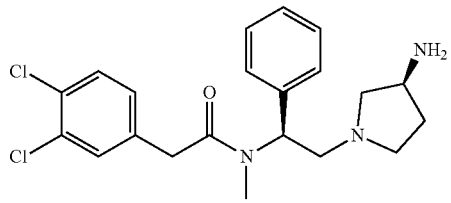 [SMILES: CN(C(=O)Cc1ccc(Cl)c(Cl)c1)[C@H](CN1CC[C@H](N)C1)c1ccccc1]

A solution of N—((S)-2-((S)-3-azidopyrrolidin-1-yl)-1-phenylethyl)-2-(3,4-dichlorophenyl)-N-methylacetamide (0.35 g, 0.81 mmol) and H$_2$O (87 μL, 4.86 mmol) in THF (3.5 mL) was cooled with an ice-bath at 0° C. PPh$_3$ (0.425 g, 1.62 mmol) was added into the mixture as a solid in small portions. After the addition, the mixture was slowly warmed to ambinet temperature and then heated to 50° C. for five hours. After five hours, the mixture was concentrated in vacuum and mixed with H$_2$O (7 mL) and DCM (10 mL) and then acidified with 1N HCl to pH 2. The mixture was washed with DCM (10 mL×2) and the aqueous phase was then treated with 6N NaOH to maintain pH 10. After extraction with DCM (10 mL×3), the organic layers were combined and washed with brine (10 mL), dried over anhydrous sodium sulfate and concentrated under vacuum to give N—((S)-2-((S)-3-aminopyrrolidin-1-yl)-1-phenylethyl)-2-(3,4-dichlorophenyl)-N-methylacetamide (0.23 g, 70% yield) as light yellow color gum.

Step 8: Preparation of 2-(3,4-dichlorophenyl)-N-methyl-N—((S)-2-((S)-3-morpholinopyrrolidin-1-yl)-1-phenylethyl)acetamide

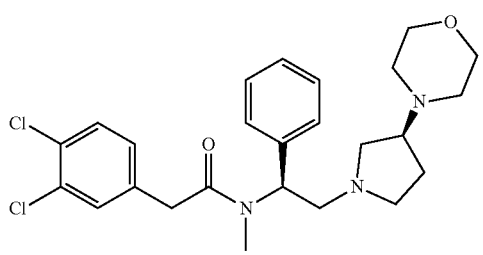 [SMILES: CN(C(=O)Cc1ccc(Cl)c(Cl)c1)[C@H](CN1CC[C@H](N2CCOCC2)C1)c1ccccc1]

To a solution of N—((S)-2-((S)-3-aminopyrrolidin-1-yl)-1-phenylethyl)-2-(3,4-dichlorophenyl)-N-methylacetamide (640 mg, 1.58 mmol) in 1,4-dioxane:H$_2$O (5 vol) were added 1-bromo-2-(2-(trifluoromethoxy)ethoxy)ethane (450 mg, 1.90 mmol), sodium lauryl sulphate (45 mg, 0.158 mmol) and K$_2$CO$_3$ (530 mg, 4.79 mmol). The mixture was heated to 80° C. for sixteen hours. After sixteen hours, the mixture was concentrated in vacuum and the crude was dissolved in EtOAc (10 mL). The organic layer was washed with water (10 mL) and brine (10 mL), dried over anhydrous Na$_2$SO$_4$ and concentrated under vacuum to give a crude product. The crude product was purified by column chromatography to yield 2-(3,4-dichlorophenyl)-N-methyl-N—((S)-2-((S)-3-morpholinopyrrolidin-1-yl)-1-phenylethyl)acetamide (80 mg, 11% yield). $^1$H NMR (500 MHz, CDCl$_3$): δ 7.42-7.36 (m, 2H), 7.35-7.24 (m, 4.6H), 7.18-7.12 (m, 1.4H), 6.1 (m, 0.8H), 4.98 (m, 0.2H), 3.8-3.6 (m, 6H), 3.15-2.9 (m, 2H), 2.84-2.65 (m, 7H), 2.5-2.32 (m, 5H), 2.1-1.9 (m, 1H), 1.75-1.64 (m, 1H); MS (EI) for C$_{25}$H$_{31}$C$_{12}$N$_3$O$_2$: 476 (MH$^+$). The free base was dissolved in 4M hydrochloride in 2-propanol. The mixture was concentrated to afford product as hydrochloride salt.

Example 26

Preparation of N,N'-((1S,1'S)-((3S,3'S)-3,3'-(ethane-1,2-diylbis(azanediyl))bis(pyrrolidine-3,1-diyl))bis(1-phenylethane-2,1-diyl))bis(2-(3,4-dichlorophenyl)-N-methylacetamide), hydrochloride salt

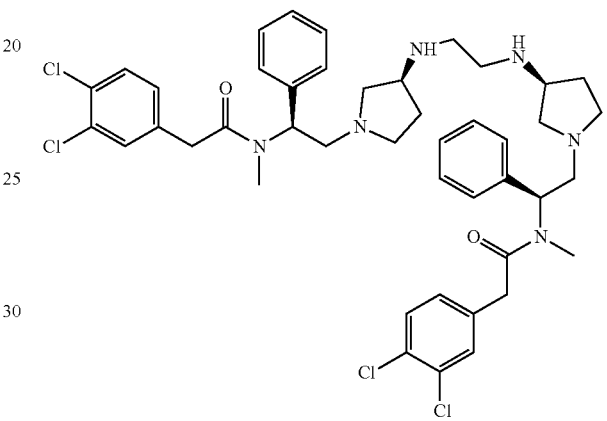

N,N'-((1S,1'S)-((3S,3'S)-3,3'-(ethane-1,2-diylbis(azanediyl))bis(pyrrolidine-3,1-diyl))bis(1-phenylethane-2,1-diyl))bis(2-(3,4-dichlorophenyl)-N-methylacetamide) was synthesized according to the following steps. To a solution of N—((S)-2-((S)-3-aminopyrrolidin-1-yl)-1-phenylethyl)-2-(3,4-dichlorophenyl)-N-methylacetamide (640 mg, 1.58 mmol) in 1,4-dioxane:H$_2$O (5 vol) were added 1-bromo-2-(2-(trifluoromethoxy)ethoxy)ethane (450 mg, 1.90 mmol), sodium lauryl sulphate (45 mg, 0.158 mmol) and K$_2$CO$_3$ (530 mg, 4.79 mmol). The mixture was heated to 80° C. for sixteen hours. After sixteen hours, the mixture was concentrated in vacuum and the crude was dissolved in EtOAc (10 mL). The organic layer was washed with water (10 mL) and brine (10 mL), dried over anhydrous Na$_2$SO$_4$ and concentrated under vacuum to give a crude product. The crude product was purified by column chromatography to yield N,N'-((1S,1'S)-((3S,3'S)-3,3'-(ethane-1,2-diylbis(azanediyl))bis(pyrrolidine-3,1-diyl))bis(1-phenylethane-2,1-diyl))bis(2-(3,4-dichlorophenyl)-N-methylacetamide). (180 mg). $^1$H NMR (500 MHz, CDCl$_3$): δ 7.4-7.2 (m, 12H), 7.18-7.09 (m, 4H), 6.1 (m, 1.6H), 5.1 (m, 0.4H), 4.52-4.12 (m, 4H), 3.8-3.6 (m, 4.6H), 3.12-2.94 (m, 4H), 2.82-2.62 (m, 13.4H), 2.6-2.5 (m, 2H), 2.38-2.18 (m, 4H), 1.6-1.5 (m, 2H); MS (EI) for C$_{44}$H$_{52}$C$_{14}$N$_6$O$_2$: 839 (MH$^+$). The free base was dissolved in 4M hydrochloride in 2-propanol. The mixture was concentrated to afford product as hydrochloride salt.

Example 27

Synthesis of 2-(3,4-dichlorophenyl)-N—((S)-2-((S)-3-((2-hydroxyethyl)amino)pyrrolidin-1-yl)-1-phenylethyl)-N-methylacetamide, hydrochloride salt

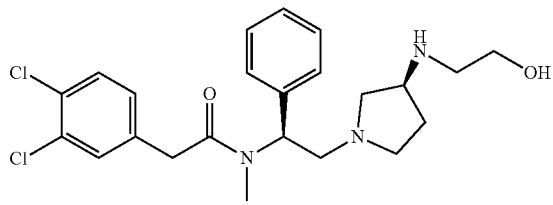 [SMILES: CN(C(=O)Cc1ccc(Cl)c(Cl)c1)[C@H](CN1CC[C@H](NCCO)C1)c1ccccc1]

Methanesulfonic acid (R)-1-((S)-2-{[2-(3,4-dichloro-phenyl)-acetyl]-methyl-amino}-2-phenyl-ethyl)-pyrrolidin-3-yl ester (preparation described in Step 4 of Example 17) (0.257 g, 0.53 mmol) and aminoethanol (0.038 mL, 0.62 mmol) was dissolved in dimethylformamide (1 mL) and heated at 80 C for ten hours. The reaction mixture was purified by prep HPLC to give 2-(3,4-dichloro-phenyl)-N—{(S)-2-[(S)-3-(2-hydroxy-ethylamino)-pyrrolidin-1-yl]-1-phenyl-ethyl}-N-methyl-acetamide, hydrochloride salt. LC-MS (ESI, MH+): 450.45.

Example 28

Preparation of 2-(3,4-dichlorophenyl)-N-methyl-N—((S)-1-phenyl-2-((S)-3-((2-(2-(trifluoromethoxy)ethoxy)ethyl)amino)pyrrolidin-1-yl)ethyl)acetamide, dihydrochloride salt

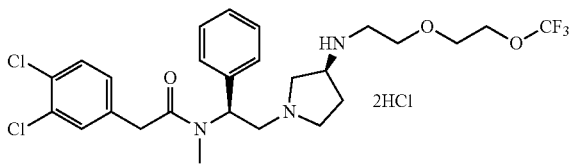 [SMILES: CN(C(=O)Cc1ccc(Cl)c(Cl)c1)[C@H](CN1CC[C@H](NCCOCCOC(F)(F)F)C1)c1ccccc1]

2-(3,4-Dichlorophenyl)-N-methyl-N—((S)-1-phenyl-2-((S)-3-((2-(2-(trifluoromethoxy)ethoxy)ethyl)amino)pyrrolidin-1-yl)ethyl)acetamide, dihydrochloride salt was synthesized according to the following step.

To a solution of N—((S)-2-((S)-3-aminopyrrolidin-1-yl)-1-phenylethyl)-2-(3,4-dichlorophenyl)-N-methylacetamide (640 mg, 1.58 mmol) in 1,4-dioxane:$H_2O$ (5 vol) were added 1-bromo-2-(2-(trifluoromethoxy)ethoxy)ethane (450 mg, 1.90 mmol), sodium lauryl sulphate (45 mg, 0.158 mmol) and $K_2CO_3$ (530 mg, 4.79 mmol). The mixture was heated to 80° C. for sixteen hours. After sixteen hours, the mixture was concentrated in vacuum and the crude was dissolved in EtOAc (10 mL). The organic layer was washed with water (10 mL) and brine (10 mL), dried over anhydrous $Na_2SO_4$ and concentrated under vacuum to give a crude product. The crude product was purified by column chromatography to yield 2-(3,4-dichlorophenyl)-N-methyl-N—((S)-1-phenyl-2-((S)-3-((2-(2-(trifluoromethoxy)ethoxy)ethyl)amino)pyrrolidin-1-yl)ethyl)acetamide (0.091 g, 12% yield).

$^1$H NMR (500 MHz, CDCl$_3$): δ 7.42-7.36 (m, 2H), 7.35-7.24 (m, 4H), 7.18-7.12 (m, 2H), 6.1 (m, 1H), 3.8-3.6 (m, 6H), 3.15-2.98 (m, 2H), 2.8-2.65 (m, 7H), 2.5-2.32 (m, 5H), 1.95 (m, 1H), 1.75-1.64 (m, 1H); MS (EI) for $C_{28}H_{32}Cl_2F_3N_3O_3$: 563 (MH+). The free base was dissolved in 4M hydrochloride in 2-propanol. The mixture was concentrated to afford the product as a dihydrochloride salt.

Example 29

Synthesis of 2-(3,4-dichlorophenyl)-N—((S)-2-((S)-3-((2-(2-methoxyethoxy)ethyl)amino)pyrrolidin-1-yl)-1-phenylethyl)-N-methylacetamide, dihydrochloride salt

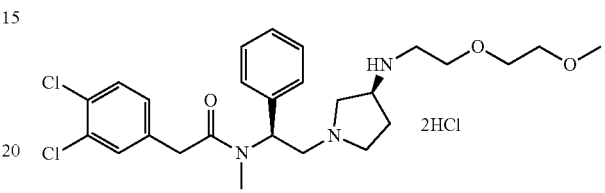

2-(3,4-Dichlorophenyl)-N—((S)-2-((S)-3-((2-(2-methoxyethoxy)ethyl)amino)pyrrolidin-1-yl)-1-phenylethyl)-N-methylacetamide hydrochloride was synthesized according to the following step.

To a solution of N—((S)-2-((S)-3-aminopyrrolidin-1-yl)-1-phenylethyl)-2-(3,4-dichlorophenyl)-N-methylacetamide (500 mg, 1.23 mmol) in 1,4-dioxane:$H_2O$ (5 mL) was added 1-bromo-2-(2-methoxyethoxy)ethane (66 mg, 0.407 mmol), sodium lauryl sulfate (35.47 mg, 0.123 mmol) and $K_2CO_3$ (153 mg, 1.11 mmol). The mixture was heated to 90° C. for eighteen hours. After eighteen hours, the mixture was concentrated and the aqueous layer was extracted into EtOAc (15 mL). The organic layer was washed with brine (10 mL), dried over anhydrous $Na_2SO_4$ and concentrated under vacuum to give a crude product. The crude product was purified by column chromatography to yield 2-(3,4-dichlorophenyl)-N—((S)-2-((S)-3-((2-(2-methoxyethoxy)ethyl)amino)pyrrolidin-1-yl)-1-phenylethyl)-N-methylacetamide hydrochloride (60 mg). $^1$H NMR of free base (500 MHz, DMSO-d$_6$): δ 7.6 (m, 1H), 7.40-7.2 (m, 7H), 5.85 (m, 1H), 3.9 (m, 2H), 3.70-3.45 (m, 10H), 3.32 (s, 3H), 3.24 (m, 2H), 3.04 (m, 1H), 2.55-2.75 (m, 2H), 2.8 (s, 3H), 2.30 (m, 1H), 1.25 (m, 2H); MS (EI) for $C_{26}H_{35}Cl_2N_3O_3$: 508.2659 (MH+). The free base was dissolved in 4M hydrochloride in 2-propanol. The mixture was concentrated to afford product as a dihydrochloride salt.

Example 30

Preparation of 2-(3,4-dichlorophenyl)-N—((S)-2-((S)-3-(2-(2-ethoxyethoxy)ethoxy)pyrrolidin-1-yl)-1-phenylethyl)-N-methylacetamide, hydrochloride salt

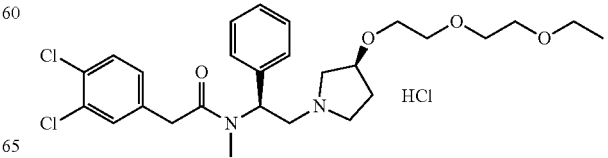

2-(3,4-Dichlorophenyl)-N—((S)-2-((S)-3-(2-(2-ethoxy-ethoxy)ethoxy)pyrrolidin-1-yl)-1-phenylethyl)-N-methylac-etamide hydrochloride was synthesized according to the following steps.

Step 1: Preparation of (S)-3-(2-(2-(2-(trifluo-romethoxy)ethoxy)ethoxy)ethoxy)pyrrolidine

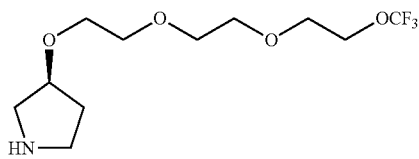 [SMILES: FC(F)(F)OCCOCCOCCO[C@H]1CCNC1]

(S)-tert-Butyl 3-hydroxypyrrolidine-1-carboxylate (6.0 g, 32.04 mmol) was dissolved in THF (120 mL). To the above mixture, K'OBu (3.60 g, 32.04 mmol) was added and the reaction mixture was heated to 65° C. for two hours. The mixture was cooled to ambient temperature. 2-(2-(2-(Trif-luoromethoxy)ethoxy)ethoxy)ethyl methanesulfonate (9.49 g, 32.04 mmol) was added and stirred for eighteen hours. The above mixture was concentrated under reduced pressure. The residue was dissolved in DCM (120 mL) and the resulting solution was washed with water (50 mL×2). The organic layer was dried over anhyhydrous $Na_2SO_4$ and concentrated under vacuum to obtain a thick oil. The oil was dissolved in DCM/TFA (2:1) (25 mL) and stirred for four hours at ambient temperature and then concentrated under vacuum. The residue was dissolved in water (35 mL) and the pH of the mixture was adjusted to 9 using 10% aqueous $Na_2CO_3$. The aqueous layer was extracted with DCM (50 mL×3). The combined DCM layers were dried over anhy-drous $Na_2SO_4$ and concentrated under reduced pressure. The crude was purified by column chromatography and yielded (S)-3-(2-(2-(2-(trifluoromethoxy)ethoxy)ethoxy)ethoxy) pyrrolidine (2.0 g, 21% yield) as an oil.

Step 2: Preparation of benzyl ((S)-2-oxo-1-phenyl-2-((S)-3-(2-(2-(2-(trifluoromethoxy) ethoxy)ethoxy) ethoxy)pyrrolidin-1-yl)ethyl)carbamate

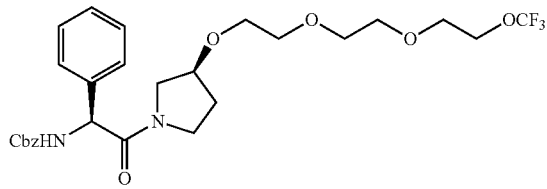 [SMILES: O=C(N[C@H](C(=O)N1CC[C@H](OCCOCCOCCOC(F)(F)F)C1)c1ccccc1)OCc1ccccc1]

(S)-3-(2-(2-(2-(Trifluoromethoxy)ethoxy)ethoxy)ethoxy) pyrrolidine (1.1 g, 3.83 mmol), (S)-2-(((benzyloxy)carbo-nyl)amino)-2-phenylacetic acid (1.092 g, 3.83 mmol) and DIPEA (1.485 g, 11.49 mmol) were dissolved in ACN (10 mL). The above mixture was stirred for fifteen minutes at ambient temperature and then cooled to 0° C. O-(Benzotri-azol-1-yl)-N,N,N',N'-tetramethyluronium tetrafluoroborate (TBTU) (1.475 g, 4.59 mmol) was added into the solution and stirred for one hour at 0° C. and for four hours at ambient temperature. After four hours, the mixture was concentrated under reduced pressure. The residue thus obtained was dissolved in DCM (50 mL) and washed with brine (25 mL×2). The DCM layer was dried over anhydrous $Na_2SO_4$ and concentrated. The crude compound was puri-fied by column chromatography and yielded benzyl ((S)-2-oxo-1-phenyl-2-((S)-3-(2-(2-(2-(trifluoromethoxy)ethoxy) ethoxy)ethoxy)pyrrolidin-1-yl)ethyl)carbamate (1.0 g, 47% yield).

Step 3: Preparation of (S)-2-((S)-3-(2-(2-ethoxy-ethoxy)ethoxy)pyrrolidin-1-yl)-N-methyl-1-phenyle-thanamine

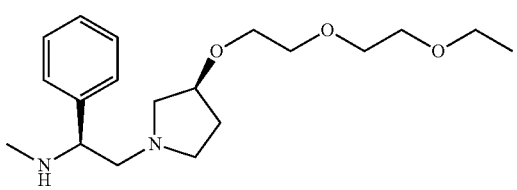 [SMILES: CCOCCOCCO[C@H]1CCN(C[C@@H](NC)c2ccccc2)C1]

To a three neck round bottom flask, benzyl ((S)-2-oxo-1-phenyl-2-((S)-3-(2-(2-(2-(trifluoromethoxy)ethoxy)ethoxy) ethoxy) pyrrolidin-1-yl)ethyl)carbamate (1.0 g, 1.803 mmol) was dissolved in THF (10 mL) under a nitrogen atmosphere. The above mixture was cooled to 0° C. and an LAH tablet (0.342 g, 9.02 mmol) was added and stirred for fifteen minutes at 0° C. and then heated to 65° C. for four hours. A 3N aq. $Na_2CO_3$ solution was added slowly until effervescence ceased. The precipitated solid was filtered and washed with DCM (100 mL). The filtrate was concentrated and the residue was dissolved in DCM (150 mL), washed with brine, dried over anhydrous $Na_2SO_4$ and concentrated under vacuum to get (S)-2-((S)-3-(2-(2-ethoxyethoxy) ethoxy)pyrrolidin-1-yl)-N-methyl-1-phenylethanamine (1.0 g, 49% yield).

Step 4: Preparation of 2-(3,4-dichlorophenyl)-N—((S)-2-((S)-3-(2-(2 ethoxyethoxy)ethoxy)pyrrolidin-1-yl)-1-phenylethyl)-N-methylacetamide hydrochlo-ride

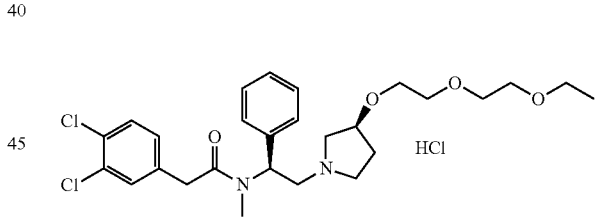

To a three neck round bottom flask (S)-2-((S)-3-(2-(2-ethoxyethoxy)ethoxy)pyrrolidin-1-yl)-N-methyl-1-phenyle-thanamine (300 mg, 0.892 mmol), 2-(3,4-dichlorophenyl) acetic acid (183 mg, 0.892 mmol), and DIPEA (346 mg, 2.67 mmol) were dissolved in ACN (10 mL). The mixture was stirred for fifteen minutes at ambient temperature and then cooled to 0° C. O-(Benzotriazol-1-yl)-N,N,N',N'-tetram-ethyluronium tetrafluoroborate (TBTU) (343 mg, 1.070 mmol) was added into the solution. The resulting mixture was stirred for eighteen hours at ambient temperature. After eighteen hours, the reaction mixture was concentrated and the residue was dissolved in DCM (100 mL). The organic layer was washed with $H_2O$, dried over anhydrous $Na_2SO_4$ and concentrated under reduced pressure. The residue thus obtained was purified by flash column chromatography and yielded 2-(3,4-dichlorophenyl)-N—((S)-2-((S)-3-(2-(2-ethoxyethoxy)ethoxy)pyrrolidin-1-yl)-1-phenylethyl)-N-methylacetamide (150 mg, 32% yield). $^1$H NMR (500 MHz, $CDCl_3$): δ 7.40 (m, 2H), 7.32 (m, 2H), 7.25 (m, 2H), 7.20-7.10 (m, 2H), 6.10 (m, 1H), 4.25 (m, 2H), 4.1 (br, s, 1H), 3.85 (br, s, 1H), 3.65 (m, 12H), 3.4-3.3 (m, 1H), 3.2 (br, s, 1H), 2.9-2.8 (br, s, 3H), 2.40 (m, 1H), 2.2 (m, 1H), 2.0 (m, 1H); MS (EI) for $C_{27}H_{36}Cl_2N_2O_4$: 523 (MH$^+$). The free base was dissolved in 4M hydrochloride in 2-propanol. The mixture was concentrated to afford 2-(3,4-dichlorophenyl)-N—((S)-2-((S)-3-(2-(2-ethoxyethoxy)ethoxy)pyrrolidin-1-yl)-1-phenylethyl)-N-methylacetamide hydrochloride.

Example 31 (Prophetic)

Synthesis of 2-(2-(2-(((S)-1-((S)-2-(2-(3,4-dichlorophenyl)-N-methylacetamido)-2-phenylethyl)pyrrolidin-3-yl)amino)ethoxy)ethoxy)acetic acid

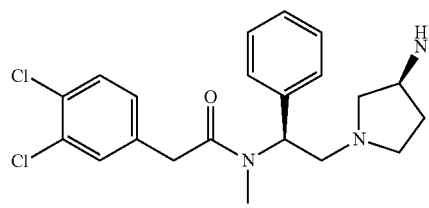

A solution of 2-(3,4-dichlorophenyl)-N—((S)-2-((S)-3-((2-(2-(2-hydroxyethoxy)ethoxy)ethyl)amino)pyrrolidin-1-yl)-1-phenylethyl)-N-methylacetamide (preparation described in Example 17) (1.0 equivalent) and reagent-grade acetone is placed in a flask under nitrogen and cooled to 0° C. To the stirred solution is added dropwise a solution consisting of Jones reagent and reagent-grade acetone. The Jones solution is added over a period of about 20 minutes. Isopropyl alcohol is then added dropwise to destroy excess Jones reagent. The reaction mixture is extracted twice with diethyl ether, and the combined ether extracts are washed (water, sodium bicarbonate, and saturated sodium chloride), dried over anhydrous sodium sulfate, and concentrated under reduced pressure. The residue is purified by chromatography to give 2-(2-(2-(((S)-1-((S)-2-(2-(3,4-dichlorophenyl)-N-methylacetamido)-2-phenylethyl)pyrrolidin-3-yl)amino)ethoxy)ethoxy)acetic acid.

Example 32 (Prophetic)

Synthesis of 2-(2-(((S)-1-((S)-2-(2-(3,4-dichlorophenyl)-N-methylacetamido)-2-phenylethyl)pyrrolidin-3-yl)amino)ethoxy)acetic acid

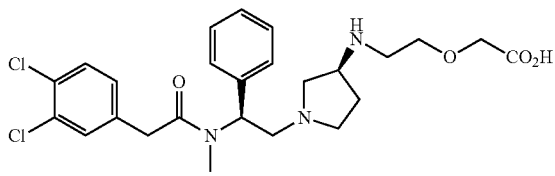 [SMILES: CN(C(=O)Cc1ccc(Cl)c(Cl)c1)[C@H](CN1CC[C@H](NCCOCC(=O)O)C1)c1ccccc1]

A solution of 2-(3,4-dichlorophenyl)-N—((S)-2-((S)-3-((2-(2-hydroxyethoxy)ethyl)amino)pyrrolidin-1-yl)-1-phenylethyl)-N-methylacetamide (preparation described in Example 19) (1.0 equivalent) and reagent-grade acetone is placed in a flask under nitrogen and cooled to 0° C. To the stirred solution is added dropwise a solution consisting of Jones reagent and reagent-grade acetone. The Jones solution is added over a period of about 20 minutes. Isopropyl alcohol is then added dropwise to destroy excess Jones reagent. The reaction mixture is extracted twice with diethyl ether, and the combined ether extracts are washed (water, sodium bicarbonate, and saturated sodium chloride), dried over anhydrous sodium sulfate, and concentrated under reduced pressure. The residue is purified by chromatography to give 2-(2-(((S)-1-((S)-2-(2-(3,4-dichlorophenyl)-N-methylacetamido)-2-phenylethyl)pyrrolidin-3-yl)amino)ethoxy)acetic acid.

Example 33 (Prophetic)

Synthesis of 2-(((S)-1-((S)-2-(2-(3,4-dichlorophenyl)-N-methylacetamido)-2-phenylethyl)pyrrolidin-3-yl)amino)acetic acid

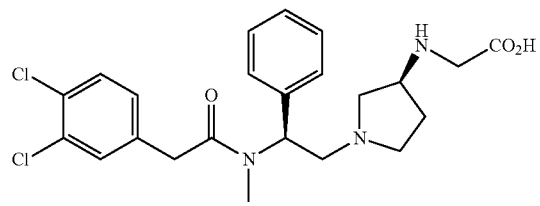 [SMILES: CN(C(=O)Cc1ccc(Cl)c(Cl)c1)[C@H](CN1CC[C@H](NCC(=O)O)C1)c1ccccc1]

A solution of 2-(3,4-dichlorophenyl)-N—((S)-2-((S)-3-((2-hydroxyethyl)amino)pyrrolidin-1-yl)-1-phenylethyl)-N-methylacetamide (1.0 equivalent) and reagent-grade acetone is placed in a flask under nitrogen and cooled to 0° C. To the stirred solution is added dropwise a solution consisting of Jones reagent and reagent-grade acetone. The Jones solution is added over a period of about 20 minutes. Isopropyl alcohol is then added dropwise to destroy excess Jones reagent. The reaction mixture is extracted twice with diethyl ether, and the combined ether extracts are washed (water, sodium bicarbonate, and saturated sodium chloride), dried over anhydrous sodium sulfate, and concentrated under reduced pressure. The residue is purified by chromatography to give 2-(((S)-1-((S)-2-(2-(3,4-dichlorophenyl)-N-methylacetamido)-2-phenylethyl)pyrrolidin-3-yl)amino)acetic acid.

Example 34 (Prophetic)

Preparation of 2-(3,4-dichlorophenyl)-N-methyl-N—((S)-1-phenyl-2-((S)-3-((2-(2-(2-(trifluoromethoxy)ethoxy)ethoxy)ethyl)amino)pyrrolidin-1-yl)ethyl)acetamide, hydrochloride salt

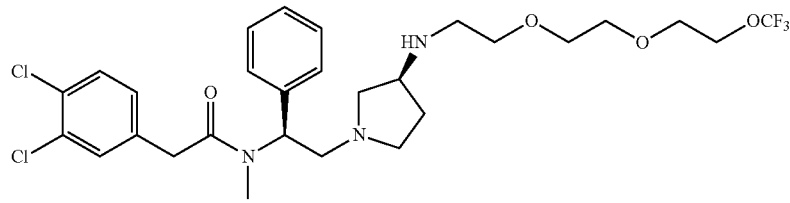 [SMILES: CN(C(=O)Cc1ccc(Cl)c(Cl)c1)[C@H](CN1CC[C@H](NCCOCCOCCOC(F)(F)F)C1)c1ccccc1]

2-(3,4-dichlorophenyl)-N-methyl-N—((S)-1-phenyl-2-((S)-3-((2-(2-(2-(trifluoromethoxy)ethoxy)ethoxy)ethyl)amino)pyrrolidin-1-yl)ethyl)acetamide was synthesized according to the following steps. A solution of N—((S)-2-((S)-3-aminopyrrolidin-1-yl)-1-phenylethyl)-2-(3,4-dichlorophenyl)-N-methylacetamide (640 mg, 1.58 mmol) in 1,4-dioxane:H$_2$O (5 vol) containing sodium lauryl sulphate (45 mg, 0.158 mmol) and K$_2$CO$_3$ (530 mg, 4.79 mmol) is reacted with 1-bromo-2-(2-(2-(trifluoromethoxy)ethoxy)ethoxy)ethane (450 mg, 1.90 mmol) at 80° C. for sixteen hours. After completion of the reaction, the crude compound is purified by column chromatography to afford 2-(3,4-dichlorophenyl)-N-methyl-N—((S)-1-phenyl-2-((S)-3-((2-(2-(2-(trifluoromethoxy)ethoxy)ethoxy)ethyl)amino)pyrrolidin-1-yl)ethyl)acetamide. The free base is then reacted with 4M HCl in IPA to afford the product as a hydrochloride salt.

Example 35 (Prophetic)

Preparation of N—((S)-2-((2S,4R)-2-(5,8,11-trioxa-2-azadodecyl)-4-hydroxypyrrolidin-1-yl)-1-phenylethyl)-2-(3,4-dichlorophenyl)-N-methylacetamide, dihydrochloride salt

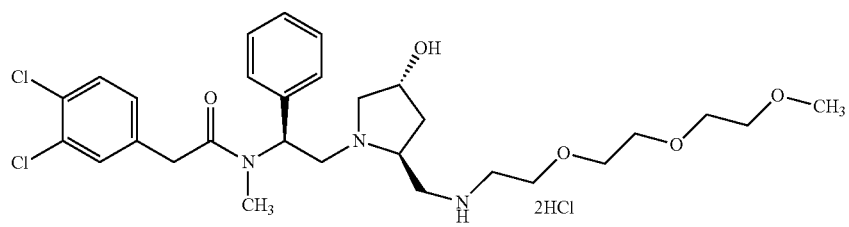 [SMILES: COCCOCCOCCNC[C@@H]1C[C@@H](O)CN1C[C@H](c1ccccc1)N(C)C(=O)Cc1ccc(Cl)c(Cl)c1]

N—((S)-2-((2S,4R)-2-(5,8,11-trioxa-2-azadodecyl)-4-hydroxypyrrolidin-1-yl)-1-phenylethyl)-2-(3,4-dichlorophenyl)-N-methylacetamide is synthesized according to the following steps.

Step 1: Preparation of (2S,4R)-methyl 1-((S)-2-(((benzyloxy)carbonyl)amino)-2-phenylacetyl)-4-hydroxypyrrolidine-2-carboxylate

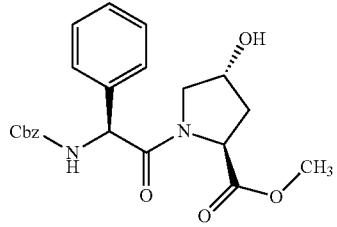 [SMILES: COC(=O)[C@@H]1C[C@@H](O)CN1C(=O)[C@@H](NC(=O)OCc1ccccc1)c1ccccc1]

A mixture of (S)-2-(((benzyloxy)carbonyl)amino)-2-phenylacetic acid (1 equiv), TBTU (1.1 equiv) and DIPEA (3 equiv) is reacted with (2S,4R)-methyl 4-hydroxypyrrolidine-2-carboxylate (1.1 equiv) in ACN for sixteen hours. After completion of the reaction, the crude is purified by column chromatography to afford (2S,4R)-methyl 1-((S)-2-(((benzyloxy)carbonyl)amino)-2-phenylacetyl)-4-hydroxypyrrolidine-2-carboxylate.

Step 2: Preparation of (2S,4R)-methyl 1-((S)-2-(((benzyloxy)carbonyl)amino)-2-phenylacetyl)-4-((tetrahydro-2H-pyran-2-yl)oxy)pyrrolidine-2-carboxylate

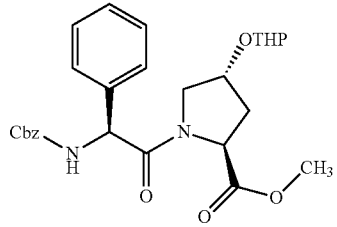

A mixture of (2S,4R)-methyl 1-((S)-2-(((benzyloxy)carbonyl)amino)-2-phenylacetyl)-4-hydroxypyrrolidine-2-carboxylate (1 equiv) is reacted with 3,4-dihydro-2H-pyran (1.10 equiv) in presence of PTSA (0.1 equiv) in dichloromethane. After completion of the reaction, the crude is purified by column chromatography to afford (2S,4R)-methyl 1-((S)-2-(((benzyloxy)carbonyl)amino)-2-phenylacetyl)-4-((tetrahydro-2H-pyran-2-yl)oxy)pyrrolidine-2-carboxylate.

Step 3: Preparation of ((2S,4R)-1-((S)-2-(methylamino)-2-phenylethyl)-4-((tetrahydro-2H-pyran-2-yl)oxy)pyrrolidin-2-yl)methanol

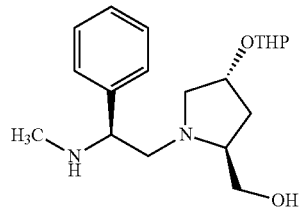

A solution of (2S,4R)-methyl 1-((S)-2-(((benzyloxy)carbonyl)amino)-2-phenylacetyl)-4-((tetrahydro-2H-pyran-2-yl)oxy)pyrrolidine-2-carboxylate (1 equiv) in THF is reacted with LAH (5 equiv) at 60° C. for sixteen hours. After completion of the reaction the mixture is quenched with water under cold conditions and is extracted into EtOAc. The organic layer is concentrated under vacuum to obtain a crude product, which upon further purification using column chromatography affords ((2S,4R)-1-((S)-2-(methylamino)-2-phenylethyl)-4-((tetrahydro-2H-pyran-2-yl)oxy)pyrrolidin-2-yl)methanol.

Step 4: Preparation of 2-(3,4-dichlorophenyl)-N-((1S)-2-((2S,4R)-2-(hydroxymethyl)-4-((tetrahydro-2H-pyran-2-yl)oxy)pyrrolidin-1-yl)-1-phenylethyl)-N-methylacetamide

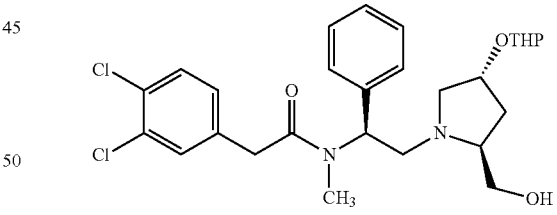

A mixture of ((2S,4R)-1-((S)-2-(methylamino)-2-phenylethyl)-4-((tetrahydro-2H-pyran-2-yl)oxy)pyrrolidin-2-yl)methanol (1 equiv), TBTU (1.2 equiv) and DIPEA (3 equiv) in ACN is reacted with 2-(3,4-dichlorophenyl)acetic acid (1.1 equiv) for sixteen hours at ambient temperature. After completion of the reaction, the crude compound is purified by column chromatography to afford 2-(3,4-dichlorophenyl)-N-((1S)-2-((2S,4R)-2-(hydroxymethyl)-4-((tetrahydro-2H-pyran-2-yl)oxy)pyrrolidin-1-yl)-1-phenylethyl)-N-methylacetamide.

Step 5: Preparation of ((2S,4R)-1-((S)-2-(2-(3,4-dichlorophenyl)-N-methylacetamido)-2-phenylethyl)-4-((tetrahydro-2H-pyran-2-yl)oxy)pyrrolidin-2-yl)methyl methanesulfonate

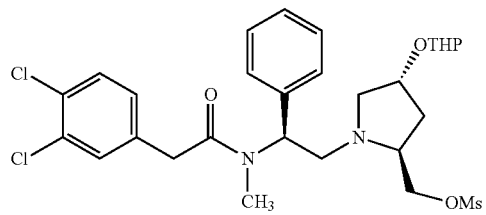

A solution of 2-(3,4-dichlorophenyl)-N-((1S)-2-((2S,4R)-2-(hydroxymethyl)-4-((tetrahydro-2H-pyran-2-yl)oxy)pyrrolidin-1-yl)-1-phenylethyl)-N-methylacetamide (1 equiv.) and TEA (1.20 equiv.) in dichloromethane is reacted with MsCl (1.10 equiv.) for two hours at ambient temperature. After completion of the reaction, the mixture is washed with water and concentrated under vacuum to afford ((2S,4R)-1-((S)-2-(2-(3,4-dichlorophenyl)-N-methylacetamido)-2-phenylethyl)-4-((tetrahydro-2H-pyran-2-yl)oxy)pyrrolidin-2-yl)methyl methanesulfonate.

Step 6: Preparation of N-((1S)-2-((2S,4R)-2-(5,8,11-trioxa-2-azadodecyl)-4-((tetrahydro-2H-pyran-2-yl)oxy)pyrrolidin-1-yl)-1-phenylethyl)-2-(3,4-dichlorophenyl)-N-methylacetamide

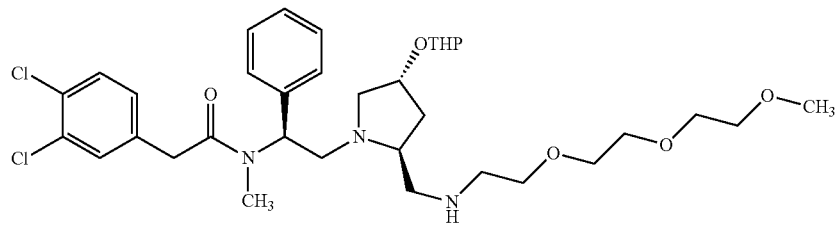

A mixture of ((2S,4R)-1-((S)-2-(2-(3,4-dichlorophenyl)-N-methylacetamido)-2-phenylethyl)-4-((tetrahydro-2H-pyran-2-yl)oxy)pyrrolidin-2-yl)methyl methanesulfonate (1 equiv), TEA (1.20 equiv) in DMF, is reacted with 2-(2-(2-methoxyethoxy)ethoxy)ethanamine (1.1 euiv) for eight hours. After completion of the reaction, the mixture is quenched in water. The compound is extracted into EtOAc twice. The combined EtOAc layer is washed with water and concentrated under vacuum to afford N-((1S)-2-((2S,4R)-2-(5,8,11-trioxa-2-azadodecyl)-4-((tetrahydro-2H-pyran-2-yl)oxy)pyrrolidin-1-yl)-1-phenylethyl)-2-(3,4-dichlorophenyl)-N-methylacetamide.

Step 7: Preparation of N-((1S)-2-((2S,4R)-2-(5,8,11-trioxa-2-azadodecyl)-4-((tetrahydro-2H-pyran-2-yl)oxy)pyrrolidin-1-yl)-1-phenylethyl)-2-(3,4-dichlorophenyl)-N-methylacetamide, dihydrochloride salt

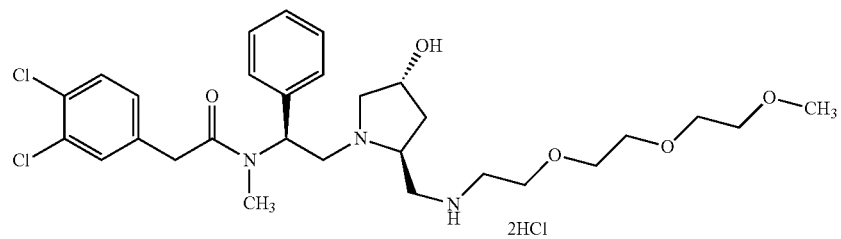 [SMILES: COCCOCCOCCNC[C@@H]1C[C@@H](O)CN1C[C@H](c1ccccc1)N(C)C(=O)Cc1ccc(Cl)c(Cl)c1]

A solution of N-((1S)-2-((2S,4R)-2-(5,8,11-trioxa-2-azadodecyl)-4-((tetrahydro-2H-pyran-2-yl)oxy)pyrrolidin-1-yl)-1-phenylethyl)-2-(3,4-dichlorophenyl)-N-methylacetamide (1 equiv) in dichloromethane is reacted with 4M HCl in IPA (5 equiv). After completion of the reaction, the mixture is concentrated under vacuum to afford N-((1S)-2-((2S,4R)-2-(5,8,11-trioxa-2-azadodecyl)-4-((tetrahydro-2H-pyran-2-yl)oxy)pyrrolidin-1-yl)-1-phenylethyl)-2-(3,4-dichlorophenyl)-N-methylacetamide, dihydrochloride salt.

Example 36 (Prophetic)

Preparation of N—((S)-2-((S)-3-(tert-butylamino)pyrrolidin-1-yl)-1-(4-(2-hydroxyethoxy)phenyl)ethyl)-2-(3,4-dichlorophenyl)-N-methylacetamide

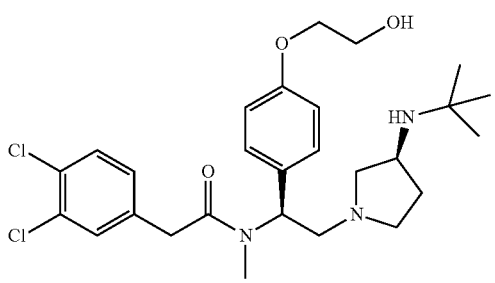 [SMILES: CN(C(=O)Cc1ccc(Cl)c(Cl)c1)[C@H](CN1CC[C@H](NC(C)(C)C)C1)c1ccc(OCCO)cc1]

To a solution of (R)-1-((S)-2-(2-(3,4-dichlorophenyl)-N-methylacetamido)-2-(4-(2-hydroxyethoxy)phenyl)ethyl)pyrrolidin-3-yl methanesulfonate (0.5 g, 0.92 mmol) (preparation described in Step 5 of Example 25) in acetonitrile (10 mL) is added 2-methylpropan-2-amine (0.08 g, 1.1 mmol) and potassium carbonate (0.153 g, 1.11 mmol). The mixture is heated to 70° C. for four hours. Dichloromethane (100 mL) is added into the mixture and resultant solution is washed with water and dried over sodium sulfate. The residue is purified by column chromatography. Using conventional techniques, a salt form of the compounds is made.

Example 37 (Prophetic)

Preparation of 2-(3,4-dichlorophenyl)-N—((S)-1-(4-(2-hydroxyethoxy)phenyl)-2-((S)-3-(methylamino)pyrrolidin-1-yl)ethyl)-N-methylacetamide

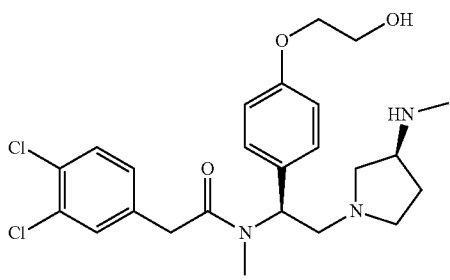 [SMILES: CN[C@H]1CCN(C[C@H](c2ccc(OCCO)cc2)N(C)C(=O)Cc2ccc(Cl)c(Cl)c2)C1]

Using a synthetic approach similar to the one employed in Example 35. The compound 2-(3,4-dichlorophenyl)-N—((S)-1-(4-(2-hydroxyethoxy)phenyl)-2-((S)-3-(methylamino)pyrrolidin-1-yl)ethyl)-N-methylacetamide is prepared. Using conventional techniques, a salt form of the compounds is made.

Example 38 (Prophetic)

Preparation of 2-(3,4-dichlorophenyl)-N—((S)-2-((S)-3-(dimethylamino)pyrrolidin-1-yl)-1-(4-(2-hydroxyethoxy)phenyl)ethyl)-N-methylacetamide

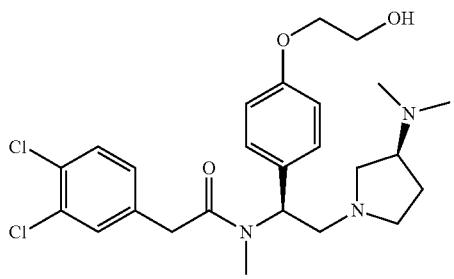 [SMILES: CN(C)[C@H]1CCN(C[C@H](c2ccc(OCCO)cc2)N(C)C(=O)Cc2ccc(Cl)c(Cl)c2)C1]

Using a synthetic approach similar to the one employed in Example 35, 2-(3,4-dichlorophenyl)-N—((S)-2-((S)-3-(dimethylamino)pyrrolidin-1-yl)-1-(4-(2-hydroxyethoxy)phenyl)ethyl)-N-methylacetamide is prepared. Using conventional techniques, a salt form of the compounds is made.

It is understood that each of Examples 1-38 described above may be modified to introduce oligomers of various lengths for each compound, as disclosed herein.

Example 39

Biology Data of Selected Compounds

Selected compounds were assayed for various biological properties.

The binding affinities of certain compounds of the present invention were evaluated using radioligand binding assays in membranes prepared from CHO-K1 cells expressing recombinant human kappa (KOR) or mu (MOR) opioid receptors.

Competitive Binding a KOR and MOR: Competition binding experiments were conducted by incubating membrane protein to equilibrium in triplicate in the presence of a fixed concentration of radioligand and increasing concentrations of test compound for evaluation of binding to KOR or single concentration (10 μM) of test compound for evaluation of binding to MOR in 101 μL final volume. The radioligands used were specific for each receptor type, and the assay conditions are described in Table 1. Following incubations, the membranes were rapidly filtered through GF/B filter plate (presoaked with 0.5% polyethyleneimine), washed five times with cold 50 mM Tris-HCl, pH 7.5, and the bound radioactivity was then measured by liquid scintillation counting. Non-specific binding was measured in the presence of excess ligand; this value was subtracted from the total binding to yield the specific binding at each test concentration. Assay conditions are reported in Table 1 below.

TABLE 1

| Receptor | Receptor Source | Membrane Protein | Radioligand | $K_d$ | Non-specific binding | Methods |
|---|---|---|---|---|---|---|
| Kappa Opioid | Human recombinant in CHO-K1 cells | 2.5 µg/well | [$^3$H] Diprenorphine (1 nM) | 0.3 nM | U-50488 (10 µM) | Reaction in 50 mM Tris-HCl (pH 7.5), 5 mM MgCl$_2$, 0.05% BSA at room temperature for 1 h with shaking |
| Mu Opioid | Human recombinant in CHO-K1 cells | 5 µg/well | [$^3$H] Naloxone (4 nM) | — | Naloxone (10 µM) | Reaction in 50 mM Tris-HCl (pH 7.5), 5 mM MgCl$_2$ at room temperature for 1 h with shaking |

For KOR binding, IC$_{50}$ (concentration of test compound required to inhibit 50% of specific binding) values were obtained from non-linear regression analysis of dose-response curves, using GraphPad's Prism 5.01 software, and were calculated for those compounds that showed >50% inhibition of specific binding at the highest concentration tested. K$_i$ (affinity of test compound) was obtained using the Cheng Prusoff correction using experimental K$_d$ (affinity of radioligand) values that were previously determined under these assay conditions. For MOR binding, compounds were tested at one concentration, 10 µM, to evaluate its ability to inhibit specific radioligand binding. The values are expressed as percent inhibition of specific binding and greater than 50% inhibition of binding was considered to be significant.

Inhibition of cAMP Accumulation:

Inhibition of cAMP accumulation by select compounds was measured in forskolin-stimulated CHO-K1 cells stably expressing KOR. CHO-K1 cells stably expressing KOR were harvested using Invitrogen Cell Dissociation Buffer, and then centrifuged at 1200 rpm for five minutes. The supernatant was aspirated and cells were resuspended in assay buffer to a density of 4×10$^5$ cells/mL. 25 µL of cells were added into a white half-area 96 well plate. Fourteen point serial dilutions of test compounds were carried out in assay buffer (PBS with 0.5 mM IBMX). Dynorphin A or U62066 was used as a positive control for each assay. Compound (12.5 µL) was added to the cells in duplicate for each test concentration. The cells were then stimulated with 12.5 µL forskolin at a final concentration 20 µM. Cells were incubated for 45 minutes in a 37° C., 5% CO$_2$ water jacketed incubator. CisBio HTRF cAMP assay reagent was used for cAMP quantitation. Two hours after substrate addition, signal at 665/615 nm was measured using the Perkin Elmer Victor X4 HTRF reader. Data analysis was done using GraphPad Prism, sigmoidal dose-response (variable slope) curve fitting.

Data are expressed as means of one experiment in triplicate determination and reported in Table 2.

TABLE 2

Binding Activities and Inhibition of cAMP Accumulation of Selected Compounds

| Compound No. (Example No.) | Kappa Opioid Receptor | | | Mu Opioid Receptor Mu Receptor Inhibition |
|---|---|---|---|---|
| | IC50 (nM) | Ki (nM) | EC50 cAMP (nM) | % inhib @ 10 uM |
| 1 | 37.1 | 4.84 | 2 | 89 |
| 2 | 5.36 | 0.7 | 0.311 | 87.1 |
| 3 | 2.79 | 0.36 | 0.29 | 94.2 |
| 4 | 49.71 | 6.48 | 1.75 | 91.8 |
| 5 | 7.74 | 1.01 | 1.35 | 97 |
| 6 | 3.01 | 0.39 | 1.15 | 84.6 |
| 7 | 0.67 | 0.09 | 0.19 | 99.9 |
| 8 | 0.35 | 0.05 | 0.06 | 99 |
| 9 | 3.58 | 0.47 | 0.5 | 101.2 |
| 10 | 9.61 | 1.25 | 3.74 | 95.9 |
| 11 | 344.9 | 44.99 | 28.8 | 57.6 |
| 12 | 374.2 | 48.81 | 18.46 | 47.0 |
| 13 | 0.75 | 0.10 | 0.067 | 95.4 |
| 15 | 5.27 | 0.69 | 0.164 | 23.5 |
| 16 | 10.25 | 1.34 | 0.294 | 28.4 |
| 18 | 135.2 | 17.64 | 4.67 | -3.2 |
| 20 | 57410 | 7488 | 2673 | -29.4 |
| 21 | 1449 | 189 | 33.26 | 0.0 |
| 22 | 247.2 | 32.25 | 15.5 | -10.3 |
| 23 | 1081 | 141 | 53.6 | -2 |
| 24 | 20.81 | 2.71 | 0.78 | 40.1 |

What is claimed is:

1. A compound having the formula:

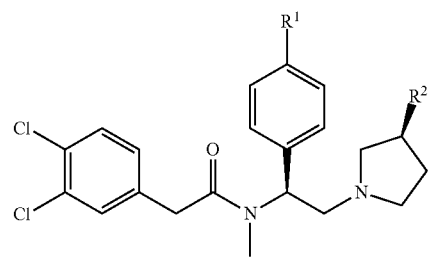

wherein:

R$^1$ is selected from H or —OCH$_2$CH$_2$OH;

R$^2$ is selected from —NH—(CH$_2$CH$_2$O)$_a$—Y or —NH—(CH$_2$CH$_2$O)$_a$—Y;

Y is selected from —CH$_3$, —CF$_3$, or —OH;

a is selected from 0, 1, 2, 3 and 4;

or pharmaceutically acceptable salts and solvates thereof.

2. The compound of claim 1 having the formula selected from:

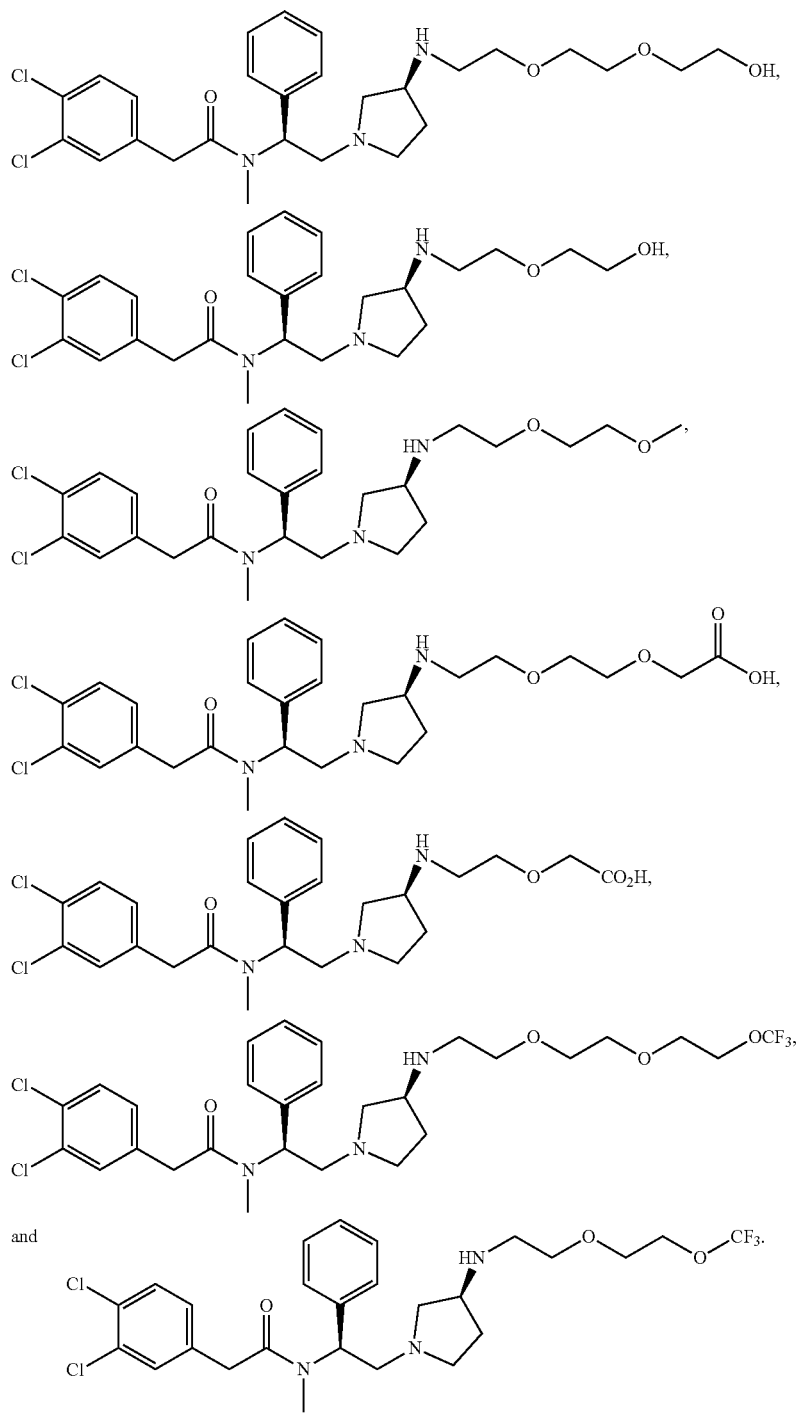

and

3. A pharmaceutical composition comprising the compound of claim 1 and at least one pharmaceutically acceptable excipient.

4. A composition of matter comprising the compound of claim 1, wherein the compound is present in a dosage form.

5. A method of treating pain comprising administering the compound of claim 1 to a patient in need thereof.

* * * * *